US009259342B2

(12) United States Patent
Wong et al.

(10) Patent No.: US 9,259,342 B2
(45) Date of Patent: *Feb. 16, 2016

(54) FEEDBACK SYSTEMS AND METHODS TO ENHANCE OBSTRUCTIVE AND OTHER OBESITY TREATMENTS, OPTIONALLY USING MULTIPLE SENSORS

(71) Applicant: IntraPace, Inc., San Jose, CA (US)

(72) Inventors: Ken Wong, Saratoga, CA (US); John C. Potosky, San Jose, CA (US); Rose Province, San Jose, CA (US); Charles R. Brynelsen, Menlo Park, CA (US); Mir Imran, Los Altos Hills, CA (US)

(73) Assignee: IntraPace, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/563,686

(22) Filed: Dec. 8, 2014

(65) Prior Publication Data

US 2015/0094526 A1  Apr. 2, 2015

Related U.S. Application Data

(63) Continuation of application No. 13/250,757, filed on Sep. 30, 2011, now Pat. No. 8,934,976.

(60) Provisional application No. 61/388,900, filed on Oct. 1, 2010.

(51) Int. Cl.
*A61N 1/00* (2006.01)
*A61F 5/00* (2006.01)

(52) U.S. Cl.
CPC .............. *A61F 5/0059* (2013.01); *A61F 5/003* (2013.01); *A61F 5/005* (2013.01); *A61F 5/0026* (2013.01);

(Continued)

(58) Field of Classification Search
CPC ...... A61F 5/005; A61F 5/0053; A61F 5/0063; A61F 5/0083; A61F 5/0076; A61F 5/0026; A61F 5/003; A61F 5/0003; A61F 2005/002
See application file for complete search history.

(56) References Cited

U.S. PATENT DOCUMENTS 3,411,507 A   11/1968   Wingrove
3,646,940 A   3/1972   Timm et al.

(Continued)

FOREIGN PATENT DOCUMENTS

AU   2002340624 B2   9/2007
AU   2002329174 B2   12/2007

(Continued)

OTHER PUBLICATIONS

U.S. Appl. No. 61/241,154, filed Sep. 10, 2009 by Province et al., 74 pages.

(Continued)

*Primary Examiner* — Robert N Wieland
(74) *Attorney, Agent, or Firm* — Kilpatrick Townsend and Stockton LLP

(57) ABSTRACT

Feedback systems and methods enhance obstructive and other obesity treatments by presenting feedback regarding patients' actual eating. An ingestion restricting implant body can be deployed along the gastrointestinal tract. In some embodiments, ingestion alters the implant body, which, in turn, generates signals. The generated signals can be used to inhibit unhealthy ingestion by the patient. In other embodiments, the implant body can be altered by signals so as to selectable change the restriction imposed on the gastrointestinal tract, optionally in response to ingestion events, an eating schedule, or the like. The implant body may comprise a gastric band. Sensor signals may be processed to identify ingestion and/or characterize ingestion material, and the results may be displayed on a screen for a patient or coach to view.

22 Claims, 33 Drawing Sheets

(52) U.S. Cl.
CPC .............. *A61F 5/0036* (2013.01); *A61F 5/0056* (2013.01); *A61F 5/0069* (2013.01); *A61F 2005/002* (2013.01); *A61F 2005/0023* (2013.01)

(56) References Cited

U.S. PATENT DOCUMENTS

| | | | |
|---|---|---|---|
| 3,662,758 A | 5/1972 | Glover | |
| 3,677,251 A | 7/1972 | Bowers | |
| 3,683,933 A | 8/1972 | Mansfield | |
| 3,735,766 A | 5/1973 | Bowers et al. | |
| 3,796,221 A | 3/1974 | Hagfors | |
| 3,815,611 A | 6/1974 | Denniston, III | |
| 3,835,864 A | 9/1974 | Rasor et al. | |
| 3,835,865 A | 9/1974 | Bowers | |
| 4,102,344 A | 7/1978 | Conway | |
| 4,178,105 A | 12/1979 | Sollich | |
| RE30,366 E | 8/1980 | Rasor et al. | |
| 4,592,339 A | 6/1986 | Kuzmak et al. | |
| 4,628,928 A | 12/1986 | Lowell | |
| 4,823,808 A | 4/1989 | Clegg | |
| 4,865,044 A | 9/1989 | Wallace et al. | |
| 4,921,481 A | 5/1990 | Danis et al. | |
| 4,922,930 A | 5/1990 | Adkins et al. | |
| 4,925,446 A | 5/1990 | Garay | |
| 4,951,197 A | 8/1990 | Mellinger | |
| 4,966,148 A | 10/1990 | Millar | |
| 5,080,663 A | 1/1992 | Mills et al. | |
| 5,112,310 A | 5/1992 | Grobe | |
| 5,144,952 A | 9/1992 | Frachet et al. | |
| 5,188,104 A | 2/1993 | Wernicke et al. | |
| 5,193,540 A | 3/1993 | Schulman et al. | |
| 5,197,491 A | 3/1993 | Anderson et al. | |
| 5,217,449 A | 6/1993 | Yuda et al. | |
| 5,234,454 A | 8/1993 | Bangs | |
| 5,261,916 A | 11/1993 | Engelson | |
| 5,263,480 A | 11/1993 | Wernicke et al. | |
| 5,292,344 A | 3/1994 | Douglas | |
| 5,415,181 A | 5/1995 | Hogrefe et al. | |
| 5,423,872 A | 6/1995 | Cigaina | |
| 5,438,985 A | 8/1995 | Essen-Moller | |
| 5,540,730 A | 7/1996 | Terry et al. | |
| 5,558,640 A | 9/1996 | Pfeiler et al. | |
| 5,626,630 A | 5/1997 | Markowitz et al. | |
| 5,673,691 A | 10/1997 | Abrams et al. | |
| 5,690,691 A | 11/1997 | Chen et al. | |
| 5,716,392 A | 2/1998 | Bourgeois et al. | |
| 5,766,234 A | 6/1998 | Chen et al. | |
| 5,767,791 A | 6/1998 | Stoop et al. | |
| 5,792,048 A | 8/1998 | Schaefer | |
| 5,800,445 A | 9/1998 | Ratcliff | |
| 5,836,994 A | 11/1998 | Bourgeois | |
| 5,861,014 A | 1/1999 | Familoni | |
| 5,865,843 A | 2/1999 | Baudino | |
| 5,928,195 A | 7/1999 | Malamud et al. | |
| 5,938,669 A | 8/1999 | Klaiber et al. | |
| 5,980,480 A | 11/1999 | Rubenstein et al. | |
| 5,984,860 A | 11/1999 | Shan | |
| 5,993,473 A | 11/1999 | Chan et al. | |
| 5,995,872 A | 11/1999 | Bourgeois | |
| 6,006,138 A | 12/1999 | Don Michael | |
| 6,026,326 A | 2/2000 | Bardy | |
| 6,041,258 A | 3/2000 | Cigaina et al. | |
| 6,059,719 A | 5/2000 | Yamamoto et al. | |
| 6,083,249 A | 7/2000 | Familoni | |
| 6,090,126 A | 7/2000 | Burns | |
| 6,091,992 A | 7/2000 | Bourgeois et al. | |
| 6,097,984 A | 8/2000 | Douglas | |
| 6,098,629 A | 8/2000 | Johnson et al. | |
| 6,104,955 A | 8/2000 | Bourgeois | |
| 6,115,635 A | 9/2000 | Bourgeois | |
| 6,115,636 A | 9/2000 | Ryan | |
| 6,144,867 A | 11/2000 | Walker et al. | |
| 6,150,951 A | 11/2000 | Olejniczak | |
| 6,162,195 A | 12/2000 | Igo et al. | |
| 6,183,411 B1 | 2/2001 | Mortier et al. | |
| 6,205,359 B1 | 3/2001 | Boveja | |
| 6,210,408 B1 | 4/2001 | Chandrasekaran et al. | |
| 6,214,032 B1 | 4/2001 | Loeb et al. | |
| 6,216,039 B1 | 4/2001 | Bourgeois | |
| 6,238,415 B1 | 5/2001 | Sepetka et al. | |
| 6,243,607 B1 | 6/2001 | Mintchev et al. | |
| 6,285,897 B1 | 9/2001 | Kilcoyne et al. | |
| 6,317,731 B1 | 11/2001 | Luciano | |
| 6,321,124 B1 | 11/2001 | Cigaina | |
| 6,327,503 B1 | 12/2001 | Familoni | |
| 6,358,197 B1 | 3/2002 | Silverman et al. | |
| 6,366,814 B1 | 4/2002 | Boveja et al. | |
| 6,381,495 B1 | 4/2002 | Jenkins | |
| 6,381,577 B1 | 4/2002 | Brown | |
| 6,427,089 B1 | 7/2002 | Knowlton | |
| 6,432,040 B1 | 8/2002 | Meah | |
| 6,449,511 B1 | 9/2002 | Mintchev et al. | |
| 6,453,199 B1 | 9/2002 | Kobozev | |
| 6,454,785 B2 | 9/2002 | De Hoyos Garza | |
| 6,457,536 B1 | 10/2002 | Bye et al. | |
| 6,477,423 B1 | 11/2002 | Jenkins | |
| 6,510,332 B1 | 1/2003 | Greenstein | |
| 6,513,532 B2 | 2/2003 | Mault et al. | |
| 6,529,778 B2 | 3/2003 | Prutchi | |
| 6,533,733 B1 | 3/2003 | Ericson et al. | |
| 6,535,764 B2 | 3/2003 | Imran et al. | |
| 6,540,789 B1 | 4/2003 | Silverman et al. | |
| 6,542,776 B1 | 4/2003 | Gordon et al. | |
| 6,564,101 B1 | 5/2003 | Zikria | |
| 6,571,127 B1 | 5/2003 | Ben-Haim et al. | |
| 6,572,629 B2 | 6/2003 | Kalloo et al. | |
| 6,591,137 B1 | 7/2003 | Fischeli et al. | |
| 6,600,953 B2 | 7/2003 | Flesler et al. | |
| 6,606,518 B1 | 8/2003 | Cigaina | |
| 6,606,523 B1 | 8/2003 | Jenkins | |
| 6,609,025 B2 | 8/2003 | Barrett et al. | |
| 6,611,715 B1 | 8/2003 | Boveja | |
| 6,615,084 B1 | 9/2003 | Cigaina | |
| 6,684,104 B2 | 1/2004 | Gordon et al. | |
| 6,689,056 B1 | 2/2004 | Kilcoyne et al. | |
| 6,699,186 B1 | 3/2004 | Wolinsky et al. | |
| 6,731,976 B2 | 5/2004 | Penn et al. | |
| 6,735,479 B2 | 5/2004 | Fabian et al. | |
| 6,754,536 B2 | 6/2004 | Swoyer et al. | |
| 6,778,854 B2 | 8/2004 | Puskas | |
| 6,826,428 B1 | 11/2004 | Chen et al. | |
| 6,876,885 B2 | 4/2005 | Swoyer et al. | |
| 6,879,859 B1 | 4/2005 | Boveja | |
| 6,879,970 B2 | 4/2005 | Shiffman et al. | |
| 6,895,278 B1 | 5/2005 | Gordon | |
| 6,895,279 B2 | 5/2005 | Loeb et al. | |
| 6,941,171 B2 | 9/2005 | Mann et al. | |
| 6,952,613 B2 | 10/2005 | Swoyer et al. | |
| 6,958,068 B2 | 10/2005 | Hieshima | |
| 6,973,412 B2 | 12/2005 | King et al. | |
| 7,016,735 B2 | 3/2006 | Imran et al. | |
| 7,020,526 B1 | 3/2006 | Zhao | |
| 7,020,531 B1 | 3/2006 | Colliou et al. | |
| 7,033,373 B2 | 4/2006 | de la Torre et al. | |
| 7,044,942 B2 | 5/2006 | Jolly et al. | |
| 7,054,690 B2 | 5/2006 | Imran | |
| 7,054,692 B1 | 5/2006 | Whitehurst et al. | |
| 7,076,305 B2 | 7/2006 | Imran et al. | |
| 7,079,977 B2 | 7/2006 | Osorio et al. | |
| 7,096,070 B1 | 8/2006 | Jenkins et al. | |
| 7,107,100 B2 | 9/2006 | Imran et al. | |
| 7,120,498 B2 | 10/2006 | Imran et al. | |
| 7,247,023 B2 | 7/2007 | Peplinski et al. | |
| 7,330,753 B2 | 2/2008 | Policker et al. | |
| 7,371,215 B2 | 5/2008 | Colliou et al. | |
| 7,399,304 B2 | 7/2008 | Gambale et al. | |
| 7,430,450 B2 | 9/2008 | Imran | |
| 7,463,934 B2 | 12/2008 | Tronnes et al. | |
| 7,483,754 B2 | 1/2009 | Imran et al. | |
| 7,502,649 B2 | 3/2009 | Ben-Haim et al. | |
| 7,509,174 B2 | 3/2009 | Imran et al. | |
| 7,509,175 B2 | 3/2009 | Sparks et al. | |
| 7,530,943 B2 | 5/2009 | Lechner | |

(56) References Cited

U.S. PATENT DOCUMENTS

| | | |
|---|---|---|
| 7,546,166 B2 | 6/2009 | Michels et al. |
| 7,558,629 B2 | 7/2009 | Keimel et al. |
| 7,580,751 B2 | 8/2009 | Starkebaum |
| 7,590,452 B2 | 9/2009 | Imran et al. |
| 7,593,777 B2 | 9/2009 | Gerber |
| 7,643,887 B2 | 1/2010 | Imran |
| 7,689,276 B2 | 3/2010 | Dobak |
| 7,689,284 B2 | 3/2010 | Imran et al. |
| 7,702,394 B2 | 4/2010 | Imran |
| 7,747,322 B2 | 6/2010 | Imran |
| 7,756,582 B2 | 7/2010 | Imran et al. |
| 8,019,422 B2 | 9/2011 | Imran et al. |
| 8,170,609 B2 | 5/2012 | Hedtke et al. |
| 8,190,261 B2 | 5/2012 | Imran |
| 8,239,027 B2 | 8/2012 | Imran |
| 8,364,269 B2 | 1/2013 | Imran |
| 8,489,189 B2 | 7/2013 | Tronnes |
| 8,636,648 B2 | 1/2014 | Gazdzinski |
| 8,715,181 B2 | 5/2014 | Brynelsen et al. |
| 8,934,976 B2 | 1/2015 | Wong et al. |
| 2001/0011543 A1 | 8/2001 | Forsell |
| 2001/0049470 A1 | 12/2001 | Mault et al. |
| 2002/0055757 A1 | 5/2002 | de la Torre et al. |
| 2002/0072780 A1 | 6/2002 | Foley |
| 2002/0103424 A1 | 8/2002 | Swoyer et al. |
| 2002/0103521 A1 | 8/2002 | Swoyer et al. |
| 2002/0103522 A1 | 8/2002 | Swoyer et al. |
| 2002/0161414 A1 | 10/2002 | Flesler et al. |
| 2002/0198570 A1 | 12/2002 | Puskas |
| 2002/0198571 A1 | 12/2002 | Puskas |
| 2003/0055463 A1 | 3/2003 | Gordon et al. |
| 2003/0120328 A1 | 6/2003 | Jenkins et al. |
| 2003/0144708 A1 | 7/2003 | Starkebaum |
| 2003/0167025 A1 | 9/2003 | Imran et al. |
| 2003/0195600 A1 | 10/2003 | Tronnes et al. |
| 2003/0212439 A1 | 11/2003 | Schuler et al. |
| 2004/0015201 A1 | 1/2004 | Greenstein |
| 2004/0059393 A1 | 3/2004 | Policker et al. |
| 2004/0088022 A1 | 5/2004 | Chen |
| 2004/0088023 A1 | 5/2004 | Imran et al. |
| 2004/0093039 A1 | 5/2004 | Schumert |
| 2004/0133089 A1 | 7/2004 | Kilcoyne et al. |
| 2004/0133390 A1 | 7/2004 | Osorio et al. |
| 2004/0147816 A1 | 7/2004 | Policker et al. |
| 2004/0162595 A1 | 8/2004 | Foley |
| 2004/0162945 A1 | 8/2004 | King et al. |
| 2004/0167583 A1 | 8/2004 | Knudson et al. |
| 2004/0172084 A1 | 9/2004 | Knudson et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172095 A1 | 9/2004 | Jenkins et al. |
| 2004/0176812 A1 | 9/2004 | Knudson et al. |
| 2004/0236381 A1 | 11/2004 | Dinsmoor et al. |
| 2004/0236382 A1 | 11/2004 | Dinsmoor et al. |
| 2004/0243195 A1 | 12/2004 | Imran et al. |
| 2005/0021101 A1 | 1/2005 | Chen et al. |
| 2005/0038454 A1 | 2/2005 | Loshakove |
| 2005/0049655 A1 | 3/2005 | Boveja et al. |
| 2005/0055039 A1 | 3/2005 | Burnett et al. |
| 2005/0065571 A1 | 3/2005 | Imran |
| 2005/0065575 A1 | 3/2005 | Dobak |
| 2005/0096514 A1 | 5/2005 | Starkebaum |
| 2005/0113649 A1 | 5/2005 | Bergantino |
| 2005/0113880 A1 | 5/2005 | Gordon |
| 2005/0131486 A1 | 6/2005 | Boveja et al. |
| 2005/0131487 A1 | 6/2005 | Boveja et al. |
| 2005/0137643 A1 | 6/2005 | Mintchev |
| 2005/0143760 A1 | 6/2005 | Imran |
| 2005/0143784 A1 | 6/2005 | Imran |
| 2005/0149141 A1 | 7/2005 | Starkebaum |
| 2005/0149142 A1 | 7/2005 | Starkebaum |
| 2005/0149146 A1 | 7/2005 | Boveja et al. |
| 2005/0159800 A1 | 7/2005 | Marshall et al. |
| 2005/0159801 A1 | 7/2005 | Marshall et al. |
| 2005/0192599 A1 | 9/2005 | Demarais |
| 2005/0222637 A1 | 10/2005 | Chen |
| 2005/0222638 A1* | 10/2005 | Foley et al. ............... 607/40 |
| 2005/0240085 A1 | 10/2005 | Knoell et al. |
| 2005/0251219 A1 | 11/2005 | Evans |
| 2005/0287499 A1 | 12/2005 | Yeager |
| 2006/0015016 A1 | 1/2006 | Thornton |
| 2006/0015149 A1 | 1/2006 | Baker |
| 2006/0020298 A1 | 1/2006 | Camilleri et al. |
| 2006/0025654 A1 | 2/2006 | Suzuki et al. |
| 2006/0036293 A1 | 2/2006 | Whitehurst et al. |
| 2006/0058851 A1 | 3/2006 | Cigaina |
| 2006/0064037 A1 | 3/2006 | Shaslon et al. |
| 2006/0069414 A1 | 3/2006 | Imran et al. |
| 2006/0074279 A1 | 4/2006 | Brover |
| 2006/0074335 A1 | 4/2006 | Ben-Oren et al. |
| 2006/0074457 A1 | 4/2006 | Imran et al. |
| 2006/0074458 A1 | 4/2006 | Imran |
| 2006/0085054 A1 | 4/2006 | Zikorus et al. |
| 2006/0089571 A1 | 4/2006 | Gertner |
| 2006/0089690 A1 | 4/2006 | Gerber |
| 2006/0089699 A1 | 4/2006 | Imran |
| 2006/0111753 A1 | 5/2006 | Imran et al. |
| 2006/0116736 A1 | 6/2006 | DiLorenzo |
| 2006/0122468 A1 | 6/2006 | Tavor |
| 2006/0122864 A1 | 6/2006 | Gottesman et al. |
| 2006/0173238 A1 | 8/2006 | Starkebaum |
| 2006/0183967 A1 | 8/2006 | Lechner |
| 2006/0212053 A1 | 9/2006 | Gertner |
| 2006/0224326 A1 | 10/2006 | St. Ores et al. |
| 2006/0224421 A1 | 10/2006 | St. Ores et al. |
| 2006/0247722 A1 | 11/2006 | Maschino et al. |
| 2006/0293609 A1 | 12/2006 | Stahmann et al. |
| 2007/0021979 A1 | 1/2007 | Cosentino et al. |
| 2007/0027493 A1 | 2/2007 | Ben-Haim et al. |
| 2007/0173703 A1 | 7/2007 | Lee et al. |
| 2007/0173705 A1 | 7/2007 | Teller et al. |
| 2007/0179351 A1 | 8/2007 | Kil et al. |
| 2007/0179359 A1 | 8/2007 | Goodwin |
| 2007/0270663 A1 | 11/2007 | Ng et al. |
| 2007/0299481 A1 | 12/2007 | Syed et al. |
| 2008/0065169 A1 | 3/2008 | Colliou et al. |
| 2008/0139891 A1 | 6/2008 | Whitehead et al. |
| 2008/0161715 A1 | 7/2008 | Stivoric et al. |
| 2008/0161875 A1 | 7/2008 | Stone |
| 2008/0183090 A1 | 7/2008 | Farringdon et al. |
| 2008/0208010 A1 | 8/2008 | Boyden et al. |
| 2008/0250340 A1 | 10/2008 | Dlugos |
| 2008/0294019 A1 | 11/2008 | Tran |
| 2008/0312678 A1 | 12/2008 | Pasricha |
| 2009/0012433 A1 | 1/2009 | Fernstrom et al. |
| 2009/0018605 A1 | 1/2009 | Imran et al. |
| 2009/0030474 A1 | 1/2009 | Brynelsen et al. |
| 2009/0054914 A1 | 2/2009 | Lechner |
| 2009/0062624 A1 | 3/2009 | Neville |
| 2009/0076842 A1 | 3/2009 | Schwarzberg et al. |
| 2009/0105785 A1 | 4/2009 | Wei et al. |
| 2009/0118590 A1 | 5/2009 | Teller et al. |
| 2009/0149910 A1 | 6/2009 | Imran et al. |
| 2009/0192404 A1 | 7/2009 | Ortiz et al. |
| 2009/0192541 A1 | 7/2009 | Ortiz et al. |
| 2009/0222057 A1 | 9/2009 | Imran |
| 2009/0299434 A1 | 12/2009 | Imran et al. |
| 2009/0306462 A1 | 12/2009 | Lechner |
| 2009/0312631 A1* | 12/2009 | Rabinovitz et al. ......... 600/431 |
| 2010/0094374 A1 | 4/2010 | Imran |
| 2010/0114595 A1 | 5/2010 | Richard |
| 2010/0152532 A1 | 6/2010 | Marcotte |
| 2010/0160745 A1 | 6/2010 | Hills et al. |
| 2010/0217213 A1 | 8/2010 | Forsell |
| 2010/0234693 A1 | 9/2010 | Srinivasan et al. |
| 2010/0240962 A1 | 9/2010 | Contant |
| 2010/0280332 A1 | 11/2010 | Hyde et al. |
| 2010/0305468 A1 | 12/2010 | Policker et al. |
| 2010/0305656 A1 | 12/2010 | Imran et al. |
| 2011/0034760 A1 | 2/2011 | Brynelsen et al. |
| 2011/0066207 A1 | 3/2011 | Imran |
| 2011/0087076 A1 | 4/2011 | Brynelsen et al. |
| 2011/0166582 A1 | 7/2011 | Syed et al. |

(56) References Cited

U.S. PATENT DOCUMENTS

| | | | |
|---|---|---|---|
| 2011/0207994 A1* | 8/2011 | Burrell et al. | 600/37 |
| 2011/0245598 A1* | 10/2011 | Gertner | 600/37 |
| 2011/0251495 A1 | 10/2011 | Province et al. | |
| 2012/0101874 A1 | 4/2012 | Ben-Haim et al. | |
| 2012/0116182 A1 | 5/2012 | Wong et al. | |
| 2012/0190955 A1 | 7/2012 | Rao et al. | |
| 2012/0214140 A1 | 8/2012 | Brynelsen et al. | |
| 2013/0345771 A1 | 12/2013 | Imran | |
| 2014/0295390 A1 | 10/2014 | Brynelsen et al. | |

FOREIGN PATENT DOCUMENTS

| | | |
|---|---|---|
| AU | 2005286699 A1 | 3/2012 |
| AU | 2010232407 | 2/2015 |
| CA | 2445880 C | 4/2012 |
| CA | 2446128 A1 | 6/2014 |
| CN | 1494451 A | 5/2004 |
| CN | 1522124 A | 8/2004 |
| CN | 102281817 A | 12/2011 |
| CN | 102448365 A | 5/2012 |
| CN | 102448538 A | 5/2012 |
| CN | ZL200580039336.8 | 7/2012 |
| EP | 0 129 483 A1 | 12/1984 |
| EP | 0 442 588 A2 | 8/1991 |
| EP | 0 864 293 A1 | 9/1998 |
| EP | 0 876 808 A1 | 11/1998 |
| EP | 0 571 938 A2 | 4/1999 |
| EP | 1 390 098 A4 | 2/2004 |
| EP | 1 390 100 A4 | 2/2004 |
| EP | 1 793 892 A2 | 6/2007 |
| EP | 1 832 253 A1 | 9/2007 |
| EP | 2 369 990 | 10/2011 |
| EP | 2 413 785 | 2/2012 |
| EP | 2 414 032 | 2/2012 |
| EP | 2 475 296 | 7/2012 |
| JP | 4178105 | 8/2008 |
| WO | 98/43700 A1 | 10/1998 |
| WO | 98/53878 A1 | 12/1998 |
| WO | 00/30534 A1 | 6/2000 |
| WO | 01/58389 A1 | 8/2001 |
| WO | 01/76690 A1 | 10/2001 |
| WO | 02/053093 A | 7/2002 |
| WO | 02/026101 A3 | 8/2002 |
| WO | 02/087657 A2 | 11/2002 |
| WO | 02/089655 A3 | 11/2002 |
| WO | 02/102227 A2 | 12/2002 |
| WO | 2006/034400 A2 | 3/2006 |
| WO | 2006/055365 A2 | 5/2006 |
| WO | 2006/055388 a2 | 5/2006 |
| WO | 2006/083885 A1 | 8/2006 |
| WO | 2007/070906 A2 | 6/2007 |
| WO | 2007/102134 A2 | 9/2007 |
| WO | 2008/005387 A2 | 1/2008 |
| WO | 2008/063486 A2 | 5/2008 |
| WO | 2008/117296 A1 | 10/2008 |
| WO | 2008/139463 A2 | 11/2008 |
| WO | 2009/048380 A1 | 4/2009 |
| WO | 2009/048386 A1 | 4/2009 |
| WO | 2010/068943 A1 | 6/2010 |
| WO | 2010/115194 A1 | 10/2010 |
| WO | 2010/115203 A1 | 10/2010 |
| WO | 2011/032016 A1 | 3/2011 |
| WO | 2012/045030 A2 | 4/2012 |

OTHER PUBLICATIONS

U.S. Appl. No. 60/815,640, filed Jun. 21, 2006 by Imran et al.
U.S. Appl. No. 61/122,315, filed Dec. 12, 2008 by Matthew Hills et al.
U.S. Appl. No. 61/166,636, filed Apr. 3, 2009 by Brynelsen et al.
U.S. Appl. No. 60/337,194, filed Dec. 6, 2001 by Colliou.
Non-Final Office Action for U.S. Appl. No. 10/116,481 mailed Dec. 23, 2003, 8 pages.
Notice of Allowance for U.S. Appl. No. 10/116,481 mailed Jun. 17, 2004, 6 pages.
Non-Final Office Action for U.S. Appl. No. 10/295,115 mailed Jul. 7, 2004, 6 pages.
Non-Final Office Action for U.S. Appl. No. 10/116,481 mailed Sep. 29, 2004, 7 pages.
Final Office Action for U.S. Appl. No. 10/116,481 mailed Mar. 4, 2005, 6 pages.
Non-Final Office Action for U.S. Appl. No. 10/295,115 mailed Apr. 12, 2005, 6 pages.
Final Office Action for U.S. Appl. No. 10/295,115 mailed Sep. 6, 2005, 6 pages.
Notice of Allowance for U.S. Appl. No. 10/295,115 mailed Oct. 13, 2005, 6 pages.
Notice of Allowance for U.S. Appl. No. 10/116,481 mailed Oct. 27, 2005, 7 pages.
Notice of Allowance for U.S. Appl. No. 10/290,788 mailed Nov. 9, 2005, 3 pages.
Supplemental Notice of Allowability for U.S. Appl. No. 10/295,115 mailed Jan. 25, 2006, 2 pages.
Non-Final Office Action for U.S. Appl. No. 10/295,128 mailed Feb. 13, 2006, 9 pages.
Final Office Action for U.S. Appl. No. 10/888,218 mailed Mar. 7, 2007, 6 pages.
Notice of Allowance for U.S. Appl. No. 10/691,880 mailed Jun. 27, 2006, 6 pages.
Non-Final Office Action for U.S. Appl. No. 10/888,218 mailed Aug. 14, 2006, 7 pages.
Non-Final Office Action for U.S. Appl. No. 10/950,345 mailed Oct. 12, 2006, 15 pages.
Non-Final Office Action for U.S. Appl. No. 10/991,648 mailed Nov. 29, 2006, 11 pages.
Advisory Action for U.S. Appl. No. 10/888,218, mailed May 15, 2007, 3 pages.
Final Office Action for U.S. Appl. No. 10/991,648 mailed May 31, 2007, 10 pages.
Notice of Allowance for U.S. Appl. No. 10/888,218 mailed Jul. 26, 2007, 7 pages.
Non-Final Office Action for U.S. Appl. No. 10/295,128 mailed Nov. 26, 2007, 11 pages.
Final Office Action for U.S. Appl. No. 10/950,345 mailed Dec. 26, 2007, 10 pages.
Non-Final Office Action for U.S. Appl. No. 11/256,264 mailed Jan. 9, 2008 13 pages.
Non-Final Office Action for U.S. Appl. No. 11/281,049 mailed Jul. 8, 2008, 7 pages.
Final Office Action for U.S. Appl. No. 10/295,128 mailed Jul. 22, 2008, 12 pages.
Advisory Action for U.S. Appl. No. 10/950,345 mailed Aug. 13, 2008, 3 pages.
Notice of Allowance for U.S. Appl. No. 10/295,128 mailed Nov. 12, 2008, 4 pages.
Non-Final Office Action for U.S. Appl. No. 11/256,264 mailed Dec. 10, 2008, 9 pages.
Non-Final Office Action for U.S. Appl. No. 10/950,345 mailed Feb. 24, 2009, 8 pages.
Final Office Action for U.S. Appl. No. 11/281,049 mailed Apr. 29, 2009, 8 pages.
Final Office Action for U.S. Appl. No. 11/256,264 mailed Jun. 24, 2009, 9 pages.
Notice of Allowance for U.S. Appl. No. 10/950,345 mailed Nov. 30, 2009, 4 pages.
Notice of Allowance for U.S. Appl. No. 11/256,264 mailed Mar. 10, 2010, 6 pages.
Non-Final Office Action for U.S. Appl. No. 12/537,374 mailed Jun. 2, 2010, 8 pages.
Non-Final Office Action for U.S. Appl. No. 11/281,049 mailed Aug. 3, 2010, 8 pages.
Non-Final Office Action for U.S. Appl. No. 12/581,730 mailed Aug. 10, 2010, 7 pages.
Non-Final Office Action for U.S. Appl. No. 12/236,267 mailed Sep. 29, 2010, 8 pages.

(56) References Cited

OTHER PUBLICATIONS

Non-Final Office Action for U.S. Appl. No. 12/435,278 mailed Oct. 10, 2010, 10 pages.
Non-Final Office Action for U.S. Appl. No. 12/370,014 mailed Oct. 21, 2010, 9 pages.
Final Office Action for U.S. Appl. No. 12/537,374 mailed Nov. 15, 2010, 8 pages.
Final Office Action for U.S. Appl. No. 11/281,049 mailed Dec. 22, 2010, 9 pages.
Final Office Action for U.S. Appl. No. 12/581,730 mailed Apr. 27, 2011, 9 pages.
Final Office Action for U.S. Appl. No. 12/370,014 mailed May 5, 2011, 9 pages.
Non Final Office Action for U.S. Appl. No. 12/145,430 mailed Jun. 16, 2011, 29 pages.
Final Office Action for U.S. Appl. No. 12/435,278 mailed Jun. 24, 2011, 8 pages.
Notice of Allowance for U.S. Appl. No. 11/281,049 mailed Jul. 5, 2011, 8 pages.
Non-Final Office Action for U.S. Appl. No. 12/722,979 mailed Sep. 2, 2011, 7 pages.
Non-Final Office Action for U.S. Appl. No. 11/939,490 mailed Oct. 3, 2011, 9 pages.
Non Final Office Action for U.S. Appl. No. 12/795,389 mailed Oct. 4, 2011, 9 pages.
Final Office Action for U.S. Appl. No. 12/145,430 mailed Nov. 7, 2011, 14 pages.
Non-Final Office Action for U.S. Appl. No. 12/537,374 mailed Dec. 21, 2011, 7 pages.
Notice of Allowance for U.S. Appl. No. 12/435,278 mailed Jan. 31, 2012, 8 pages.
Notice of Allowance for U.S. Appl. No. 12/722,979 mailed Apr. 5, 2012, 7 pages.
Notice of Allowance for U.S. Appl. No. 12/537,374 mailed Apr. 12, 2012, 9 pages.
Non-Final Office Action for U.S. Appl. No. 12/754,435 mailed on May 10, 2012, 15 pages.
Final Office Action for U.S. Appl. No. 12/795,389 mailed Jun. 1, 2012, 9 pages.
Final Office Action for U.S. Appl. No. 11/939,490 mailed Jun. 5, 2012, 7 pages.
Notice of Allowance for U.S. Appl. No. 12/581,730 mailed Jun. 21, 2012, 8 pages.
Examiner's Answer to Appeal Brief for U.S. Appl. No. 12/145,430 mailed Jul. 27, 2012, 6 pages.
Notice of Allowance for U.S. Appl. No. 12/236,267 mailed Mar. 29, 2013, 9 pages.
Notice of Allowance for U.S. Appl. No. 12/370,014, mailed May 2, 2013, 6 pages.
Non-Final Office Action for U.S. Appl. No. 12/754,439 mailed on May 8, 2013, 25 pages.
Final Office Action for U.S. Appl. No. 12/754,435 mailed on May 22, 2013, 12 pages.
Non-Final Office Action for U.S. Appl. No. 13/457,961 mailed on Jun. 6, 2013, 7 pages.
Non-Final Office Action for U.S. Appl. No. 13/734,027 mailed Sep. 24, 2013, 5 pages.
Non-Final Office Action for U.S. Appl. No. 12/879,523 mailed Nov. 20, 2013, 19 pages.
Notice of Allowance for U.S. Appl. No. 13/457,961 mailed on Dec. 19, 2013, 8 pages.
Final Office Action for U.S. Appl. No. 12/879,523 mailed Jun. 4, 2014, 17 pages.
Notice of Allowance for U.S. Appl. No. 13/250,757 mailed on Sep. 8, 2014, 7 pages.
Notice of Allowance for U.S. Appl. No. 13/250,757 mailed on Oct. 30, 2014, 2 pages.
Non-Final Office Action for U.S. Appl. No. 12/879,523 mailed Dec. 17, 2014, 14 pages.

Physical Activity Guidelines Advisory Committee. Physical Activity Guidelines Advisory Committee Report, 2008. Washington, DC: U.S. Department of Health and Human Services, 2008, 683 pages.
Bellahsene, et al., "Evaluation of a Portable Gastric Stimulator," Ninth Annual Conference of the Engineering in Medicine and Biology Society, 2 pages total. (1987).
Bouten et al., "Assessment of energy expenditure for physical activity using a triaxial accelerometer", Med Sci Sports Exerc. Dec. 1994; 26(12):1516-23.
Bouten, "A Triaxial Accelerometer and Portable Data Processing Unit for the Assessment of Daily Physical Activity", IEEE Transactions on Biomedical Engineering Mar. 1997; 44(3):136-147.
Brage et al., "Branched equation modeling of simultaneous accelerometry and heart rate monitoring improves estimate of directly measured physical activity energy expenditure," J Appl Physiol, Jan. 2004; 96(1):343-351; retrieved from the Internet: <http://jap.physiolo w.orQ/content/96/1/343.full.pdf+html>.
Brage et al., "Reliability and validity of the combined heart rate and movement sensor Actiheart," Eur J Clin Nutr. Apr. 2005;59(4):561-70.; retrieved from the Internet: <http://www.nature.com/ejcn/journal/v59/n4/pdf/1602118a.pdf>.
Ceesay et al., "The use of heart rate monitoring in the estimation of energy expenditure: a validation study using indirect whole-body calorimetry," Br J Nutr, Br J Nutr. Mar. 1989;61(2):175-86.
Chen et al., "Improving energy expenditure estimation by using a triaxial accelerometer," J Appl Physiol. Dec. 1997;83(6):2112-22; retrieved from the Internet: <http:1/jap.physiology.org/content/83/6/2112.full.pdf+html>.
Cigaina et al., "Gastric Myo-Electrical Pacing as Therapy for Morbid Obesity: Preliminary Results," Obes Surg;9:333-334, (1999).
Grouter et al., "A New 2-Regression Model for the Actical Accelerometer," Br J Sports Med. Mar. 2008;42(3):217-24. Epub Aug. 30, 2007.
Grouter et al., "Accuracy of the Actiheart for the Assessment of Energy Expenditure in Adults," Eur J Clin Nutr, 2008; 62(6):704-11.
Daniel et al., "Electrical Activity of the Gastrointestinal Tract as an Indication of Mechanical Activity," Am. J. of Digestive Diseases, 8(1):54-102, (1963).
Eagon et al., "Effects of Gastric Pacing on Canine Gastric Motility and Emptying," The American Physiological Society, 265(4):G767-G774, (Oct. 1993).
Eagon et al., "Gastrointestinal Pacing, Surgical Clinics of North America," 73(6):1161-1172 (Dec. 1993).
Electric Stimulation of the Gastrointestinal Tract, GP, p. 151 (Apr. 1964), 1 page.
English Translation of Notification of the First Office Action for corresponding Chinese Patent Application No. 201080022864.3 dated Jul. 31, 2013, 5 pages.
English Translation of Notification of the Second Office Action for corresponding Chinese Patent Application No. 201080022864.3 dated Mar. 12, 2014, 10 pages.
English Translation of Notification of the Third Office Action for corresponding Chinese Patent Application No. 201080022864.3 dated Sep. 23, 2014, 16 pages.
Extended European Search Report for corresponding European Patent Application No. 10759546.4 dated Nov. 6, 2014, 9 pages.
Familoni, "Efficacy of Electrical Stimulation at Frequencies Higher Than Basal Rate in Canine Stomach," Digestive Diseases and Sciences, 42(5):892-897, (May 1997).
Familoni, et al., "Electrical Pacing of the Stomach in Dogs, Engineering in Medicine and Biology Society," IEEE Proceedings of the Annual International Conference, 6:2315-2316 (Oct. 29-Nov. 1, 1992).
Geldof et al., "Electrogastrographic Study of Gastric Myoelectrical Activity in Patients With Unexplained Nausea and Vomiting," Gut, 27:799808, (1986).
Hocking, "Postoperative Gastroparesis and Tachygastria Response to Electric Stimulation and Erythromycin," Surgery, 114(3):538-542 (Sep. 1993).
Hughes et al., "BALANCE (Bioengineering Approaches for Lifestyle Activity and Nutrition Continuous Engagement): develop-

(56) References Cited

OTHER PUBLICATIONS ing New Technology for Monitoring Energy Balance in Real Time", Journal of Diabetes Science and Technology, vol. 4, Issue 2, Mar. 2010, pp. 429-434.
International Preliminary Report on Patentability for PCT Application No. PCT/US2010/029987 issued Oct. 4, 2011, 18 pages.
International Search Report and Written Opinion of PCT Application No. PCT/US08/6845, mailed Sep. 15, 2008, 9 pages.
Jakicic et al. [Abstract], "Evaluation of the SenseWear Pro Armband to assess energy expenditure during exercise," Med Sci Sports Exerc. May 2004;36(5):897-904.
Jette, M. "Metabolic Equivalents (METS) in Exercise Testing, Exercise Prescription, and Evaluation of Functional Capacity" Clin. Cardiol. 13, 555-565 (1990).
Joshi et al., "Anesthesia for Laparoscopic Surgery," Canadian Journal of Anesthesia 49(6):R1-R5 (2002).
Kelly et al., "Role of the Gastric Pacesetter Potential Defined by Electrical Pacing," Canadian J. of Physiology and Pharmacology, 50:1017-1019, (1972).
Kelly, Differential Responses of the Canine Gastric Corpus and Antrum to Electric Stimulation, Am. J. of Physiology. 226(1):230-234, (Jan. 1974).
Kelly, et al., "Pacing the Canine Stomach With Electric Stimulation," Am. J. of Physiology, 222(3):588-594 (Mar. 1972).
Kim et al., "Detection of subjects with higher self-reporting stress scores using heart rate variability patterns during the day," Conf Proc IEEE Eng Med Bioi Soc. 2008;2008:682-5.
Kubota, et al., "Manometric Evaluation of Children With Chronic Constipation Using a Suction-Stimulating Electrode," Eur. J. Pediari. Surg. 2:287-290, (1992).
Meyers et al., "Near-infrared Spectroscopy in Food Analysis", Encyclopedia of Analytical Chemistry, ISBN 0471976709.
Miedema et al., "Pacing the Human Stomach," Surgery, 143-150, (Feb. 1992).
Notification of Transmittal of the International Search Report and the Written Opinion of the International Searching Authority, or the Declaration and International Search Report and Written Opinion of the International Searching Authority for International Application No. PCT/US2010/029987 mailed on Jun. 1, 2010, 14 pages.
Notification of Transmittal of the International Search Report and the Written Opinion of the International Searching Authority, or the Declaration and International Search Report and Written Opinion of the International Searching Authority for International Application No. PCT/US2010/029969 mailed on Jul. 28, 2010, 10 pages.
Patent Examination Report No. 1 for corresponding Australian Patent Application No. 2010232407 dated Apr. 16, 2014, 5 pages.
Patent Examination Report No. 1 for corresponding Australian Patent Application No. 2010232407 dated Feb. 21, 2014, 4 pages.
Patent Examination Report No. 2 for corresponding Australian Patent Application No. 2010232398 dated Oct. 17, 2014, 5 pages.
Sarna et al., "Electrical Stimulation of Gastric Electrical Control Activity," Am. 1. of Physiology, 225(1):125-131, (Jul. 1973).
Sarna, et al., "Gastric Pacemakers," Gastroenterology. 70:226-231, (1976).
Swain, et al., "An Endoscopically Deliverable Tissue-Transfixing Device for Securing Biosensors in the Gastrointestinal Tract," Gastrointestinal Endoscopy, 40(6):730-734 (1994).
Third Office Action for corresponding Chinese Patent Application No. 201080022872.8 dated Oct. 20, 2014, 3 pages. (English translation is not available).
Levine et al., "Interindividual variation in posture allocation: possible role in human obesity," Science, Jan. 28, 2005;307(5709):584-6.6.
MacWilliam, "Postural Effects on Heart-Rate and Blood-Pressure," Exp Physiol, Aug. 1933, 23:1-33; retreived from the Internet; <http://ep.physoc.org/content/23/1/1.full.pdf+html>.
McCrory et al., "Between-day and within-day variability in the relation between heart rate and oxygen consumption: effect on the estimation of energy expenditure by heart-rate monitoring," Am J Clin Nutr. Jul. 1997;66(1):18-25.

Moon et al., "Combined heart rate and activity improve estimates of oxygen consumption and carbon dioxide production rates," J Appl Physiol. Oct. 1996;81(4):1754-61.
Papazoglou et al., "Evaluation of a multisensor armband in estimating energy expenditure in obese individuals," Obesity (Silver Spring). Dec. 2006;14(12):2217-23.
Pate et al., "Physical activity and public health. A recommendation from the Centers for Disease Control and Prevention and the American College of Sports Medicine," JAMA. Feb. 1, 1995;273(5):402-7.
Plasqui et al., "Measuring free-living energy expenditure and physical activity with triaxial accelerometry," Obes Res. Aug. 2005;13(8):1363-9.
Schutz et al., "A new accelerometric method to assess the daily walking practice," Int J Obes Relat Metab Disord Jan. 2002; 26(1):111-8; retreived from the Internet: <http://www.nature.com/ijo/journallv26/n1/pdf/0801856a.pdf>.
Schutz et al., "Diet-Induced Thermogenesis Measured Over a Whole Day in Obese andNonobese Women," Am J Clin Nutr. Sep. 1984;40(3):542-52.
St-Onge et al., "Evaluation of a portable device to measure daily energy expenditure in free-living adults," Am J Clin Nutr, May 2007; 85(3):742-9.
Strath et al. [Abstract], "Simultaneous heart rate-motion sensor technique to estimate energy expenditure," Med Sci Sports Exerc. Dec. 2001;33(12):2118-23.
Strath et al., "Evaluation of heart rate as a method for assessing moderate intensity physical activity," Med Sci Sports Exerc. Sep. 2000;32(9 Suppi):S465-70.
Strath et al., "Validity of the simultaneous heart rate-motion sensor technique for measuring energy expenditure," Med Sci Sports Exerc. May 2002;34(5):888-94.
Treuth et al., "Energy expenditure in children predicted from heart rate and activity calibrated against respiration calorimetry," Am J Physiol. Jul. 1998;275(1 Pt 1):E12-8.
Yoshiuchi et al. [Abstract], "Yearlong physical activity and depressive symptoms in older Japanese adults: cross-sectional data from the Nakanojo study," Am J Geriatr Psychiatry. Jul. 2006;14(7):621-4.
International Search Report and Written Opinion of PCT Application No. PCT/US2010/048497, mailed Nov. 5, 2010, 11 pages.
International Search Report and Written Opinion for PCT Application No. PCT/US2009/067869, mailed Apr. 14, 2010, 6 pages.
Familoni, Babajide O., Efficiency of Electrical Stimulation at Frequencies Higher Than Basal Rate in Canine Stomach, Digestive Diseases and Sciences, 42/5:892-897, (May 1997).
You et al., "Electrogastrographic Study of Patients With Unexplained Nausea, Bloating and Vomiting", Gastroenterology, 79:311-314, (1980).
Notification of Transmittal of the International Search Report and the Written Opinion of the International Searching Authority, or the Declaration and International Search Report and Written Opinion of the International Searching Authority for International Application No. PCT/US2011/054402 mailed on Jun. 13, 2012, 23 pages.
International Search Report and Written Opinion of PCT Application No. PCT/US05/40561 mailed Nov. 8, 2007, 11 pages.
Medtronic Education Brief (US and Europe) Jul. 2007 / NEB 07-04, © Medtronic, Inc., 710 Medtronic Parkway NE, Minneapolis, MN 55432-5604, USA.
Extended European Search Report for corresponding European Patent Application No. 05798863.6 dated May 15, 2012, 10 pages.
English Translation and Second Office Action for corresponding Chinese Patent Application No. 200580039336.8 dated Jun. 21, 2011, 7 pages.
Examiner's Report No. 3 for corresponding Australian Patent Application No. 2005286699 dated Sep. 19, 2011, 2 pages.
Patent Examination Report No. 1 for corresponding Australian Patent Application No. 2009324421 dated Dec. 18, 2014, 2 pages.
Supplementary European Search Report for corresponding European Patent Application No. 10816189.4 dated Aug. 22, 2013, 8 pages.
Communication pursuant to Article 94(3) EPC for corresponding European Patent Application No. 10816189.4 dated May 9, 2014, 4 pages.

\* cited by examiner

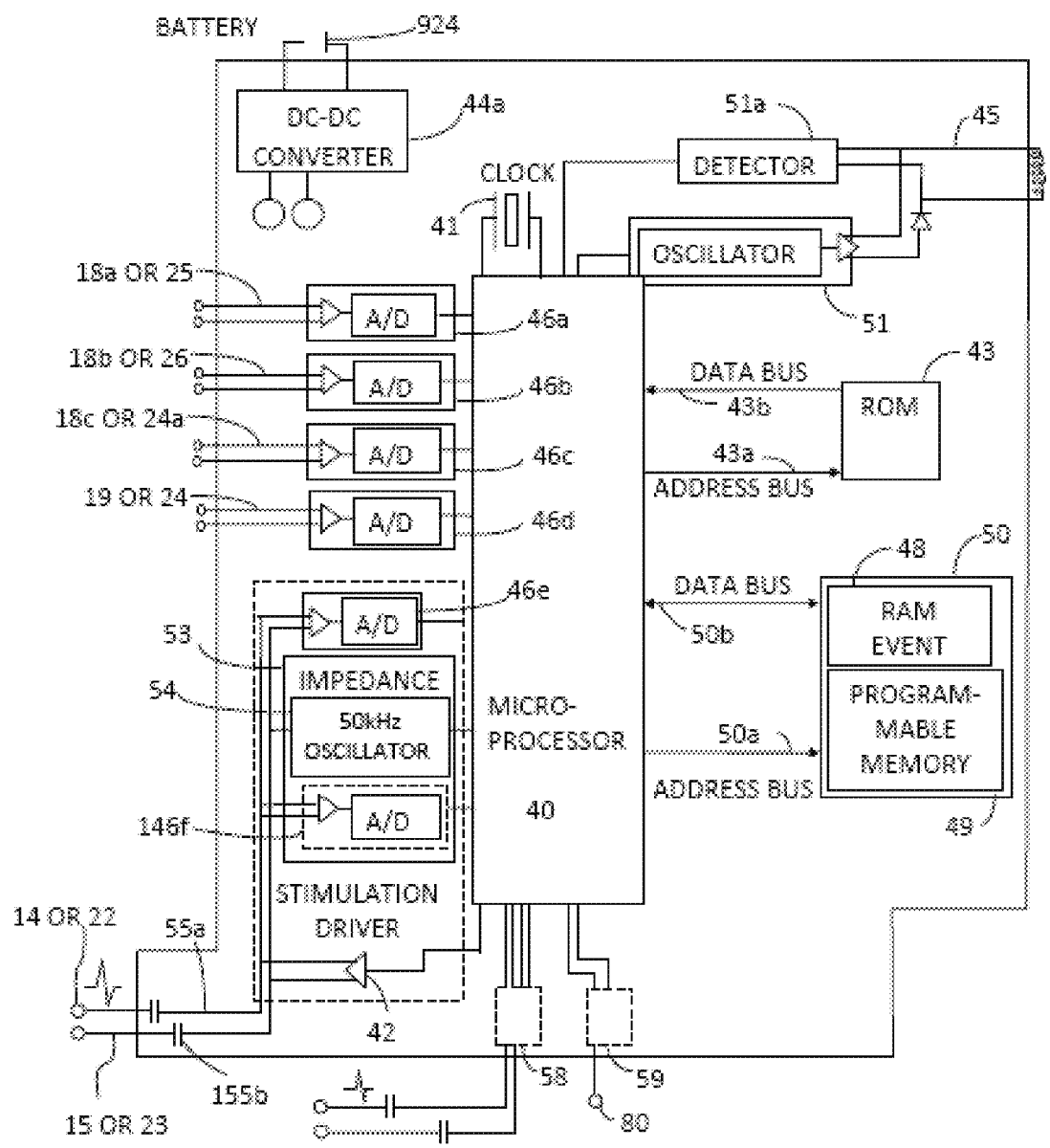

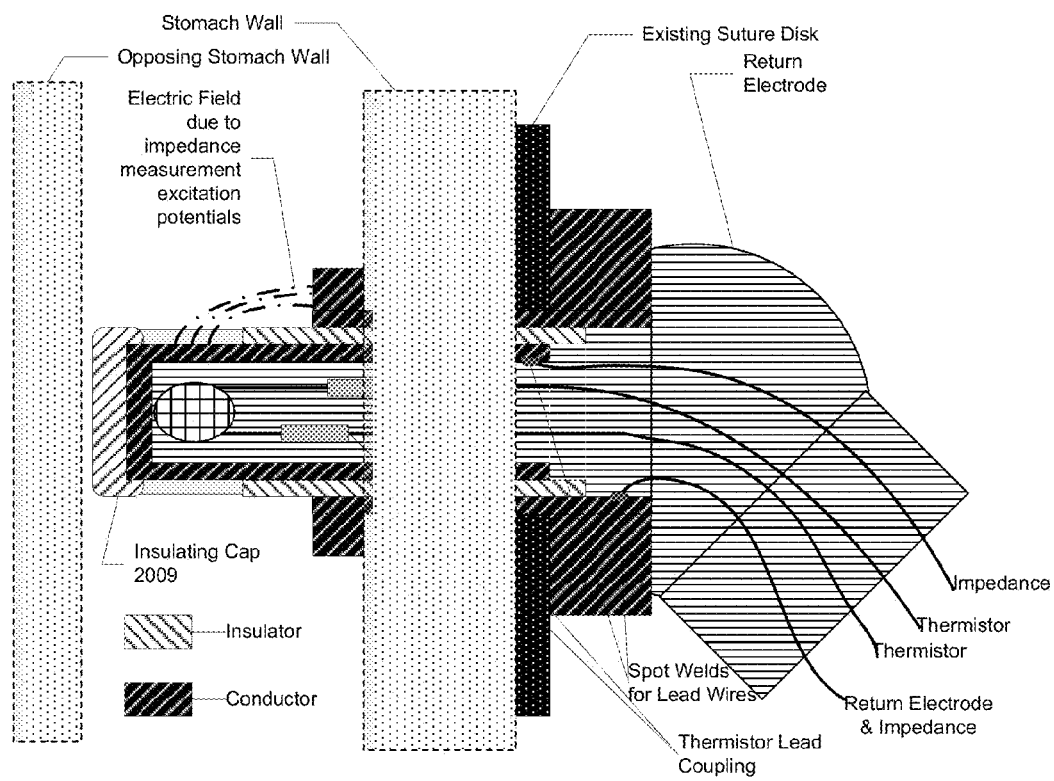
FIG. 2G1

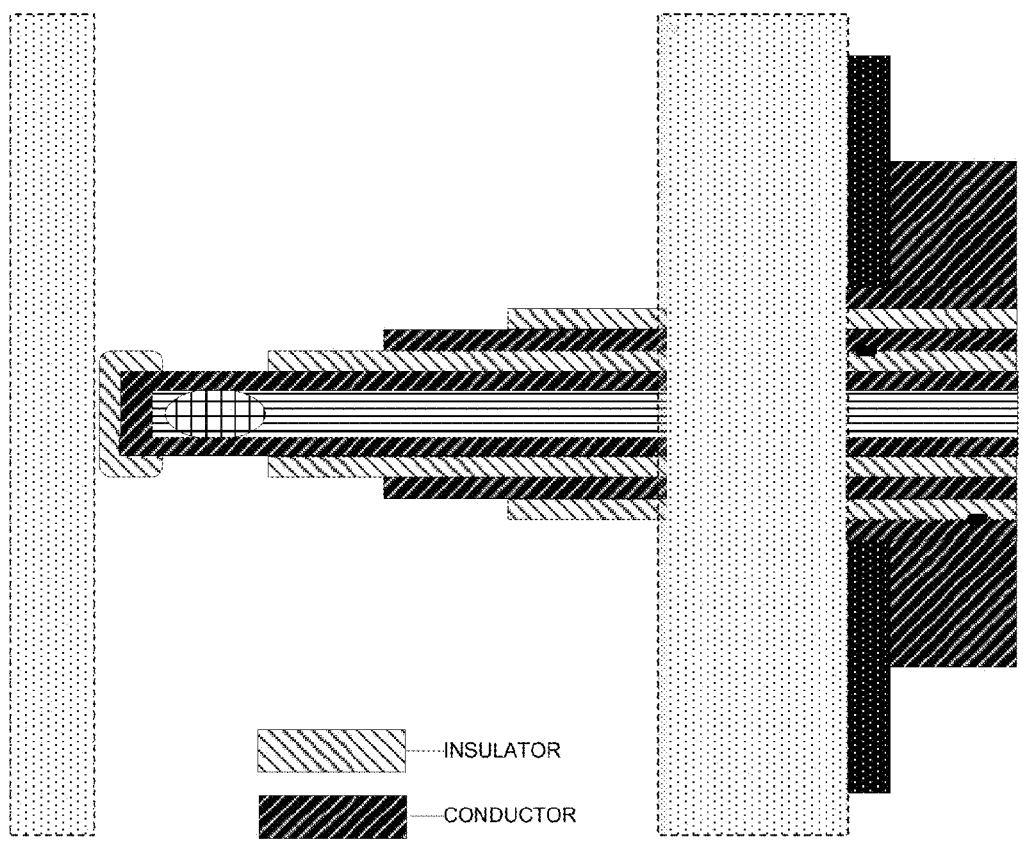
FIG. 2G2

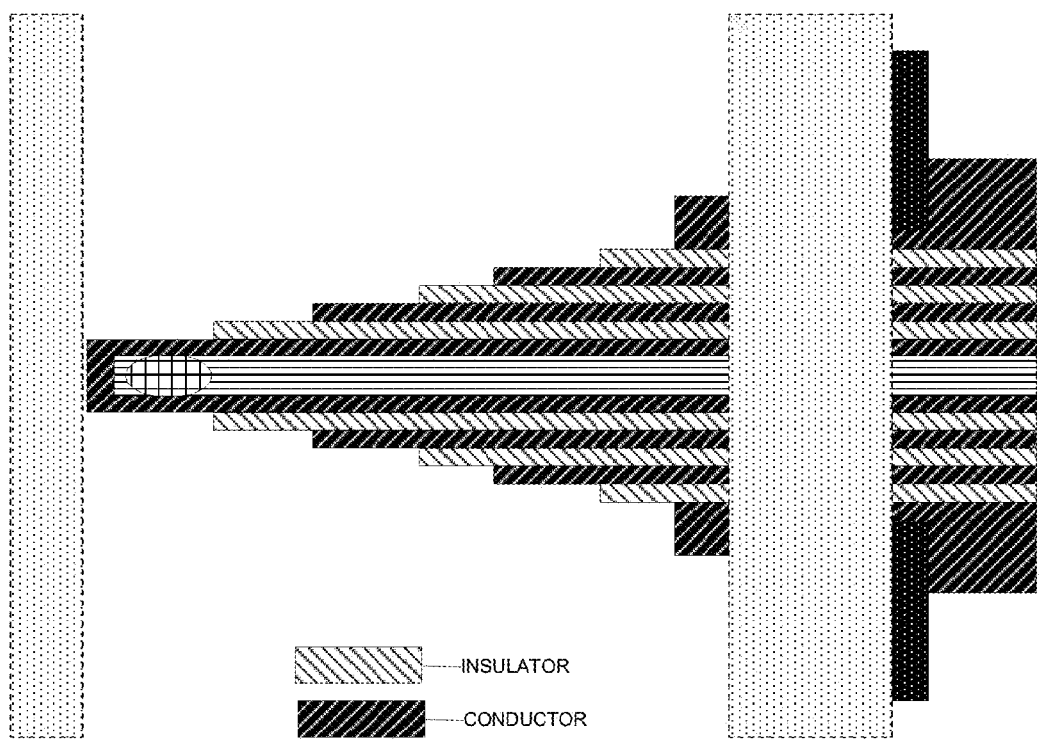
FIG. 2G3

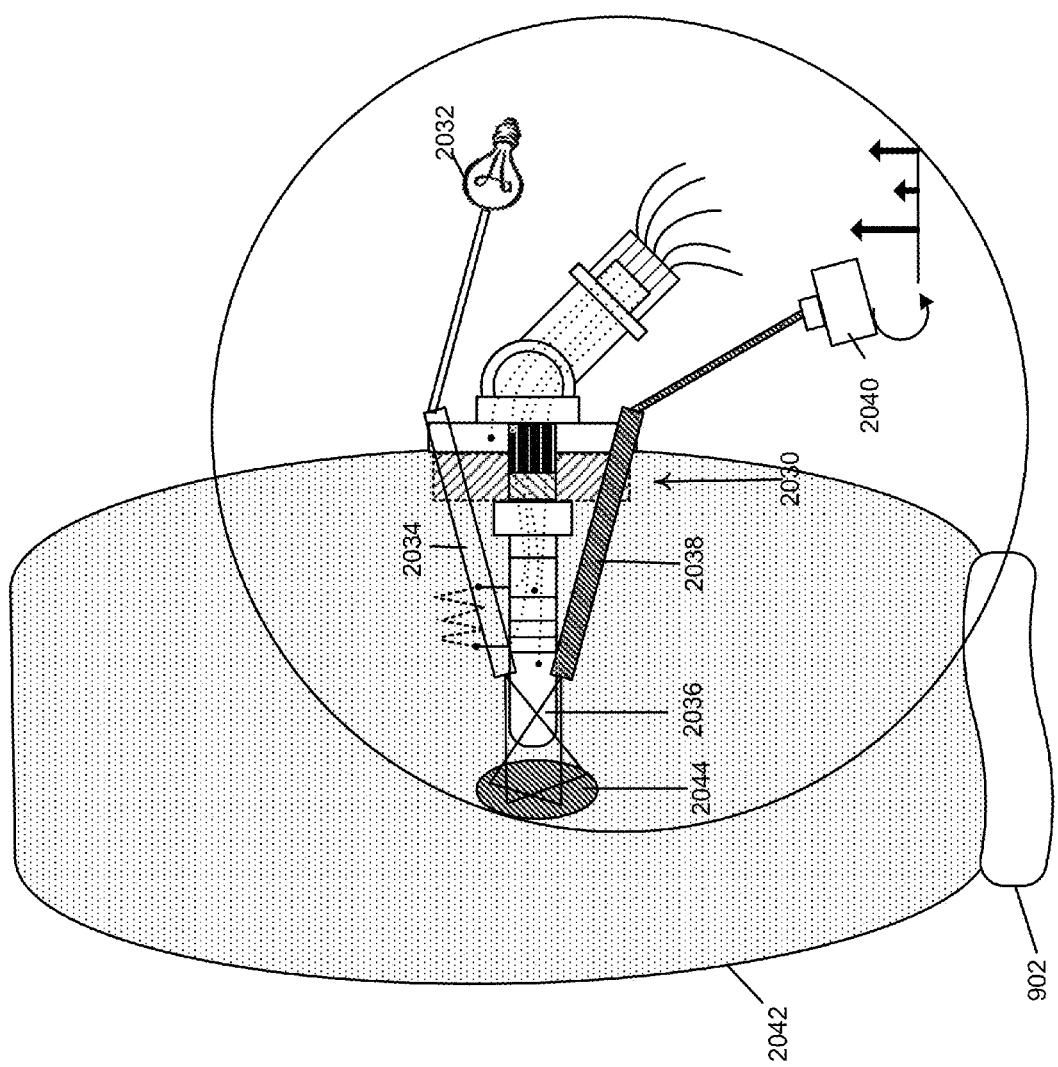

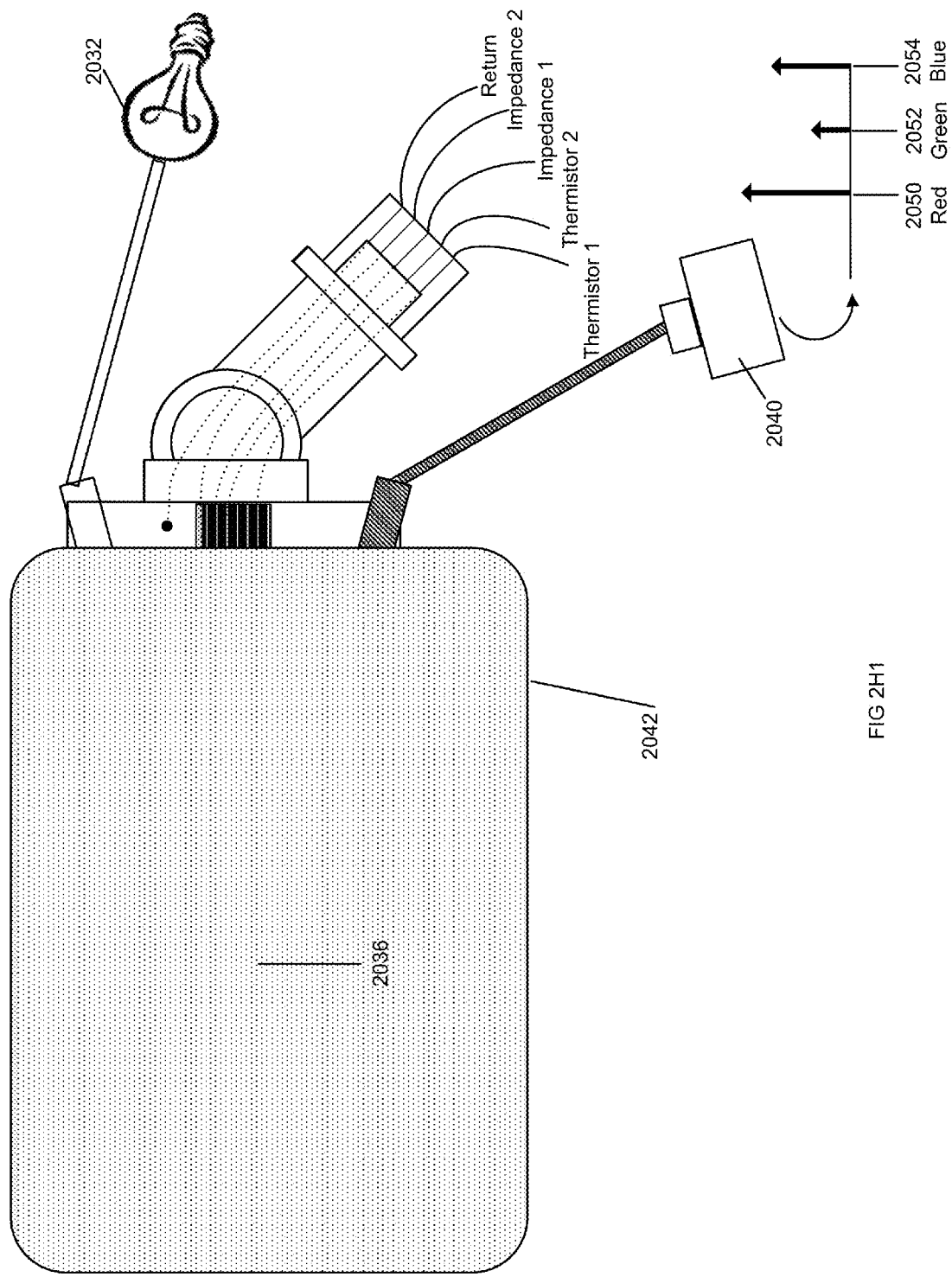

FEEDBACK SYSTEMS AND METHODS TO ENHANCE OBSTRUCTIVE AND OTHER OBESITY TREATMENTS, OPTIONALLY USING MULTIPLE SENSORS

CROSS-REFERENCE TO RELATED APPLICATIONS

The present application claims the benefit under 35 USC 119(e) of U.S. application Ser. No. 13/250,757 filed Sep. 30, 2011, now issued as U.S. Pat. No. 8,934,976, entitled "Feedback Systems and Methods to Enhance Obstructive and Other Obesity Treatments, Optionally Using Multiple Sensors" and also Provisional Application No. 61/388,900 filed Oct. 1, 2010, entitled "Feedback Systems and Methods to Enhance Obstructive and Other Obesity Treatments"; the full disclosures of which are incorporated herein by reference in their entirety. The subject matter of the present application is related to that of Application No. 61/166,636 filed Apr. 3, 2009, entitled "Feedback Systems and Methods for Communicating Diagnostic and/or Treatment Signals to Enhance Obesity Treatments"; U.S. application Ser. No. 12/145,430 filed Jun. 24, 2008, entitled "Sensor Driven Gastric Stimulation for Patient Management"; U.S. application Ser. No. 10/950,345 filed Sep. 23, 2004, entitled Responsive Gastric Stimulator"; U.S. Application No. 61/122,315 filed Dec. 12, 2008, entitled "Detection of Food or Drink Consumption in Order to Control Therapy or Provide Diagnostics"; U.S. application Ser. No. 12/637,452 filed Dec. 14, 2009, entitled "Detection of Food or Drink Consumption In Order to Control Therapy or Provide Diagnostics", and U.S. application Ser. Nos. 12/754,435 and 12/754,439, both filed Apr. 5, 2010 and entitled "Feedback Systems and Methods for Communicating Diagnostic and/or Treatment Signals to Enhance Obesity Treatments," and "Feedback Systems and Methods to Enhance Obstructive and Other Obesity Treatments", respectively the full disclosures of each of which are also incorporated herein by reference in their entirety.

BACKGROUND OF THE INVENTION

Since the mid-seventies, the prevalence of obesity has increased sharply for both adults and children. These increasing rates raise concern because of their implications for Americans' health. Being overweight or obese may increase the risk of many diseases and health conditions, including: hypertension, dyslipidemia (for example, high total cholesterol or high levels of triglycerides), type 2 diabetes, coronary heart disease, stroke, gallbladder disease, osteoarthritis, sleep apnea and respiratory problems, and some cancers (such as endometrial, breast, and colon).

Obesity and its associated health problems have a significant economic impact on the U.S. health care system. Medical costs associated with excess weight and obesity may involve direct and indirect costs. Direct medical costs may include preventive, diagnostic, and treatment services related to obesity. Indirect costs relate to morbidity and mortality costs. Morbidity costs are defined as the value of income lost from decreased productivity, restricted activity, absenteeism, and bed days. Mortality costs are the value of future income lost by premature death.

Many therapies are currently being investigated for treatment of obesity and diseases associated with obesity. To date, the widely used obesity treatments have not been shown to be ideal, particularly for those afflicted with severe obesity. The approaches that have been proposed range from lifestyle coaching to major surgical therapies.

Many severely obese patients have turned to surgical options. These surgical options include highly invasive procedures such as stomach reduction and gastric bypass, while less invasive procedures include the implantation of gastric bands. Another option for the severely obese patients involves the endoscopic placement of an intragastric balloon, a silicon balloon device that is placed in the stomach endoscopically.

Unfortunately, patient compliance and the accuracy with which patients report their own activities can significantly limit the effectiveness of weight loss treatments. One of the problems associated with the surgical procedures of gastric reduction, gastric bypass, gastric banding and intragastric balloons revolves around patient compliance. Even after these surgeries or endoscopic procedures, a number of patients find ways to "cheat;" they avoid the volume limitation imposed by stomach reduction from the above-mentioned procedures simply by ingesting liquids or liquefied solids that easily drain into their small intestines. For weight loss treatment to be successful, the surgical or endoscopic procedures should ideally be combined with lifestyle changes. Patients' self-reporting has very often proven to be inaccurate.

Therefore, it would be desirable to provide devices, systems and methods that can accurately monitor and report a patient's actual daily caloric intake as well as activity related caloric expenditure, to be used in obesity treatment therapy. Ideally, such a system would provide a patient, his or her physician, a lifestyle coach, support group, and/or other caregivers the information collected about the patient's eating and exercise habits for use in monitoring the patient's progress and so as to present actual behavior-based information to the patient for effective behavior modification and greater success in achieving weight loss or health goals.

BRIEF SUMMARY OF THE INVENTION

The present invention relates to feedback systems and methods to enhance obstructive and other obesity treatments. Although embodiments of the invention make specific reference to treatment of obesity, the system and methods described herein may be applicable to other treatments seeking patient behavior modification, and particularly disorders in which presenting feedback regarding patients' actual eating and/or exercise habits is desired.

In a first aspect, the invention provides a therapeutic implant system for treating a patient. The patient will typically have a gastrointestinal tract and an unhealthy ingestion pattern. The therapeutic implant system will comprise an ingestion restricting implant body deployable along the gastrointestinal tract so as to separate the gastrointestinal tract into a restricted portion of the gastrointestinal tract and a gastric pouch portion of the gastrointestinal tract upstream of the restricted portion. The implant body will include a gastric band defining a channel therethrough, the gastrointestinal tract extendable through the channel of the implant body, wherein the gastric band comprises a fluid-filled pressure bladder disposed between the channel and a support structure such that changes in a fluid pressure within the fluid pressure bladder correspond with changes in an engagement force between the gastrointestinal tract and the gastric band. A sensor will be coupleable to the gastric pouch portion of the gastrointestinal pouch so that signals are generated in response to transient changes in the gastric pouch and the signals indicate an ingestion event. A processor will be coupled to the signal generator and the implant body such that, in response to the signals, the unhealthy ingestion pattern by the patient is inhibited in use sufficiently to modify the unhealthy ingestion pattern toward a healthier ingestion pattern.

In many embodiments, a display will be coupled to the processor. The display can show eating events identified in response to the signals during a plurality of days. The display can be configured for communicating to the patient and/or a lifestyle coach of the patient. An actuator may be coupled to the processor so as to alter the fluid pressure within the bladder in response to the ingestion event. In some embodiments, at least two electrodes will be coupled to the processor so as to stimulate tissue of the gastrointestinal tract in response to the ingestion event. In exemplary embodiments, at least one of a pressure sensor, a temperature sensor, an optical sensor, an impedance sensor, a pH sensor, or an acoustic sensor will be coupled to the processor. The optical sensor may include a visible color sensor and/or an infrared light sensor.

Some of the sensor signals can be transmitted from the bladder to the processor, and the altering of the engagement force may be induced by an actuator so that the pressure within the bladder is decreased each day to allow healthy ingestion and increased each day to inhibit unhealthy ingestion. Energizing the actuator may optionally activate the gastric band so as to increase restriction and decrease ingestion into the patient. In other embodiments, energizing the actuator deactivates the gastric band so as to decrease restriction and allow increased ingestion into the patient.

The sensor may be included in a transgastric probe having a probe body with a transgastric wall traversing portion. The sensor can be separated along the probe body from the wall traversing portion so as to be disposed within an interior of the transgastric pouch. The transgastric probe may include two or more members selected from the group consisting of a temperature sensor, an electrode, and a visible color sensor and/or an infrared light detector.

Two or more electrodes may be coupled to the processor, optionally so as to deliver electrical stimulation to the gastrointestinal tract and/or another internal organ. The electrodes may be used as sensors, and/or may be mounted along the channel of the implant body or on a transgastric probe body or both. Two sensors may be coupled to the processor and used to generate signals, and the processor may be configured to process the signals so as to identify transient changes in the gastric pouch portion of the gastrointestinal tract.

In some embodiments, a temperature sensor can be coupled to the processor so as to provide a temperature from within the gastric pouch portion of the gastrointestinal tract. Optionally, the sensor may comprise a visible color sensor and/or an infrared light detector.

In another aspect, the invention provides a system for treating a patient having a gastrointestinal tract. The system comprises an ingestion restricting implant body deployable along the gastrointestinal tract. At least two sensors transmit signals in response to ingestion into the patient in use. A processor is coupled to the at least two sensors. The processor, in response to the signals, generates ingestion display signals or patient treatment signals or both.

In another aspect, the invention provides a therapeutic implant system for treating a patient having a gastrointestinal tract and an unhealthy ingestion pattern. The therapeutic implant system comprises an ingestion restricting implant body implantable along the gastrointestinal tract so as to separate the gastrointestinal tract into a restricted portion of the gastrointestinal tract and gastric pouch portion of the gastrointestinal tract upstream of the restricted portion. A sensor is configured to engage the gastric pouch portion, and a processor is coupleable to the sensor so as to transmit signals therebetween. The signals are transmitted in correlation with transient changes in the gastric pouch portion of the gastrointestinal tract in use.

The implant body may have a first configuration and a second configuration, the size, compliance, or shape of the implant body in the second configuration being different than the size, compliance, or shape of the implant body in the first configuration such that the implant body has an enhanced inhibition of ingestion in the second configuration.

In another aspect, the invention provides a therapeutic implant for treating a patient having a gastrointestinal tract and an unhealthy ingestion pattern. The therapeutic implant comprises an ingestion restricting implant body implantable along the gastrointestinal tract, and at least two sensors for generating signals. A processor is coupled to the at least two sensors and the implant body so as to transmit the signals therebetween. The signals will be transmitted in correlation with an ingestion event.

In yet another aspect, the invention provides a method for treating a patient having a gastrointestinal tract. The method comprises deploying at least a portion of an implant along the gastrointestinal tract. The implant has a body, at least three sensors and a processor. During a day, and in response to signals sent from the sensors to the processor, a candidate characterization of an ingested material is identified. It is determined whether the ingested material constitutes an allowed ingestion in response to the candidate characterization, and if so, the ingested material is allowed to traverse the body of the implant along the gastrointestinal tract. It is also determined whether the ingested material constitutes an unhealthy ingestion in response to the candidate characterization, and if so, signals are transmitted from the processor to the body so as to alter a shape, compliance, and/or size of the body such that the body restricts the unhealthy ingestion.

In a final aspect, the invention provides transgastric probe comprising a probe body having a transgastric wall traversing portion and a gastric cavity portion. The gastric wall traversing portion is configured for extending through a gastric wall of a gastrointestinal tract of a patient so as to support the gastric cavity portion within a gastric cavity. A plurality of sensors are mounted to the probe body. At least one of the sensors is disposed along the gastric cavity portion of the probe body so as to be disposed within an interior of the gastric cavity when the probe body is implanted. The sensors include two or more members selected from the group consisting of a temperature sensor, an electrode, and a visible color sensor and/or an infrared light detector.

BRIEF DESCRIPTION OF THE DRAWINGS

FIG. 1B-1D illustrate the electrical stimulation component of the gastric band sensor system implant 900.

FIGS. 2G1-2G3 show alternative embodiments of the multifunctional transgastric probe.

FIGS. 2H and 2H1 show an alternative embodiment of the multifunctional transgastric probe which also comprises a color sensor at the distal end of the probe.

FIG. 2I shows a schematic configuration of a color sensor in a multifunctional transgastric probe when the gastric pouch is largely empty; the color intensities measured by the photodiodes reflect the color of the gastric pouch cavity.

FIG. 3 illustrates ingestion of food or drink into a stomach.

FIG. 4A shows the expected pressure waveforms from an ingestion of food 1000. FIG. 4B illustrates an overeating event. FIG. 4C shows the expected pressure waveforms 1200 from a drinking event.

DETAILED DESCRIPTION OF THE INVENTION

Figure 1:
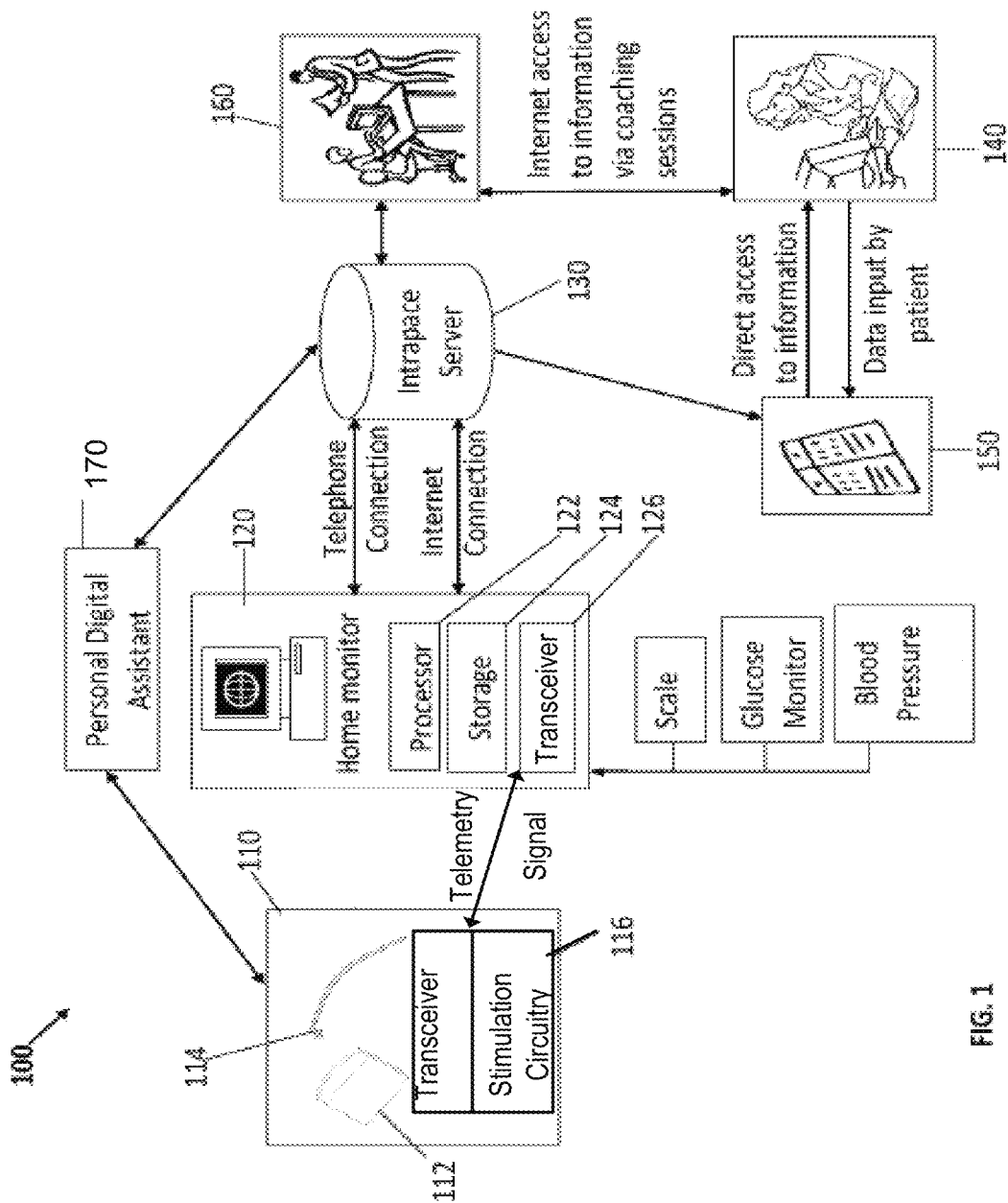
FIG. 1 shows an exemplary system 100 suitable for implementation of embodiments of the present invention.

The present invention often takes advantage of processors to enhance obesity therapies that rely on restrictive implants disposed along the gastrointestinal tract. Some embodiments of the present invention relate to feedback systems and methods for communicating implanted sensor-based information so as to affect behavior modification for eating disorders. Some embodiments of the present invention employ systems which alter a restrictive implant in response to signals. Although embodiments of the invention make specific reference to treatment for obesity, the system and methods described herein may be applicable to any treatment in which presenting feedback regarding patients' eating and/or exercise habits is desired.

Embodiments of the present invention collect information regarding the patient's eating and exercise habits via one or more sensors implanted within the body of the patient. This information can then be reviewed by a clinician during office visits and used in coaching the patient. Coaching may include helping the patient to make healthy lifestyle choices, such as specifically encouraging the patient to decrease his or her caloric intake while increasing his or her caloric expenditure. Compliance with physician advice may be low in obese patients and caloric intake is often under-reported while caloric expenditures are often over-reported. Although eventually weight gain or loss by a patient will indicate the accuracy of the patient's reporting, the objective monitoring systems provided herein will significantly improve many patients' ability to acknowledge their actual behavior, to identify elements of their behavior that can be changed to improve health, and to effect incremental changes toward achieving long-term health goals. The implantable sensors will often detect eating events, solid versus liquid intake, and optionally even meal compositions. The various implantable sensors can be implanted at the same time as the surgical procedures so as to minimize the number of surgical or endoscopic interventions in the patients. The systems and methods described herein may identify eating and other behaviors which the patient is not aware of (including night-time eating and the like). These systems and methods may also improve the correlation between positive patient behavior and beneficial positive reinforcement, and decrease deleterious correlations between negative patient behavior (such as under-reporting of actual ingestion, over-reporting activity levels, and the like) with misguided positive reinforcement. Such improvements may be particularly effective at promoting and/or maintaining healthy activities when ultimate health goals remain distant.

The sensor and feedback system of the present invention is not subject to the reporting bias of the patient, thus presenting an objective view. In addition, embodiments of the present invention allow data to be collected twenty-four hours per day, seven days per week, which provides an accurate record of the patient's behavior without dependence upon the patient's memory or commitment to the eating and exercise tracking process. Some embodiments may sense and/or restrict caloric intake, such as using a band implanted around the stomach so as to constrict flow along the gastrointestinal tract, a gastric balloon inflated within the stomach, or the like. In still other embodiments, the present invention also provides stimulation of the stomach to reduce caloric intake.

Embodiments of the invention provide a system that stores the data collected by the implanted system remotely. The system is then made accessible by the patients and/or the patients' health coaches to support the patient in achieving their weight reduction goals. The automated availability of behavior modification feedback, shortened time between "coaching sessions" and increased accuracy of the sensor data will improve outcomes for the patients.

In some embodiments, the invention may employ aspects of social networking systems, with sensor-based information that has been generated using signals from an implanted sensor often being available to one or more members of a group. The group may, at least in part, be defined by the patient giving permission to particular individuals. Other members of the group (such as the patient and a supervising physician) may be defined when the group is first organized. Many patients having implanted sensors may join a mutual support group of patients, with sensor-based data being shared between the implant recipients. Advantageously, these systems may allow patients to receive feedback within a relatively short time after exhibiting behavior that is sensed by the sensor, preferably within two days of the sensor identifying an eating event or activity level, and ideally within one day of the behavior. Using telemetry-based communication between the implanted device and a home monitor (or other intermediate device), some embodiments may allow daily uploads, and/or send messages to a cell phone/Smart phone or personal digital assistant (PDA) in near real time. This significant shortening of the time delay between patient behavior and relationship-based feedback to the patient may provide significant advantages over feedback provided through monthly, quarterly, or annual appointments with a dietician or physician. Nonetheless, communication enhancement described herein may provide efficacy benefits for alternative embodiments that rely on uploading of patient data during such routine appointments.

To facilitate the relationships employed for implant patient feedback, embodiments of the invention may make use of aspects of Web-2.0 systems such as Facebook™ social networking systems and methods, MySpace™ social networking systems and methods, Linked In™ social networking systems and methods, or the like. Embodiments may also employ aspects of known weight reduction support group systems and methods, particularly those that are enhanced through electronic telecommunications such as the Weight-Watchers.com™ weight management portal, TheDaily Plate.com™ nutrition and weight management system, and the like. The sensor data sharing aspects of many embodiments may employ systems somewhat analogous to (and/or may be modified from) web-enabled athletic training community systems such as those of TrainingPeaks.com™, EnduranceNation.us™. Still further aspects of the invention may be facilitated by systems and methods that have been developed (and are continuing to be developed, and/or will be developed in the future) in support of Health 2.0 concepts. Hence, embodiments of the inventions described herein may leverage or be modified from a variety of known technologies, including by employing Elgg tools and solutions for creation of online communities as available at http://elgg.org.

An example system 100 suitable for implementation of embodiments of the present invention is illustrated in FIG. 1. In the embodiment shown, the system 100 comprises an implanted device 110 that communicates with a home monitor 120 via a wireless transmitter 112, such as an RF telemetry module. The implanted device 110 includes at least one sensor 114 and, optionally, stimulation circuitry 116 for providing therapeutic stimulation to the patient. A server 130 communicates with home monitor 120 via an internet or other telecommunication system so as to allow access to sensor-based data via a portal 150 and/or health coach workstation 160, thereby providing sensor-based feedback to a patient 140 (through direct presentation of the sensor-based information to the patient, and/or through a health-coach/patient relationship).

Each of implanted device 110, home monitor 120, server 130, health coach workstation 160, and a portable patient device will typically include associated data processing systems, with the overall feedback system 100 combining their data manipulation and communication capabilities into an overall data architecture. Generally, the data processing systems included in the discreet devices of the invention may include at least one processor. For implantable device 110, this will typically include circuitry implanted in the patient. Other devices of system 100 will include circuitry external of the patient. Such external processor circuitry may include one or more proprietary processor boards, and/or may make use of a general purpose desktop computer, notebook computer, handheld computer, Smart phone, or the like. The external processor may communicate with a number of peripheral devices (and/or other processors) and these peripheral devices may include a data and/or programming storage subsystem or memory. The peripheral devices may also include one or more user interface input devices, user interface output devices, and a network interface subsystem to provide an interface with other processing systems and networks such as the Internet, an intranet, an and/or the like. Implanted circuitry of the processor system may have some of the constituent components described above for the external circuitry as well being coupled to an implanted battery or other power source, with the implanted circuitry generally employing processors, data and software storage, and wireless communication capabilities (although hard-wired embodiments or other transcutaneous data transmission techniques could also be employed).

Both external and implanted memory of the devices of system 100 will often be used to store, in a tangible storage media, machine readable instructions or programming in the form of a computer executable code embodying one or more of the methods described herein. The memory may also similarly store data for implementing one or more of these methods. The memory may, for example, include a random access memory (RAM) for storage of instructions and data during program execution, and/or a read only memory (ROM) in which fixed instructions are stored. Persistent (non-volatile) storage may be provided, and/or the memory may include a hard disk drive, a compact digital read only memory (CD-ROM) drive, an optical drive, DVD, CD-R, CD-RW, fixed or removable flash memory, memory sticks, solid-state removable memory, and/or other fixed or removable media cartridges or disks. Some or all of the stored programming code may be altered after implantation and/or initial use of the device to alter functionality of the system.

The functions and methods described herein may be implemented with a wide variety of hardware, software, firmware, and/or the like. In many embodiments, the various functions will be implemented by modules, with each module comprising data processing hardware and associated software configured to perform the desired function. The modules may be largely integrated together so that a single processor board runs a single integrated code for each device, but will often be separated so that, for example, more than one processor board or chip or a series subroutines or codes are used. Similarly, a single functional module may be separated into separate subroutines or be run in part on separate processor chip that is integrated with another module. Hence, a wide variety of centralized or distributed data processing architectures and/or program code architectures may be employed within different embodiments.

The electronic circuitry of the various devices of system 100 communicates via RF wired or wireless networking, and/or via telecommunications linkages for coordinating the presentation of sensor-based feedback from implanted device 110 to patient 140, as well as to monitor and facilitate the various operations of the devices, including sensing, stimulating, signal transmission, charging and/or using energy from a battery device for powering the various devices, and the like. In some embodiments, the electronic circuitry of one or more of the devices includes an internal clock. The internal clock may also include a real time clock component. The internal clock and/or real time clock may be used to control stimulation, e.g., by stimulating or allowing stimulation at a particular time of the day. The real time clock component may also provide a date/time stamp for detected events that are stored as information in a memory device, including sensor-based events, patient presentation events (such as accessing portal 150, receiving a text message, communicating with a health coach or group member, or the like). Optionally, the memory may be preserved by saving information corresponding to an event of interest which is saved along with the time/date when the event occurred.

Figure 2A:
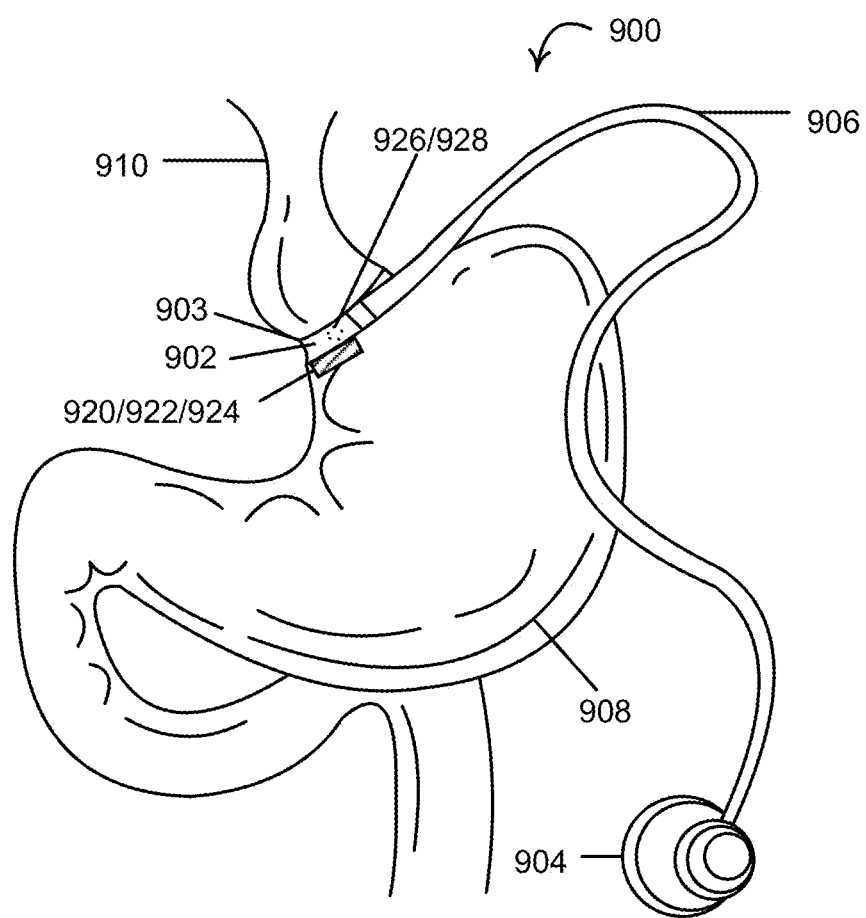
FIGS. 2A-2C illustrate alternative embodiments of system 900.
Figure 2B:
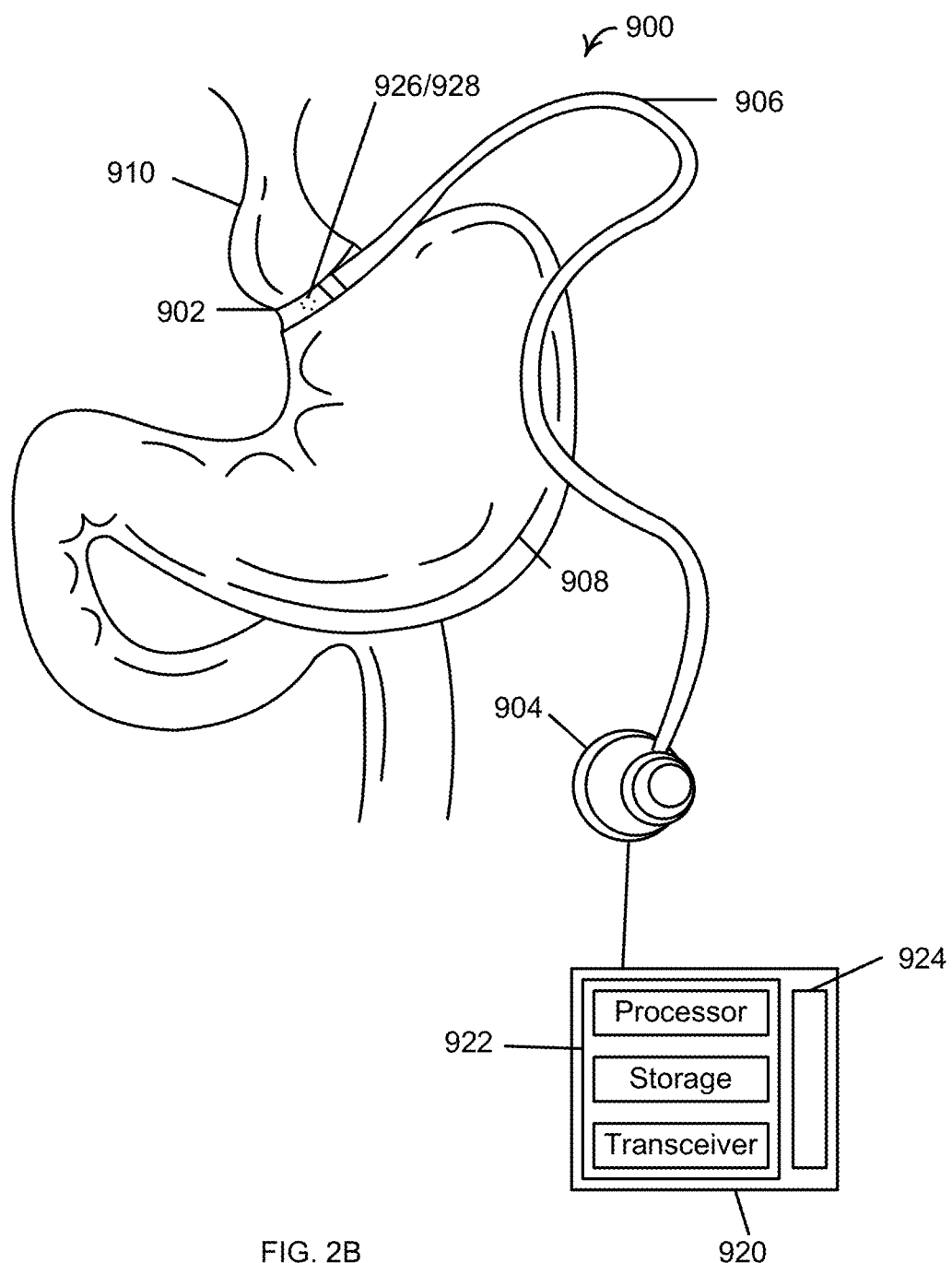
Figure 2C:
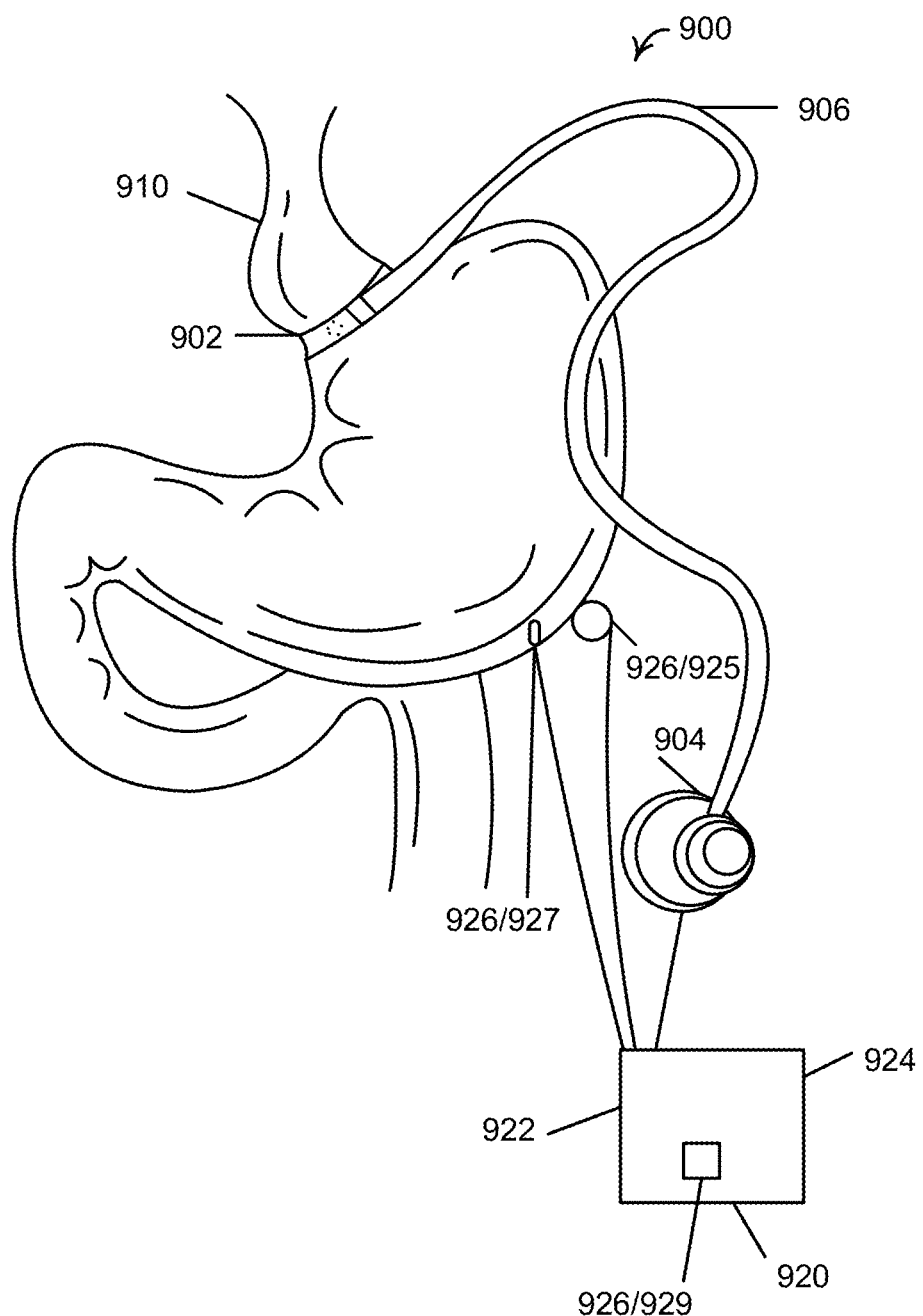

Sensor 114 is coupled to at least one part of the gastrointestinal system, such as the gastric pouch or the stomach, so as to generate signals responsive to ingestion, with the sensor ideally comprising at least one temperature sensor for sensing temperature information from within the stomach. The sensors may be located on or extend from a housing of implanted device 110 and/or the sensors may be located on or extend from a lead or other device. Alternatively, sensor 114 may be included as part of a multifunctional transgastric probe 2000. FIG. 2G shows a multifunctional transgastric probe 2000 comprising integral temperature sensor 2002 and impedance sensor electrodes 2004*a* and 2004*b* and a return electrode 2006. The transgastric probe 2000 has an outer surface comprised of a series of bands of isolated electrically conducting surfaces 2008 alternating with electrical insulators 2010. Examples of conductive materials include metals, metal alloys, and combinations of these and similar materials. Examples of such materials include MP35N, steel, stainless steel, titanium, platinum and platinum iridium or other similar materials. Examples of electrically insulating materials comprise silicon dioxide, silicone rubber, PEEK, Kynar, and Teflon. Both the conductive and insulating materials are chosen to be biocompatible and withstand the corrosive environment of the gastrointestinal system, in particular the stomach. The multifunctional transgastric probe 2000 protrudes through the stomach wall 2007 into the interior of the stomach. The electrically conducting surfaces 2008 of the probe 2000 are in direct contact with stomach contents 2005. These conducting electrode surfaces are subsequently connected to an electrical impedance spectrometer (not shown) or an excitor circuit that produces low amplitude (<1 mA peak) current pulses (<100 ms duration)-via conductive wires 2004*c* and 2004*d* respectively. The electrical signals generated at these isolated electrodes can then be used to perform subsequent analysis of the material(s) in contact with them 2005. For example, the impedance data can give information as to the electrical conductivity and pH, as well as other characteristics to enable identification of the ingested material 2005. The transgastric probe 2000 includes a temperature sensor 2002 for sensing the temperature in the immediate area of (and/or within an interior of) the gastric pouch or stomach. The return electrode 2006 function facilitates electrical stimulation, sensing, and the like, and may also be configured so that the returning stimulation current may have higher current density than other return electrode structures. In this embodiment the area of the return electrode in direct contact with the stomach is approximately 28 mm$^2$. This configuration may produce more consistent lead impedance measurements since the gastric pouch contents are less likely to alter the measurements. In the cases where this embodiment is used on a stomach wall, the stimulation current may also be more likely to flow on the exterior of the stomach wall.

FIG. 2G1 shows an alternative embodiment of the multifunctional transgastric probe. The multifunctional transgastric probe may be constructed from concentric cylinders of alternating conducting (metallic) and insulating (e.g., plastic, ceramic) stomach-acid resistant materials. In this embodiment only two materials need be exposed to the internal stomach environment. Advantageously, the concentric design permits relatively large areas of contact between cylinders to facilitate sealing. Sealing can be accomplished with adhesive and/or thermal expansion/contraction. All electrical connections are made internal to the electrode assembly and can be readily accessed during assembly. The impedance electrode can share an electrical wire with the temperature sensor/thermistor, reducing wire-count if desired. Weak impedance-measurement excitation current largely follows electric field lines. Desirably an insulating cap 2009 will keep the opposing wall of stomach from shunting the impedance current.

Figure 2D:
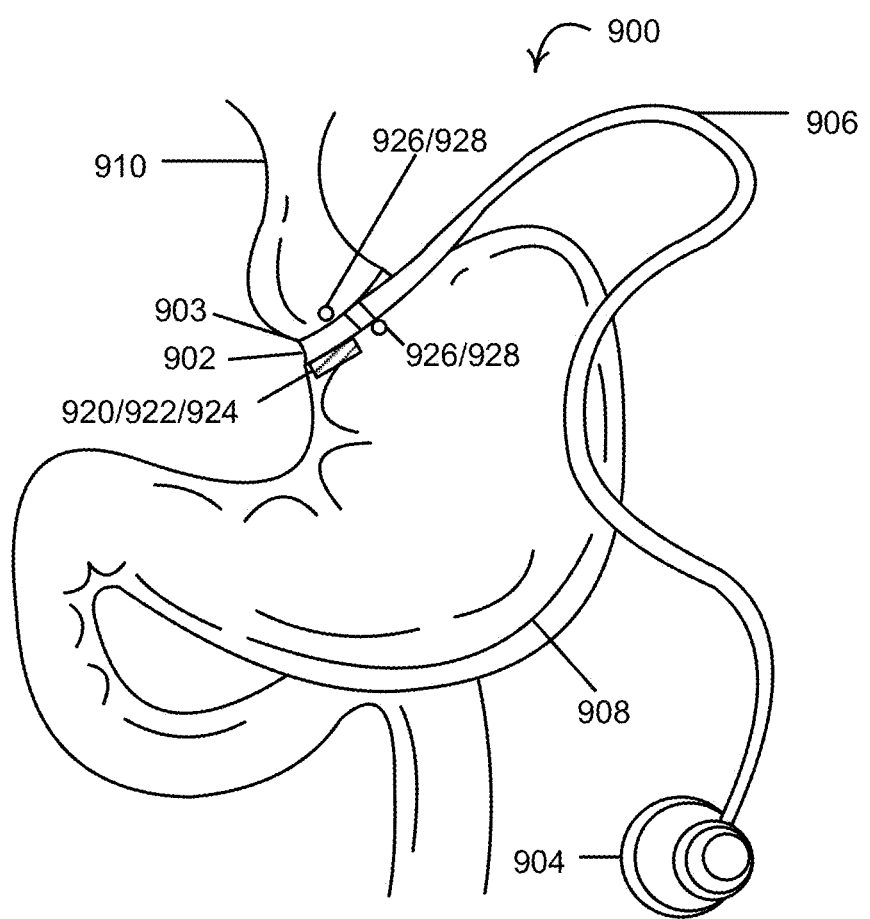
FIG. 2D shows an embodiment of system 900 comprising two pressure sensors 928 coupled to the fluid-filled cuff 903.
Figure 2E:
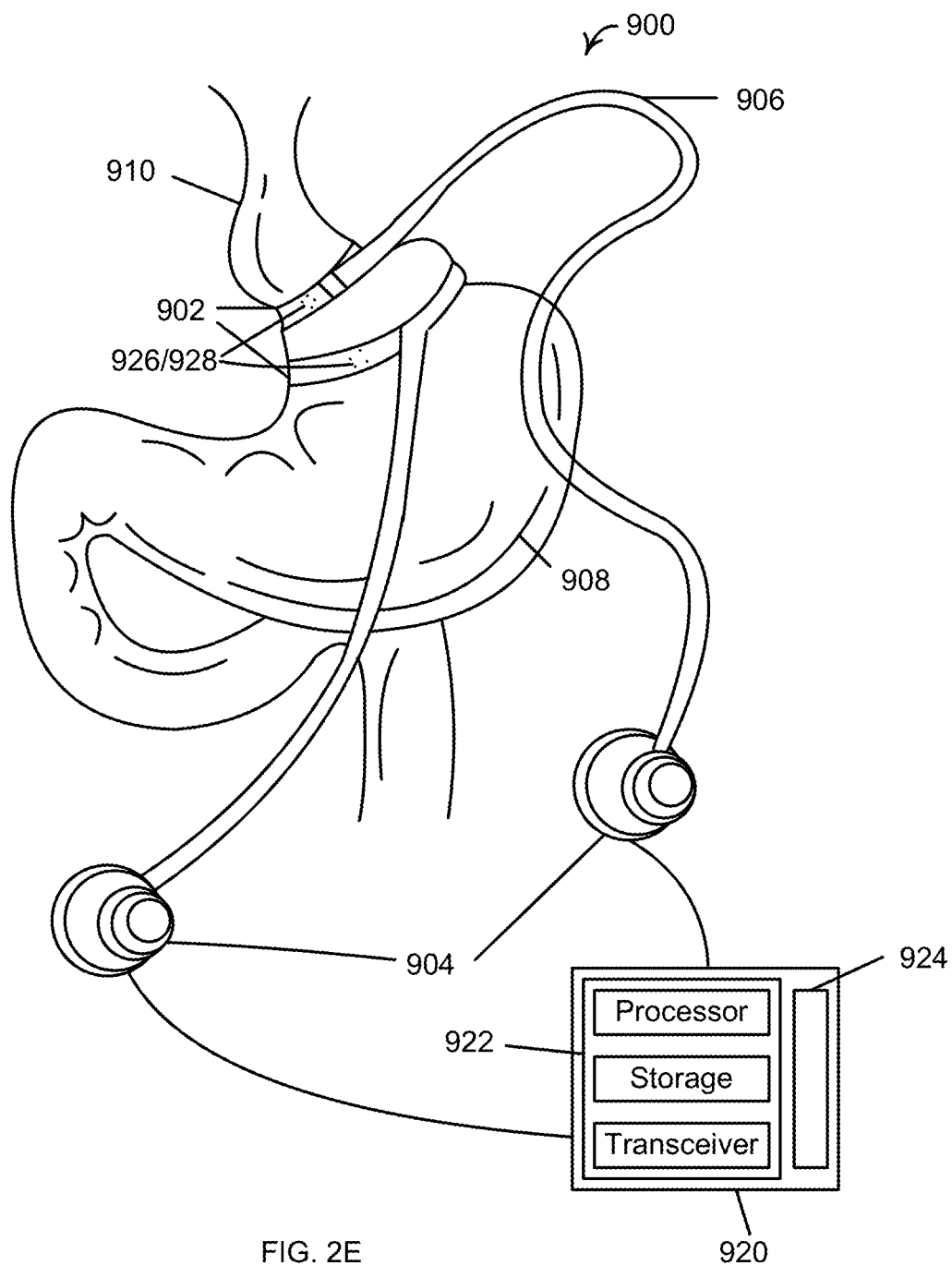
FIG. 2E shows an alternative embodiment of system 900 comprising at least two lap bands, each lap band comprising at least one sensor 926.
Figure 2F:
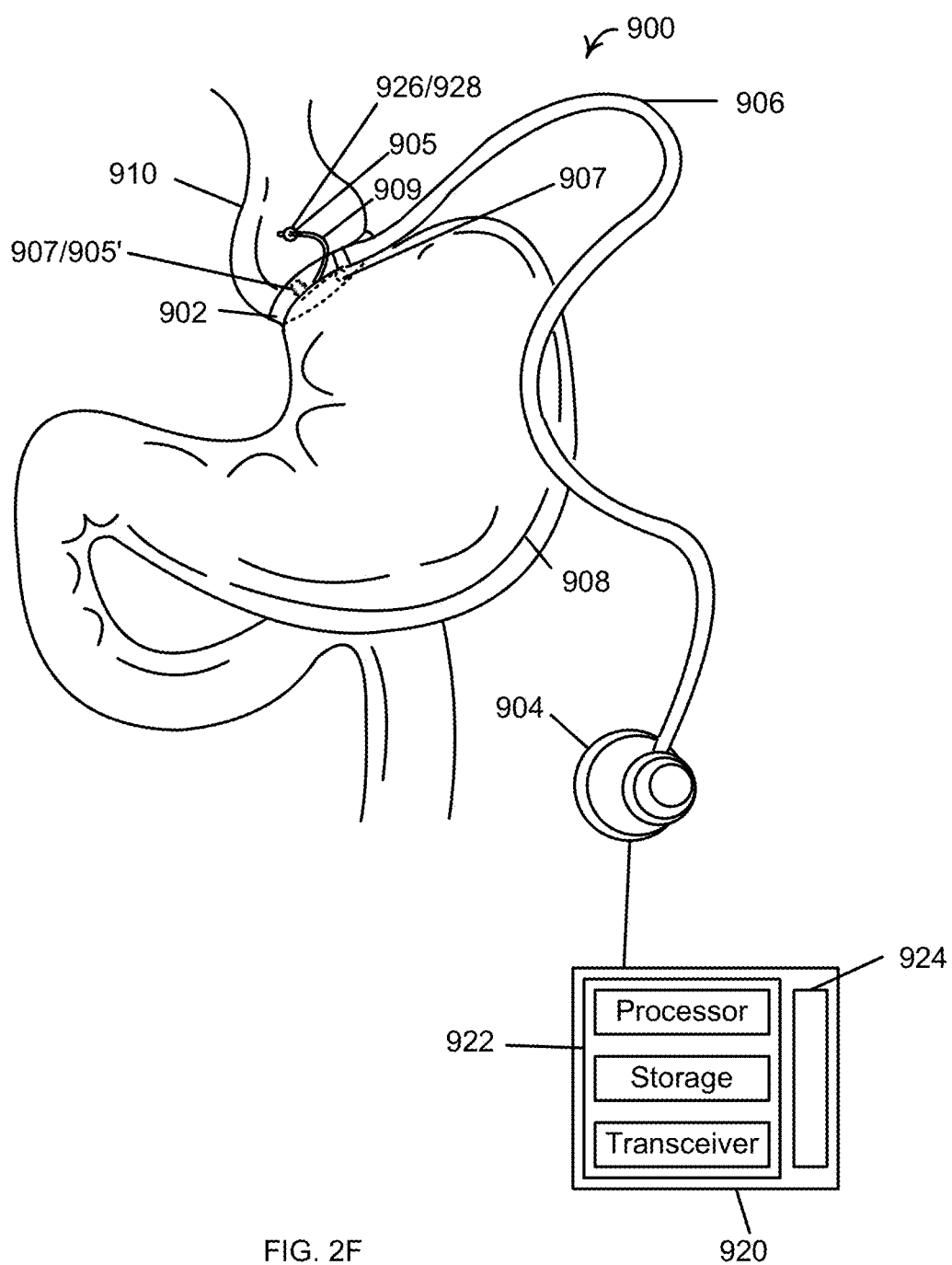
FIG. 2F shows an alternative embodiment of system 900 comprising at least one sensor extending through a wall of the gastric pouch and at least two electrodes placed inside a lap band to provide electrical stimulation to the portion of the stomach in contact with the lap band and/or sense gastric impedance.
Figure 2G:
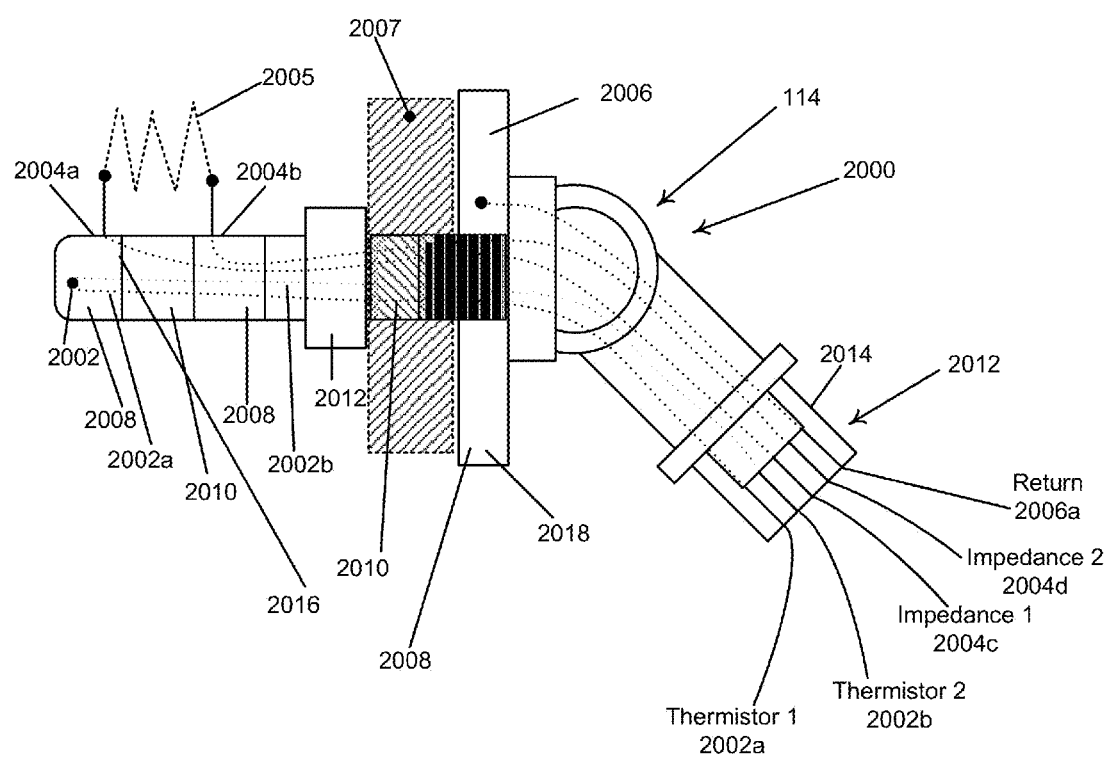
FIG. 2G shows a multifunctional transgastric probe comprising integral temperature and impedance sensors and a return electrode.
Figure 21:
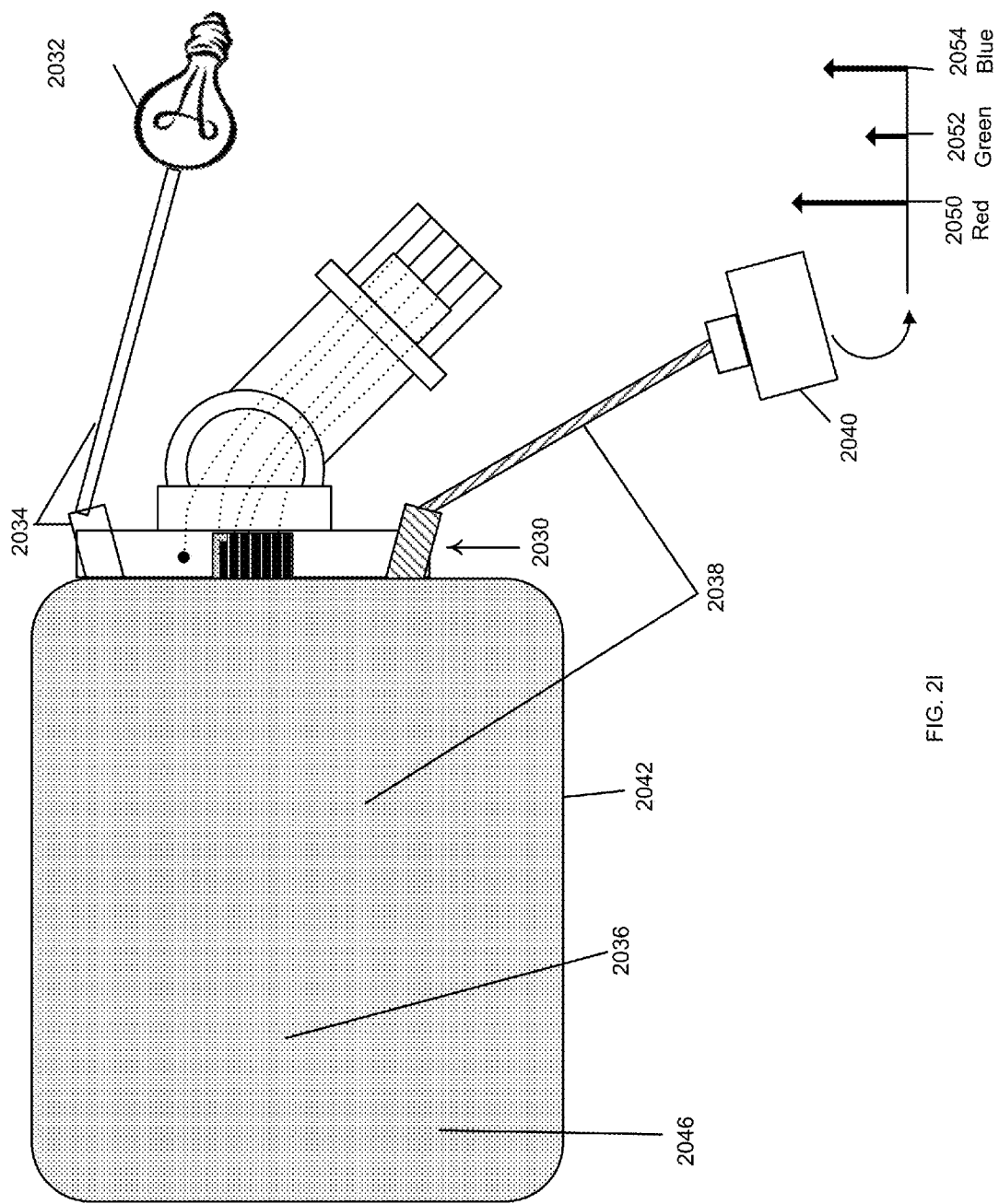
Figure 2J:
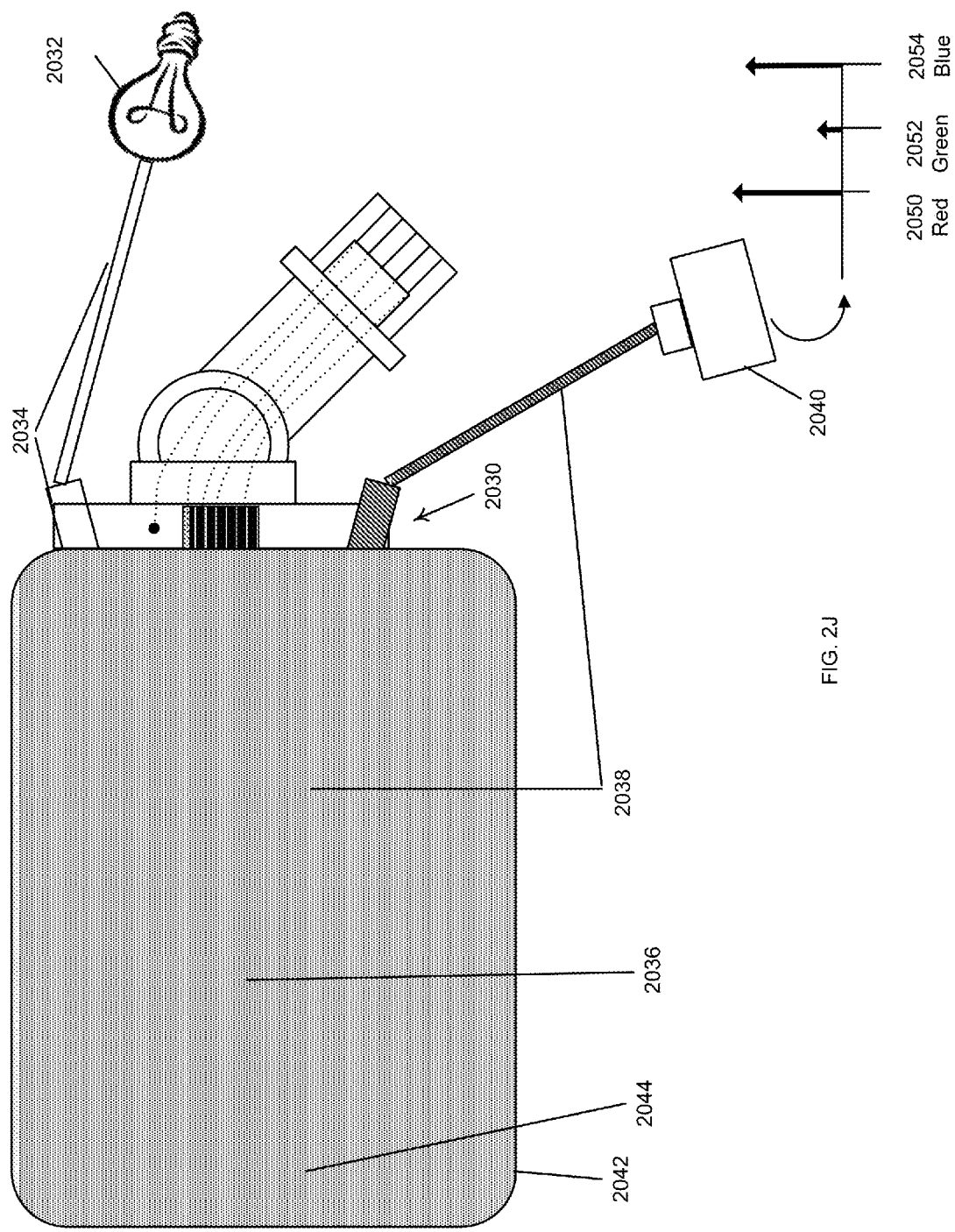
FIG. 2J shows a schematic configuration with a color sensor response when the gastric pouch cavity includes a translucent material such as coffee or a dark-colored soda.
Figure 2K:
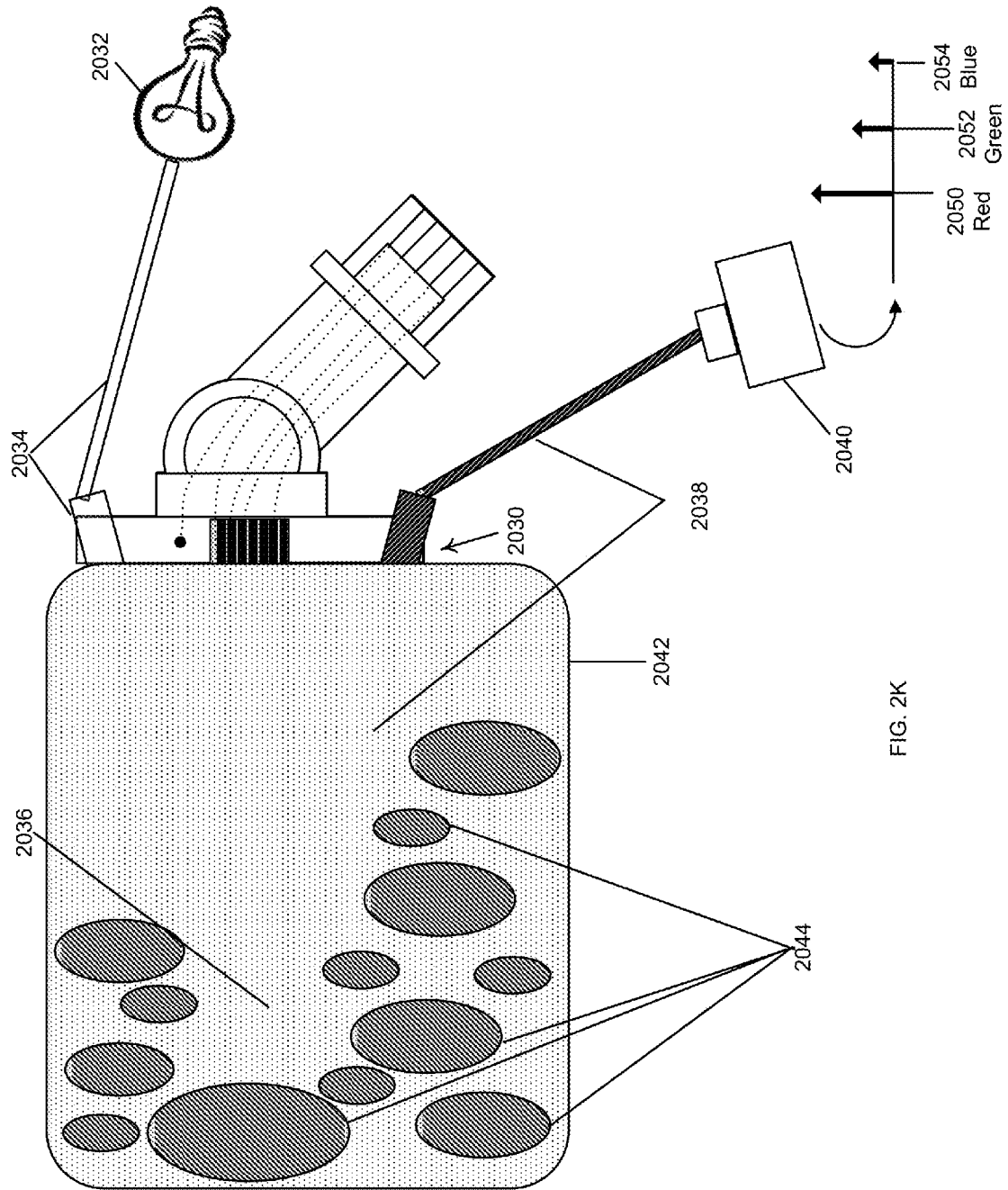
FIG. 2K shows a schematic configuration with a color sensor response in a case after ingestion of a largely opaque meal in the gastric pouch cavity.
Figure 3:
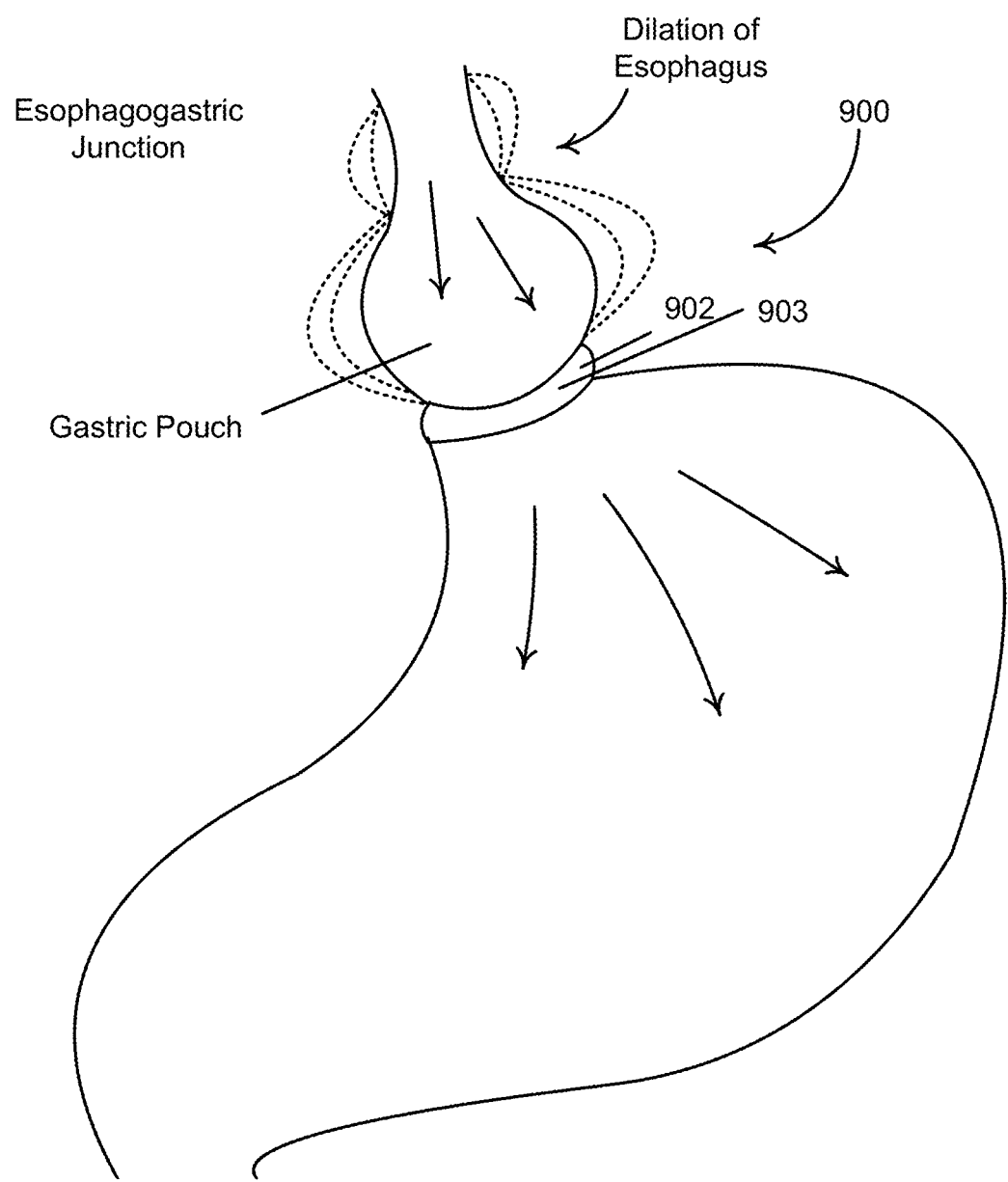

FIGS. 2G2 and 2G3 show further alternative embodiments of the multifunctional transgastric probe concentric cylinders of alternating conducting (metallic) and insulating (e.g., plastic, ceramic) stomach-acid resistant materials.

Typically the lead body is comprised of an elongate structure having conductive wires passing therethrough or therealong to couple the various sensors and electrodes disposed along the lead to the connectors (not shown) and then to the stimulation circuitry 116. In some embodiments, the lead body 2014 is comprised of an extruded polymer having one or more lumens, typically wherein each conductive wire passes through a separate lumen. Thus, the conductive wires are insulated from each other, in addition to any individual insulation coating, and are protected from possible damage. Example polymers include thermoset elastomers, such as silicone, thermoform polymers, such as polyurethane, and thermoform elastomers, such as Santoprene®, to name a few.

As shown, the transgastric probe 2000 has an elongate cylindrical portion 2016 which joins with a hub 2018 which in turn joins with the lead body 2014. Typically, the cylindrical portion 2016 has a length in the range of approximately 15 mm to 35 mm and a diameter in the range of approximately 2 mm to 5 mm, with a preferred diameter of 3 mm, but not so limited. Such dimensions are chosen to allow sufficient extension of the cylindrical portion 2016 through the gastric pouch wall and into the gastric pouch. In addition, the cylindrical portion 2016 has an atraumatic tip, such as having a smooth, rounded shape, to reduce any possibility of acute or chronic injury to the lining of the gastric pouch.

In this embodiment, the cylindrical portion 2016 includes a tissue engagement feature 2012. The feature 2012 extends radially outwardly and is positioned a distance from the hub 2018 to assist in maintaining at least a portion of the stomach wall 2007 therebetween. The hub 2018 may have a variety of shapes and may be configured to maintain the cylindrical portion 2016 at an angle theta in relation to the lead body. Alternatively or additionally, in this embodiment the cylindrical portion 2016 is disposed at a 110 degree angle in relation to the lead body. It may be appreciated that the angle theta may range from 0 to 180 degrees, or 90 to 180 degrees, however an angle of less than 180 degrees is typically desired to assist in extending the lead body 2014 across the outer surface of the stomach.

The cylindrical portion 2016 has a hollow construction within which is disposed a sensor 114. It may be appreciated that a plurality of sensors may also be used. In this example, the sensor 114 comprises a thermistor. A variety of temperature sensors can be used, including negative temperature coefficient thermistors, positive temperature coefficient thermistors and thermocouples and thermopiles. In this example, a set of conductive wires 2002*a* and 2002*b* extends from the sensor 114, through the hub 2018 and through the lead body to the proximal end of the lead. The hollow section of the cylindrical portion 2016 is filled with potting material, such as epoxy, to protect and seal the sensor 114 and conductive wires 2002*a* and 2002*b* in place. Together with the epoxy, the cylindrical portion 2016 and hub 2018 create a continuous barrier to protect the thermistor from fluid or other environmental factors. Since in this embodiment the probe 2000 is formed from a thin thermally conductive metal, external surface temperature changes are quickly thermally-conducted to the internal thermistor for measurement. Further, the electrically conductive metal allows the probe 2000 to act as a return electrode. Thus, another conductive wire 2006a extends from the probe 2000 through the lead body and attaches to the conductive metal to act as a return electrode.

FIG. 2G1 shows an alternative embodiment of the multifunctional transgastric probe. The multifunctional transgastric probe may be constructed from concentric cylinders of alternating conducting (metallic) and insulating (e.g., plastic, ceramic) stomach-acid resistant materials. In this embodiment only two materials need be exposed to the internal stomach environment. Advantageously, the concentric design permits relatively large areas of contact between cylinders to facilitate sealing. Sealing can be accomplished with adhesive and/or thermal expansion/contraction. All electrical connections are made internal to the electrode assembly and can be readily accessed during assembly. The impedance electrode can share an electrical wire with the temperature sensor/thermistor, reducing wire-count if desired. Weak impedance-measurement excitation current largely follows electric field lines. Desirably an insulating cap 2009 will keep the opposing wall of stomach from shunting the impedance current.

FIGS. 2G2 and 2G3 show further alternative embodiments of the multifunctional transgastric probe concentric cylinders of alternating conducting (metallic) and insulating (e.g., plastic, ceramic) stomach-acid resistant materials.

FIG. 2H shows an alternative embodiment of the multifunctional transgastric probe which also comprises a portion of a color detector 2030 at the distal end of the probe 2000. FIG. 2H1 shows a close-up view of the multifunctional transgastric probe which comprises a portion of a color detector 2030. The entire color detector 2030 is comprised of a source of white/visible light e.g., LED 2032 conducted into the cavity of the gastric pouch or stomach via a fiber-optic illuminating 'light pipe' 2034, a transparent nosepiece 2036 attached to the distal portion of the multifunctional transgastric probe, a second 'light pipe' 2038 which conducts a spectrum of light that has passed through material within the stomach and/or been reflected from the surface of the inside wall of the stomach, and a color sensor 2040 which e.g., generates electrical signals corresponding to the intensities of the red, green, and blue wavelengths of the reflected light. The probe 2000 includes the transparent nosepiece 2036 and its provisions for interfacing to the illuminating and reflected light pipes. The light conducting material (light pipes) 2034 and 2038 and the transparent nosepiece are produced from light-conducting, optically transparent (at the wavelengths of interest) and corrosion resistant to the environments of the stomach and gastric pouch, such as pure silicon dioxide, quartz, or diamond. The light illuminates a small area of the gastric pouch wall 2042 opposite the protruding electrode. The light also illuminates ingested material(s) 2044 located between the nosepiece and the opposite gastric pouch wall. Source light reflected by the generally opposed gastric pouch wall and/or ingested contents re-enters the nosepiece 2036 as well as a second robust light-conducting component, and is subsequently conducted, via a second light pipe, to a color light sensor e.g., three photosensors or photodiodes 2042, 2044, and 2046 with color filters, or an integrated commercial color light sensor (not shown). Each of the photodiodes 2042, 2044, and 2046 measures its designated color intensity, e.g., red, green, and blue. The sums and ratios of these intensities are then used as an indicator that (a) the stomach is largely empty, or (b) there is ingested material within the stomach cavity, and (c) the composition of the ingested material (with limited precision).

The light path(s) may be of significant alternate forms and could be separate from the temperature probe. The nosepiece maintains a space in front of the light-conducting components such that light is not blocked from reflecting from the stomach wall and/or ingested material and subsequently being sensed. The detected wavelengths can also include those of non-visible light e.g., infrared, desirably near infrared. In particular, two bands detecting ranges 1130-1180 nm and 1360-1400 nm can be used to differentiate water from sugared beverages and beer.

FIG. 2I shows a schematic configuration of the color detector 2030 and sensor 2040 in the multifunctional transgastric probe in a case when the gastric pouch is largely empty or in the presence of a clear liquid such as water. Note that the color intensities measured by the photodiodes reflect the color of the interior of the gastric pouch cavity.

FIG. 2J shows a schematic configuration with a sensor response in a case when the gastric pouch cavity includes a translucent material such as coffee or a dark-colored soda.

FIG. 2K shows a schematic configuration with a sensor response in a case after ingestion of a largely opaque meal in the gastric pouch cavity.

Alternatively or additionally, a sensor 114, desirably a temperature sensor, may be otherwise positioned elsewhere within, coupled to or in communication with the patient. In some embodiments, data obtained from the sensor 114 may be pre-processed to remove noise or unwanted artifacts before it is analyzed. Additional sensors may be included, including a core body temperature sensor, an accelerometer, and/or a heart-rate/respiration-rate sensor(s) to measure patient activity or the like. The housing of implanted device 110 will typically contain a battery and circuitry of the implanted device, and may be similar to other known implantable stimulator housing structures used for heart pacemaker systems and the like. A suitable heart rate sensor may comprise an electrode or other sensor engaging the stomach wall so as to receive (far field) electric signals from the heart. Optionally, such a heart rate sensor may employ the same electrode as used to stimulate stomach tissue to inhibit ingestion, though separate electrodes may alternatively be used. Heart signals, accelerometer signals, and/or other activity sensor signals may, like temperature or other ingestion sensor signals, be processed and recorded using circuitry 116. Suitable sensors and implantable devices, as well as aspects of the other devices of the devices of system 100, are described in (and/or may be modified from those described in) U.S. patent application Ser. No. 12/754,439 filed on Apr. 5, 2010, U.S. patent application Ser. No. 12/145,430, filed on Jun. 24, 2008 and U.S. patent application Ser. No. 10/950,345, filed on Sep. 23, 2004, all of which have previously been herein incorporated by reference. Processing of sensor signals so as to identify or classify ingestions events and/or patient activity level to be communicated by system 100 (which may occur partially or entirely in implanted device 110, home monitor 120, or server 130) may be more fully understood with reference to Provisional U.S. Patent Application No. 61/122,315, filed on Dec. 12, 2008 and U.S. patent application Ser. No. 12/637,452, filed on Dec. 14, 2009 which were also previously incorporated herein by reference.

The home monitor 120 includes a processor 122, a storage medium 124, and transmitting/receiving circuitry 126 and is capable of interrogating the implanted system 110 (and of receiving sensor-based data in response) when the patient is within a predetermined distance of the monitor. In some embodiments, this distance is approximately twenty to thirty feet. The data interrogation could also be initiated by the patient via an input into home monitor 120 or a mobile device such as an iPhone® smart phone with Abiliti® Pocket Coach software. The information communicated to the home monitor 120 is encrypted and sent via the internet to a HIPPA compliant server 130. The information is then accessible directly by the patient 140 or by approved medical personnel serving as the patient's health coaches (optionally via a workstation 160) via a secure web site or other portal 150. While the home monitor will often comprise a desktop computer or other desktop unit powered by a wall plug, alternative systems may employ home monitors with smaller form factors (the home monitor optionally comprising and/or being similar in size to a notebook computer, a smart phone, a personal digital assistant, or the like) powered by batteries or other portable power sources. Where wireless phone capability is not available to a patient (such as for a patient visiting or living in a rural area) the home monitoring system could also comprise a hand held computer and a port that is connected to the internet via a land-based telecommunications link such as via a modem and telephone connection. The implanted device could be interrogated through radiofrequency (RF) communication with the handheld computer. Such a handheld computer could also be used to enter journal information. Placing the hand-held computer in the port would allow uploading of retrieved device data, and journal entries to the internet portal. Some or all of the functionality of the home monitor 120 may instead be implemented using a portable device 170 such as a smart phone, personal digital assistant, or the like. Even when a home monitor 120 is included in the system, such portable devices will allow the patient to benefit from communications to and/or from server 130 when the patient is out of the house.

The server 130 contains a number of algorithms designed to evaluate the implanted device data logs in comparison with goals established by the patient and his or her health coaches 160. Based upon the results of the analysis, such as whether the goals have been met, coaching messages may be sent to the patient, for example via email, text message or telephone call. The messages are designed to provide encouragement for positive results and positive reminders for negative or neutral results. This coaching feature encourages patients to obtain energy balance in their lives. Specific examples regarding energy expenditure include sending encouraging messages for meeting daily or weekly activity goals or sending patient alerts if extended periods of sedentary activity have occurred. With regard to caloric intake, examples include communicating feedback to the patient as to whether eating patterns show adherence to the eating plan or whether caloric intake is meeting daily, weekly, or monthly goals.

Information in the data logs from the activity and consumption sensors of the implanted device 110 will also allow cross-checking between the patient's activity and meal diary and device-detected events. If the diaried and the detected events do not match (such as when the sensed data indicates that food was ingested but a snack or meal was not logged in the diary, or when a meal time or food intake quantity exceeds a logged meal), then reminders may be sent to the patient to enter additional information in the diaries, and/or to a health coach to check in with the patient. Diary entries may be made by a patient via multiple devices (for example, using a home computer when at home, a notebook computer when at the office or traveling, and/or a smart phone while at a restaurant, or the like) and in a variety of different formats (including options for text diary entries, voice entries, photo entries taken via a digital camera or telephone, and the like). Although diaries for the purpose of calorie counting have been typically inaccurate due to lack of patient compliance or attention, this feedback system facilitates improved accuracy. In addition, alerts can be set that send performance summary reports to the patient's health coach and/or physician, which allows the health coach or physician to intervene when needed. The intervention could be in the form of extra coaching for the patient, revising of a weight loss/exercise plan, reprogramming of the implanted device stimulation parameters, or the like.

In embodiments of the present invention, the patient may be provided with a hand-held or pocket device capable of receiving reminders and other notices from the server 130, or the reminders may be sent to a general purpose hand-held or pocket device such as a cell phone or e-mailer, optionally using an appropriate local user interface or other software resident on that device. A patient identification and/or password may optionally be entered to the portable device to obtain patient data so as to prevent others from accessing sensor-based data. The notices transmitted to the portable device may include daily inspirational messages; diet and exercise education information; and particularly feedback messages (for example, identifying positive and negative events, reached daily goals, missed goals, skipped meals, excessive meal quantities or times, and/or added meals or snacks). The feedback messages may be generated by algorithms contained on the server 130; and/or cross-checking between device data logs and patient reporting. In some embodiments of the invention, patients may be offered the option to join an online support group of patients with similar body mass indexes (BMI) who have similar attributes and weight loss goals. This group may meet online using the website 150 to provide support for one another, as well as review each other's results and provide support and encouragement to each other via email or text messaging via their patient-associated portable devices. Hence, the patients may optionally share access to their sensor-based data with one or more other appropriate patients so as to allow the other patients to act as health coaches to the patient in which device 110 was implanted, and/or so as to allow the implant patient to coach those other patients based on their associated sensor-based data. The patient will also optionally have the ability to invite health coaches into the online community, with the patient typically granting and managing a support group of the patient by granting permission to individuals to whom the patient is willing to allow access to the patient's sensor-based data. The supporter or member of the group may be a spouse, a gym coach, a parent, a friend, or a family member. In some embodiments, the group may include another patient having an implant providing sensor-based data. Hence, the group may comprise a mutual support group.

The patient and/or health coach may obtain updates by accessing a web site or other portal 150. The portal will optionally comprise a secure website into which the patient or other system user enters a patient identifier and/or password, allowing patients to log into the site with confidence that the system is safe and secure. Patients should feel sensitive medical data is sufficiently protected and that highly sensitive medical data is not displayed as appropriate given the value of the portal. Portal 150 may optionally comprise a "support dashboard," includes a comprehensive set of weight loss tools designed to support the individual. In addition, the support dashboard may allow access to the data logged by the implanted device 110 by the patient. The usefulness of the weight loss tools included in portal 150 may be enhanced through the ease by which the patient is provided accurate information on his or her daily activity and consumption. The sensor-based information may optionally be enhanced by patient reporting of specific food quantities, food types, caloric intake, and/or the like. The support dashboard may include features such as: a calorie database, an online calorie counter, a packaged food database, meal preparation support (such as custom meal menus generated for that patient), an activity diary, an exercise guide and planner, a weight tracking log, a body-mass index calculator, activity or exercise reports, meal frequency and duration reports, and/or a message center. Portal 150 may present patient performance based on predetermined activity and caloric goals, optionally including daily kilocalories to be burned, daily calories consumed, and/or a net summary of the patient's energy balance. Portal 150 may also present additional sensor-based data, including sleep or rest data (such as the number of hours slept, a quantified quality of sleep or other rest periods, and the like).

Referring still to FIG. 1, portal 150 may have a food calculator to look up calories of food types, to input quantities of their planned or consumed meals, and the like. Food calories can be input and/or determined in a variety of different ways, with the site optionally employing a food calculator or linking to a commercial calorie identifying website such as CalorieKing.com or the like. Meal logging may optionally include uploading data or photos to the portal directly or by linking to a meal logging web-base service such as that which was offered commercially by myfoodphone.com. Portal 150 may also have commercially available look-up caloric and/or nutritional data from food suppliers, including commercial prepackaged customized foods suppliers, restaurant chains, or the like.

Portal 150 may facilitate networking with identified friends using known social networking capabilities, giving users the ability to email to friends and health care providers and accepting input from such individuals so as to allow them to make public or private comments and the like. The members may connect into a live chat room sponsored by the health care practitioner support group (if desired). This may allow real time coaching based on individual own performance on eating, exercise and lifestyle opportunities. The portal may also support a group or circle of friends to allow individuals to in chat real time or transmit messages to one another. Portal 150 may optionally accept predetermined or customized user data, allowing the user to store desired health related information on their personal page, and to control the access of others to that information. This data could include blood pressure, glucose, sleep length and quality, heart rate data, and other data indicative of the general health status or goals of the patient. The portal will allow for daily notes from the individual, this will allow users to note overall feelings of wellness or questions they might have about eating and motivations.

To enhance the efficacy of coaching and overall feedback, portal 150 may allow for feedback from the network based on the individual's goals. The site will allow for messaging to the individuals own page (as well as other portable or connected device, as described above) which the user chooses. This messaging may be configured to prompt the individual based on performance achieved or notes about missed activity events, meal events, etc. The portal may also notify users when a member of their selected member friends has achieved their personal goals and/or accomplishments. Portal 150 may also include goal-setting and behavior/goal comparison tools. Simple goal setting fields may optionally be available for the patient, though more sophisticated systems may allow the patient to enter a long-term goal and may interactively help the patient to determine short term and long term intermediary goals so as to reach their ultimate weight reduction target. The system may, for example, provide an indication of the quantity of exercise that would be appropriate to achieve an interim or short term weight loss given the patient's sensed ingestion behavior. Alternatively, a reduction in ingestion may be determined based on maintaining the patient's sensed activity level may be identified by the system. Expected results from changes in ingestion and activity may be identified by the system. As significant weight loss may not be measured until a patient has maintained compliance for a relatively extended period, more immediate short-term goals may also be identified by the system, including reduction in a size of the patient (such as a reduction in dress or pants size, a reduction in waist size, a reduction in neck, arm, or leg circumference, an increase in walking endurance or speed (or other quantifiable exercise parameters), or the like may also be identified). Portal 150 may allow the patient to revise the short term and long term goals throughout the course of treatment, and may generate comparisons between the patients measured and sensed performance with their goals. The system may also be capable of tracking performance against team goals, with a team comprising weight-loss patients of a group. Team goals may be generated by the team, a healthcare provider of the team, or both. As an example, a physician could create a team of patients, each patient of the team having an implanted device. The physician could then work with the team to set a team's goals. This will allow the spirit of competition to be added into the mix for changing the behavior of the individual members of the team.

Portal 150 may include or be linked to one or more reference websites. The portal will preferably have a number of selected reference sites for members to choose from. These sites will allow users to select from a number of tools which the users may prioritize or the site may keep a current list of most frequently used sites. This allows users to refer to a particular reference site based on changing priorities and behaviors. Suitable reference sites may include information on nutrition (food selection and net calorie), food preparation, activity guidelines (walking and other exercises), Kcal Expenditure charts (including activities of daily living), and/or the like. Portal 150 will allow the user to communicate their health status to others, such as by providing the ability to send permission to view the patient's page to an MD, nutritionists, or a selected friend or group member. The patient's page on the portal will typically store a history of the patient, including their weight, wireless or other uploads by or regarding the patient, and the like. Educational links may facilitate access to nutritional information, exercise information, stress management techniques, and lifestyle coaching guides.

As indicated above, a number of additional devices may communicate with the components of system 100 shown in FIG. 1. Along with portable or handheld devices 170 (such as a BlackBerry™ wireless e-mailer, an iPod™ or other mobile music player, an iPhone™ or other mobile phone, and the like), home monitor 120 or server 130 may communicate with scales (for measuring a weight of the patient or food), pedometers, and the like. In exemplary embodiments, home monitor 120 receives wireless telemetry from a scale, glucose monitor, blood pressure cuff, and/or the like.

Figure 1A:
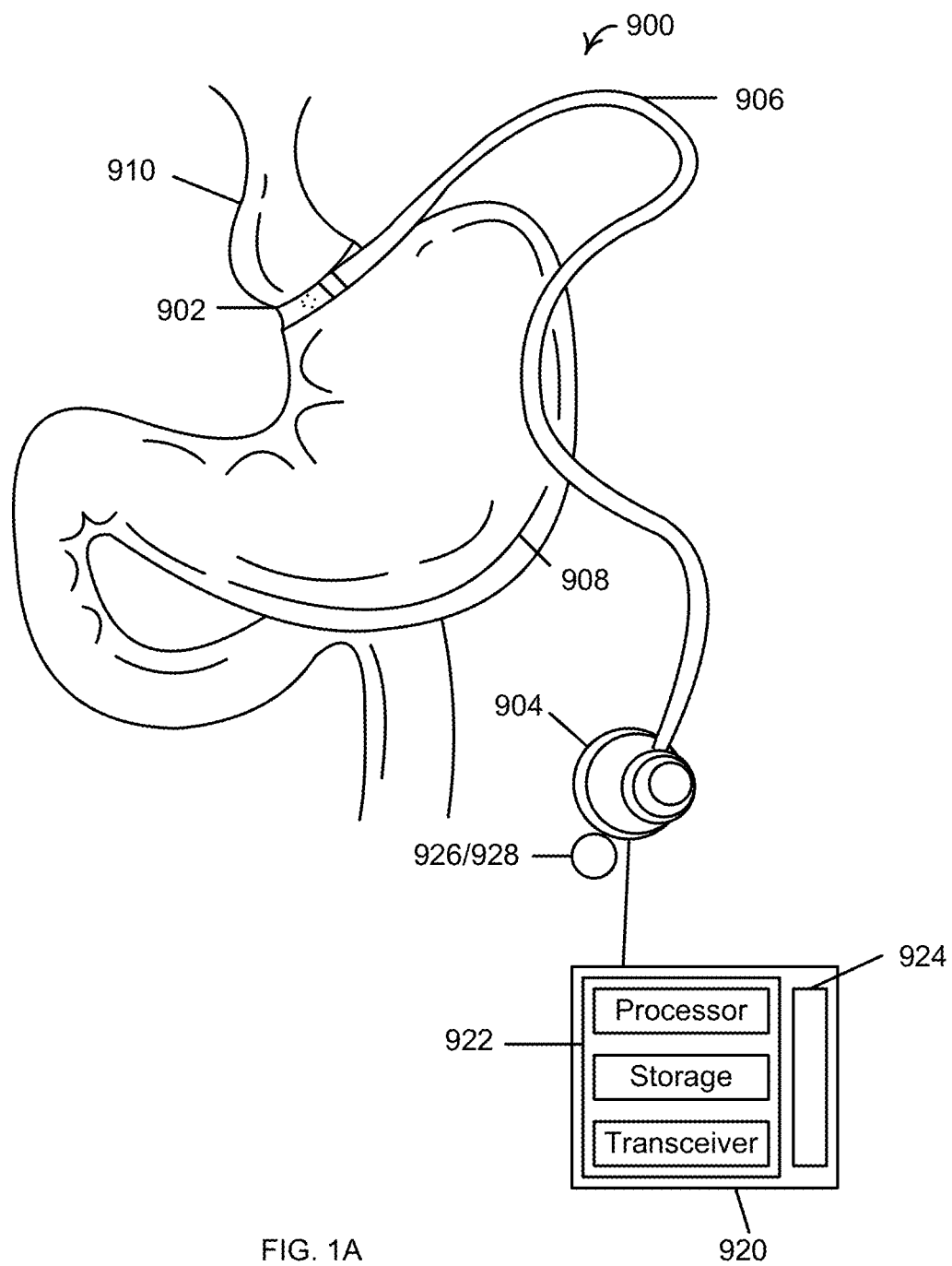
FIG. 1A shows an exemplary gastric band sensor system implant 900 for use in the system of FIG. 1.

FIG. 1A shows an exemplary gastric band sensor system implant 900. This embodiment includes a gastric band, laparoscopically implanted, also known as a lap band 902 having a fluid-filled cuff 903 coupled to an implanted port 904 via a fluid conduit 906. The gastric band may comprise any such lap band currently marketed or available in clinical trials, as for example, the Realize® Adjustable Gastric Band from Ethicon Endo-Surgery, Inc., the Lap-Band® from Allergan, Inc., the Midband™ from Medical Innovation Development, and Heliogast® Band from Helioscopie, MiniMizer Extra from Bariatric Solutions. The gastrointestinal constriction provided by lap band 902 can be varied by injecting or removing fluid from port 904 using a syringe. Along with mechanically constricting gastrointestinal flow, system 900 includes a housing 920 with circuitry comprising a processor 922 and a battery 924 to wirelessly transmit signals generated in response to signals from one or more sensors 928 to a data collection center. The data collection center comprises the web portal 150 shown in FIG. 1 or a data server. Note that the housing 920 may optionally be incorporated into port 904.

System 900 will sense ingestion using signals from at least one sensor 926. Sensor 926 comprises at least one of a pressure 928 (e.g. a MEMS-type, strain-gage, etc.), temperature, pH, acoustic, or optical sensor to detect food or drink intake. Sensor 926 may also comprise an activity sensor, such as an accelerometer, heart rate sensor, temperature-based ingestion sensor and/or a core body temperature sensor. The at least one sensor could be placed at various locations, for example at the port 904, at the lap band 902, etc. The at least one sensor may be wired to the housing 920, or communicate wirelessly with the processor in the housing.

Figure 1B:
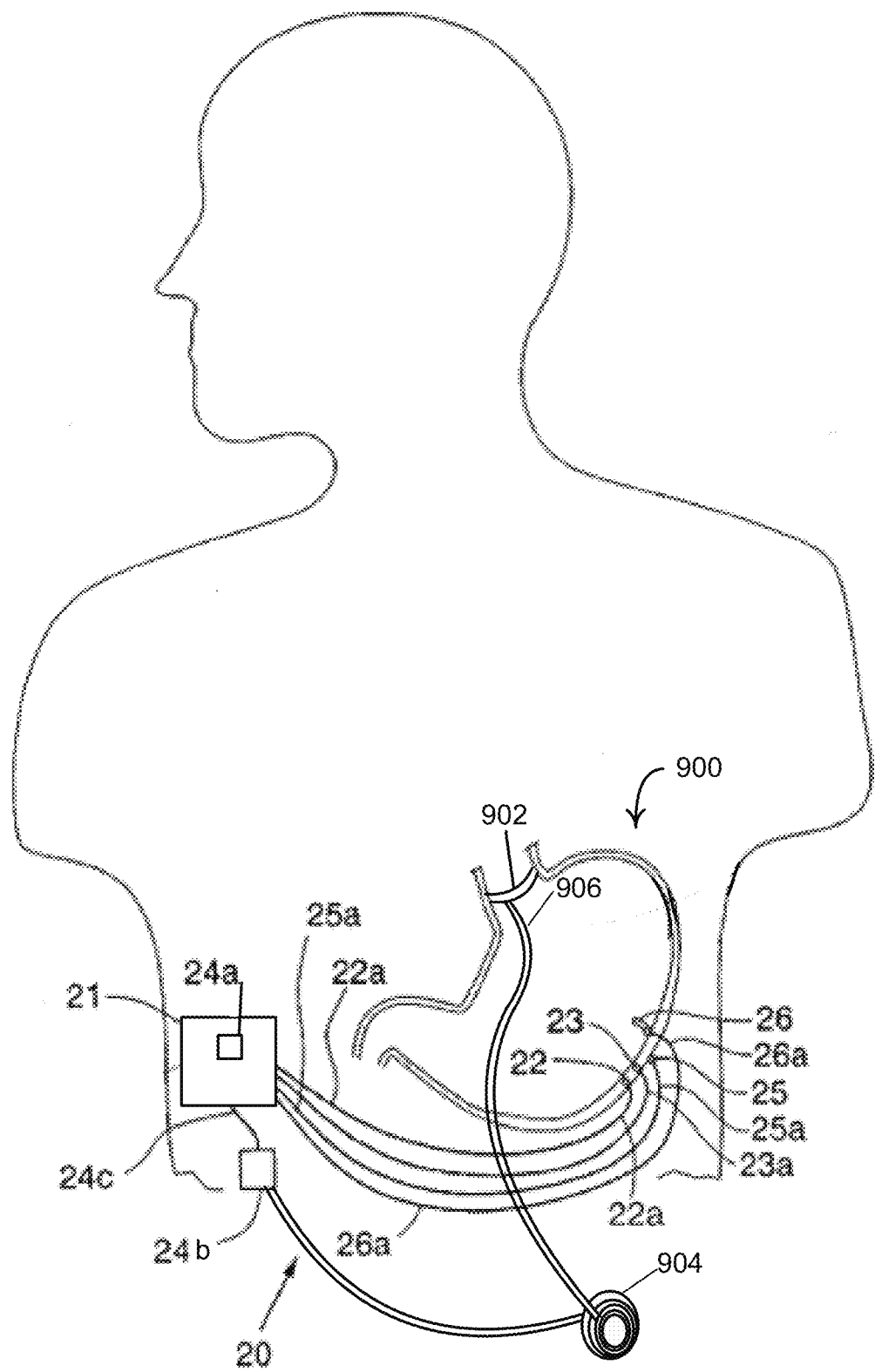

FIG. 1B illustrates the electrical stimulation component of the gastric band sensor system implant 900. The stimulator 20 comprises a housing 21 implanted subcutaneously within a patient. The stimulator further comprises leads 22a, 23a extending from the housing 21 through the abdomen and to the stomach 100 where electrodes 22, 23 at the end of the leads 22a, 23a are implanted into the stomach muscle layer from the outside of the stomach 100. A method of implanting the stimulator housing 21 and laparoscopically implanting the electrodes 22, 23 in the stomach 100 is generally known to those of ordinary skill in the art.

The housing 21 further comprises a sensor 24a located on the housing 21 and/or a sensor 24b located elsewhere in the patient and coupled to the electronic circuitry 29, (FIG. 1B) in the housing 21 by lead 24c. The sensor 24a or 24b may, for example, include an accelerometer that is configured to sense motion of the patient. The stimulator also includes sensors 25, 26, that are implanted on and in the stomach 100, respectively, with leads 25a, 26a extending from the sensors 25, 26 to the housing 21. Sensor 26 is exposed to the inside of the stomach 100 while sensor 25 is attached to the outside of the stomach. Leads 22a, 23a and 24c, 25a, 26a are electrically coupled to the electronic circuitry 29 located in the housing 21. When the sensors 25, 26 are implanted in the stomach, they may sense presence of material in the stomach, composition of such material and temperature, pH or pressure within the stomach, and/or patient motion corresponding to respiration or gross movement. Sensors positioned on the stomach may also sense various parameters that indicate the actions of the stomach, e.g., movement, contractions. The sensors positioned on the stomach may also utilize various imaging techniques, e.g., ultrasound, and light, to identify presence or composition of food or material in the stomach.

In use, once the stimulator 20 is deployed, electrical stimulation is provided through electronic circuitry 29. The electronic circuitry 29 is capable of producing various types of programmable waveforms that provide stimulation to the smooth muscle lining of the intestinal tract. It is well known to those of ordinary skill in the art, there are many different types of electrical stimulation programs and strategies which can be utilized for providing electrical stimulation parameters through the circuitry 29, the principal focus being providing electrically stimulating parameters for the stomach. In one embodiment the focus of the electrical stimulation is to cause gastric retention of food to produce a sensation of satiety. Another focus of the electrical stimulation may be to interfere with the innate peristalsis of the stomach, which is intended herein to mean to movement of the stomach that typically also acts to break down food and/or moves material towards the antrum or out of the stomach. Another focus is to cause a sensation of satiety by stimulating the stomach, neural tissue of the enteric nervous system and vagal afferent pathway. Another focus is to control the secretions relating to the stomach or hunger by stimulating the stomach.

An embodiment of the electronic circuitry 29 is illustrated in FIG. 1C. The electronic circuitry 29 of the stimulator is located in the housing 21. The electronic circuitry 29 may be in a form of a standardized chip that may be used with one or a variety of sensors, including but not limited to those described herein. The electronic circuitry 29 or similar electronic circuitry may also be included with separately implanted sensors or components of the system. Thus the various components may be configured to communicate with the other components through telemetry or similar signaling.

The circuitry 29 comprises, a microprocessor or controller 40 for controlling the operations of the electronic circuitry 29, an internal clock 41, and battery device 44 such as a pair of lithium iodine batteries for powering the various components of the circuit 29. As such, the controller 40 and battery device 44 are coupled to each of the major components of the circuit as would be apparent to one of ordinary skill in the art. The battery 44 has its output supplied to a DC-to-DC converter 44a to provide a higher voltage, which is utilized for electrical stimulation pulses. The DC-to-DC converter 44a is conventional and provides an output voltage desired for stimulation. The internal clock 41 may also include a real time clock component that communicates with the controller/microprocessor 40. The real time clock component may be used to control stimulation, e.g. by stimulating or allowing stimulation only at a particular time of the day. The real time clock component may also provide a date/time stamp for detected events that are stored as information in a memory device. The memory may be preserved by only saving information corresponding to an event of interest which is saved along with the time/date when the event occurred.

The controller 40 is coupled to stimulation driver 42, which is coupled to stimulating electrodes (e.g., 22, 23) that are used to provide electrical stimulation in accordance with programmed parameters, including in response to sensing conditions relating to the patient or the patient's intake of food as described herein.

Figure 1D:
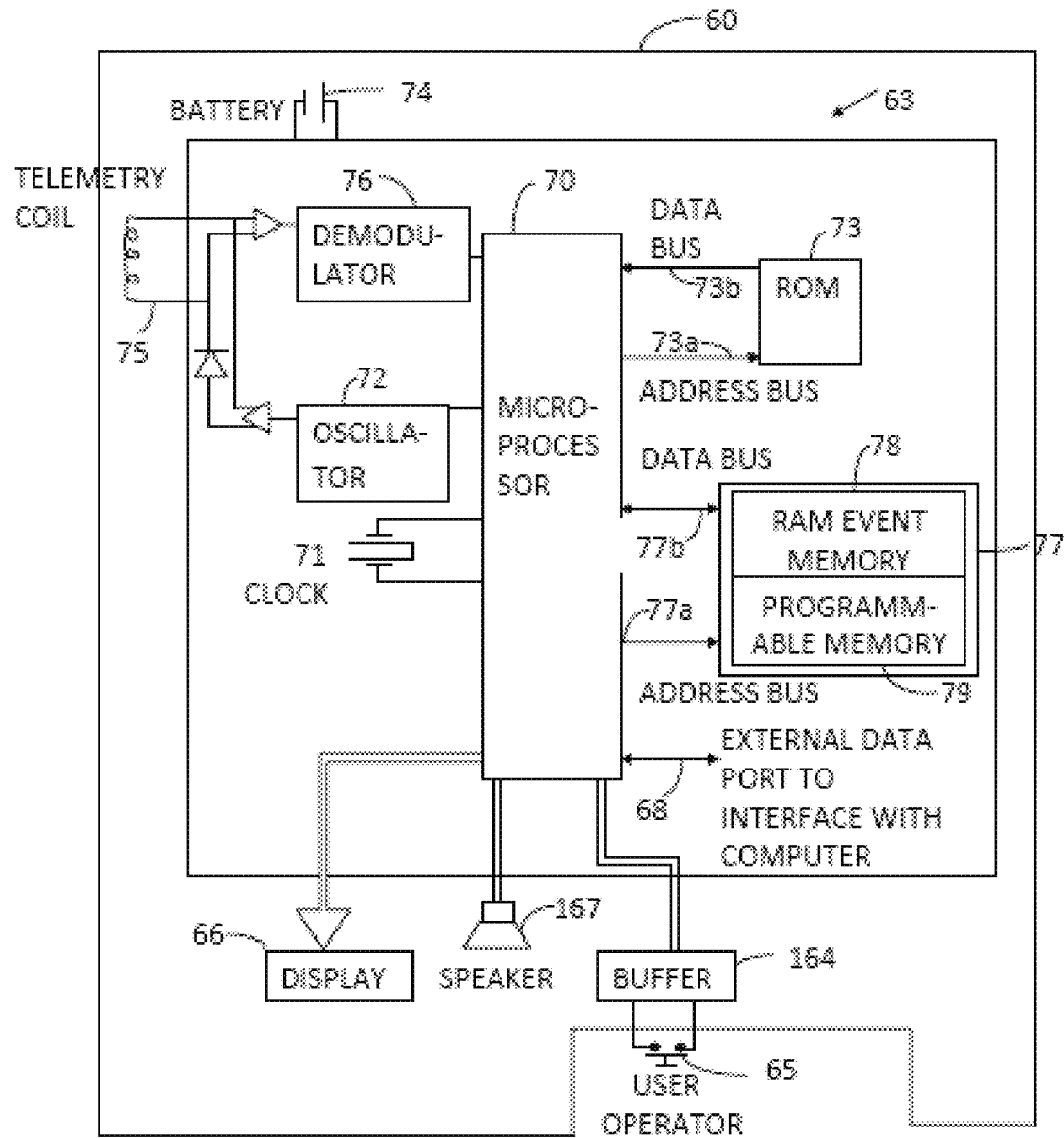

The controller 40 is coupled to ROM 43, which contains the program instructions for the controller 40 and any other permanently stored information that allows the microprocessor/controller 40 to operate. The controller 40 addresses memory in ROM 43 through address bus 43a and the ROM 43 provides the stored program instruction to the controller 40 via data bus 43b. The controller/processor 40 controls the telemetry coil 45, which communicates with an external control or programming device 60 (FIG. 1D), e.g., via a modulated RF signal. Controller/processor 40 is coupled to a buffered oscillator 51 that provides an RF signal to be emitted from the telemetry coil 45. The RF signal is preferably at about 100 kHz-5 Mhz so that the signal is efficiently transmitted through tissue. The controller 40 controls the oscillator 51 and provides data to be modulated with the RF signal. For example, various sensed data such as motion, transmitted or reflected light parameters, pressure, pH, temperature, local muscle contraction, strain, impedance, electrical activity (EMG) etc., may be delivered via a modulated signal through the telemetry coil 45. When the telemetry coil 45 is receiving an external telemetry signal, the buffered oscillator 51 is disabled. Telemetry signals received on the telemetry coil 45 are detected in a detector circuit 51a and communicated to controller 40. The detector circuit may be selected based on the modulation used for the telemetry signals.

The circuit 29 may also be coupled through A/D converters (with amplifiers) 46a, 46b, 46c, 46d to one or more sensors 25, 26, 24a, 24 respectively. The A/D converters convert a representative analog electrical signal from the sensors into a digital signal communicated to the controller 40. Suitable types of these sensors may include but are not limited to the types of sensor described herein. Such sensors at various locations are coupled to the electronic circuit by way of lead wires or through alternative means of communication such as telemetry, wireless communication or indirectly through a separate controller e.g., controller 70 shown in FIG. 1D.

Controller 40 is coupled to RAM 50 via an address bus 50a for addressing a location in RAM 50 and a bi-directional data bus 50b for delivering information to and from RAM memory 50. The RAM memory 50 includes event memory 48 that temporarily stores data recorded by sensors 24a, 24, 25, 26, or electrodes 22 23. RAM memory 50 also includes a programmable memory 49 which may be programmed, for example, by an external programmer 60. The data stored in the programmable memory may include specifications for the electrical stimulation operating modes (e.g., waveform, type of stimulations: for pacing, inducing, interfering with or reversing contraction, for interfering with innate activity, for controlling biochemistry or secretions relating to the stomach, or other types of stimulation, such as neural stimulation) and various procedures or responsive parameters (e.g., for turning on or off various sensing or stimulation functions, parameter modification, protocols or procedures for recognizing various conditions of the patient of the patient's gastrointestinal tract and protocols or procedures for responding to such recognition). These data and procedure/protocol elements, including responsive elements that respond to sensed data, may also be located in whole or in part in other controller devices that may be located independently from electronic circuitry 29. The programming may be done in response to sensed information or, it may be done automatically by an external controller or as desired by a treating physician, etc. Sensed data acquired from the sensors or electrodes, provided to the controller 40 may be stored in event memory 48 in the RAM 50. The data stored in the event memory 48 may be sent intermittently as data bursts via the telemetry coil 45, as opposed to continuously, in order to save battery power. The clock may also mark or date/time stamp the data stored in event memory. The processor also may select events based on predetermined thresholds or characteristics that are to be stored as a significant event, while other events are filtered out and not stored.

The electrodes 22, 23 are coupled through A/D converters 46e and 46f to the microprocessor 40. A/D converter 46e converts the electrical EMG signal sensed by the electrodes 22, 23 into a digital signal representative of the EMG electrical activity, which is delivered to the microprocessor/controller 40 and stored in the event memory 48 in the RAM 50. Also, the A/D converter 46f converts the electrical signal sensed by the electrodes 22, 23 and provided through the impedance circuit 53 described below, into a digital signal representative of tissue impedance, which is delivered to the microprocessor and stored in the event memory 48 in the RAM 50.

The electrode 22, 23 outputs are used to provide electrical stimulation delivered through the stimulation driver 42 to electrodes. The stimulation modes and parameters can either be set using the external programmer 60, or they may be set in response to sensory feedback. The same electrode outputs may be used to sense impedance of the stomach tissue or of the contents of the stomach depending upon the location of the electrodes. Impedance circuit 53 is used to sense impedance and EMG or other electrical activity information is provided to the processor 40 through A/D converter 46e. The electrodes 22, 23 are coupled through coupling capacitors 55a and 55b respectively, to output of electrical stimulation driver 42 and input of A/D converters 46e, 46f.

The impedance circuit 53 comprises a constant current source oscillator 54 that oscillates at a frequency of 50-100 kHz, and A/D converter 46f with an output coupled to the controller 40. The oscillator 54 provides a constant current source through electrodes 22, 23 resulting in a voltage across the electrodes 22, 23 that is representative of impedance, in view of the constant current. The voltage is provided through and is converted by A/D converter 46f to a digital signal representative of impedance. A/D converter 46f has a bandwidth that includes the 50 kHz frequency signal while filtering out the electrical stimulation signal that is delivered to the electrodes 22, 23 through electrical stimulation driver 42, and the EMG signal that is sensed by the electrodes 22, 23. Both of the outputs are filtered out by A/D converter 46f. A/D converter 46e has a bandwidth that filters out the 50-100 kHz signal. Further, when a stimulation signal is being delivered, the controller 40 does not receive signals from A/D converters 46e and 46f Thus the EMG and impedance sensing functions and the stimulation deliver functions may be separated through the electronic circuitry 29, though using the same electrodes.

An additional circuit 58 may be provided in the electronic circuitry 29 comprised of similar components configured like impedance circuit 53. The circuit 58 delivers an interrogating electrical pulse to the electrodes 16, 17 and senses impedance of material between the electrodes. The electrodes 16, 17 are positioned to be in electrical contact with contents of materials that may be in the stomach Additional stimulating sensing electrodes and corresponding signal processing circuits may also be provided.

FIG. 1C illustrates the electronic circuitry 63 for external programmer 60. The electronic circuitry 63 comprises: a microprocessor or controller 70 for controlling the operations of the electronic circuitry, an internal clock 71, and a power source 74 such as battery device for powering the various components of the circuit 63. As such, the controller 70 and battery device 74 are coupled to each of the major components of the circuit as would be apparent to one of ordinary skill in the art. The controller 70 is coupled to a speaker 67 that provides audible alerts and a display 66 such as a CRT to display data such as recorded data, sensed parameters, treatment parameters and status of device (e.g. position or battery charge status). The controller 70 is coupled through a buffer 64 to external input device 65 that is used to provide program parameter input, e.g. from a user, for a user to request data displayed in a desired format through display 66 or speaker 67, or to turn device on and off. The external programmer 60 is also provided with an external data port 68 to interface with a computer and provide a means for bi-directional communication of data or commands. The computer may provide programming or data to the controller/microprocessor 70. A user may also interface with the computer to provide treatment protocols or changes in protocols, etc. Also, a user may control the turning on and off of the stimulation program.

The controller 70 is coupled to ROM 73, which contains the program instructions for the controller 70 and any other permanently stored information that allows the microprocessor/controller to operate. The controller 70 addresses memory in ROM 73 through address bus 73a and the ROM 73 provides the stored program instruction to the controller 70 via data bus 73b.

The transceiver comprises a telemetry coil 74, an oscillator 72 and an A/D converter 76. The controller 70 controls the telemetry coil 75, which communicates with stimulator electronics 29 (FIG. 1B) through its telemetry coil 45. Controller 70 is coupled to an oscillator 72 that provides an RF signal, preferably having a characteristic frequency of 500 kHz or higher, to be emitted from the telemetry coil 75. The controller 70 controls the oscillator 72 and provides data to be modulated with the RF signal, for example, programming information, stimulation parameters, etc. The telemetry coil 75 also receives information transmitted via RF signal from telemetry coil 45 on the stimulator 10 such as various sensed data, e.g., temperature, pressure, pH, impedance of the stomach or of its contents, optical characteristics of stomach contents, motion data, electrical activity (EMG), etc. The received RF signal is passed through A/D converter 76 and is transmitted to the controller 70.

The data is delivered to the event memory 78 in RAM 77 by way of data bus 77b for temporary storage. The data may be retrieved from RAM 77 by addressing the storage location via the address bus 77a.

Event memory 78 temporarily stores data sensed by sensors 24a, 24b, 25, 26, or electrodes 22, 23; recorded through controller 40; and delivered via telemetry to the external programmer 60. The data may then be downloaded onto a computer using the external data port 68. The RAM 77 also includes a programmable memory 79 which may be programmed, for example, to specify operating modes such as waveform, frequency, pulse width, amplitude, repetition rate, etc. which programming is then telemetrically communicated to the stimulation device 20. The modes and parameters can either be set using an external programmer 60 and/or set in response to sensory feedback according to programs.

The stimulator 20 may be programmed to deliver electrical stimulation in response to sensed parameters. The sensors 24a, 24b, 25, 26, or electrodes 22, 23, depending upon their specific location, may comprise (but are not limited to): a temperature sensor that may sense a change in temperature or a rate of change in temperature that indicates ingestion of food or liquid; a pH sensor that may be used to determine when food has been ingested; an optical emitter/sensor that may be used to determine the presence and/or composition of food; a pressure sensor that may be used to sense motility patterns, e.g. presence, strength or frequency of contractions and presence of food or drink bolus at the location of or passing through the band; a contractions sensor that may provide information on stomach contractions and local responses to stimulation; an impedance sensor that may provide information on the content of the stomach and amount of stretch of the stomach wall and/or an electric sensor that may determine when a characteristic EMG pattern that represents meal stages, nausea and autonomic nervous system status; a motion sensor that determines an activity level or wakefulness of a subject; a biochemical sensor that provide information on biochemical compositions relating to the stomach such as secretions.

The responsive devices may comprise at least one sensor and at least one responsive element. From sensed information, the responsive element determines the existence of a condition, e.g., presence of food; ingestion of food; type of food ingested; activity level of a subject; wakefulness of a subject; time of a daily cycle or schedule; contractions of the stomach, stress level, nausea, etc.

The responsive element may combine a number of sensed parameters to determine the existence of a condition or circumstance or a probability of the existence of a condition or circumstance. The responsive element may thereupon determine a course of treatment, including protocols, stimulation parameters and whether or not to stimulate. In one variation responsive element may respond by stimulating to interfere with the stomach contractions; to slow, stop or reverse the innate peristaltic contractions that tend to move food through the stomach.

For example, the combined determination of temperature changes indicating likelihood of food ingestion, and an accelerometer indicating that a subject is not sleeping or is not highly active may trigger a responsive element to stimulate the stomach to retain food for a predetermined period of time. The accelerometer can determine a low level of activity indicating likelihood of a sleep state, but may be overridden by a temperature sensor sensing that food has been ingested and thus requiring stimulation. PH may be used in a similar manner as temperature to indicate a likelihood of food ingestion. A timer may also confirm the likelihood that food is being eaten given the time of day, or may refrain from stimulating in spite of food being ingested if it is a certain time of day, e.g., when the stomach is naturally cleaning out as it typically does during the night.

The responsive element may receive input from one or more sensors and, in response, the responsive element may interrogate another sensor for information to determine a course of action. This may be used to save battery or power consumption. This may also be used to confirm the existence of a condition or circumstance using more than one sensor. For example, one or more sensors may provide information that food has been ingested. Upon making this determination, another sensor may be triggered to determine what type of food has been ingested. For example, an impedance sensor may determine characteristics of the content of the stomach by measuring the impedance of the contents of the stomach. An optical emitter/sensor may sense the light reflectance/transmission characteristics of contents of the stomach. This information may be recorded in a memory device and downloaded. Also the information may elicit a simulation response controlled by the responsive element when a certain type of food is detected. In addition foods may be provided as part of an eating regimen that have markers for different types of food. Gastric retention of some foods may be created while permitting movement of others out of the stomach.

As shown in FIG. 1A, the sensor 928, desirably a pressure sensor, may be mounted in fluid communication with port 904. FIGS. 2A-2C illustrate alternative embodiments of system 900. FIG. 2A shows sensor 928 coupled to the fluid-filled cuff 903, the housing 920, circuitry 922, and battery 924 are also attached to the lap band 902. FIG. 2B shows sensor 928 coupled to the fluid filled cuff 903, while housing 920, circuitry 922 and battery 924 are located outside the lap band 902, optionally attached to the implanted port 904.

FIG. 2C shows an embodiment of system 900 comprising at least two sensors 926. Pressure sensor 928 may be coupled to the fluid-filled cuff 903. The second sensor 926 may comprise a temperature sensor 927 penetrating the stomach wall, coupled to the housing 920 or to the fluid filled cuff 903 and pressure sensor 928 (not shown). This embodiment is particularly suitable when the sensor 928 must collect data from inside the stomach. In an alternative embodiment the second sensor 926 may comprise a sensor attached to the outside of the stomach 925, coupled to the housing 920 or to the fluid filled cuff 903 and pressure sensor 928 (not shown). In yet another alternative embodiment, system 900 comprises a combination of at least three sensors 928, 927, and 925, as described above.

FIG. 2D shows an embodiment of system 900 comprising two pressure sensors 928 coupled to the fluid-filled cuff 903.

One pressure sensor 928 may located above the fluid filled cuff, to measure the pressure above the lap band, and the other may be located below the lap band to measure the pressure in the stomach, below the level of the lap band.

FIG. 2E shows an alternative embodiment of system 900 comprising at least two lap bands, each lap band comprising at least one sensor 926. The lap bands may comprise different elasticities and each lap band's elasticity may be changed dynamically. The superiorly-located lap band may be used to reduce food intake and sense ingestion events with the at least one sensor. The inferiorly-placed lap band may be used primarily for sensing purposes with the at least one sensor. Since the inferiorly-placed lap band may not be inflated, it may need to be fixed in its desired location with seromuscular sutures such as the MiniMizer Extra from Bariatric Solutions, or other means known in the art. If the superiorly-placed band is not fully inflated, it may also need to be fixated using seromuscular sutures, or other means known in the art. The dual lap band set-up may also comprise other sensors, such as for example a combination of optical sensors that can measure ingestion velocities in the lower esophagus and upper portion of the stomach.

FIG. 2F shows an alternative embodiment of system 900 comprising a sensor support extending through a wall of the gastric pouch 910 so as to support a sensor within the pouch and a lap band 902 comprising at least two electrodes exposed radially inwardly of the lap band to provide electrical stimulation to the portion of the stomach in contact with and/or constrained by the lap band. Through the electrodes 907 placed inside the lap band, the implanted device may be capable of electrical stimulation for therapy delivery to an appropriate portion of the stomach wall. For example, electrodes may be placed inside the tissue-supporting structure of the lap band, to provide electrical stimulation to the portion of the stomach in contact with the lap band. Alternatively or additionally, electrodes may also be placed on the multifunctional transgastric probe 2000, suture tabs of the lead body (not shown), or active can/stimulator housing (not shown). The electrodes can be intramuscular or surface, uni-polar or bi-polar, and with or without high surface area coating. The gastric electric stimulation functions and sensing functions of the embodiment may share the same lead wires 909. The gastric electric stimulation and sensing electrode configuration can be determined by the patient's visceral response and/or therapy results. Electrode configuration includes the number of selected electrodes and their respective implant locations, stimulation vectors and sensing vectors. Gastric impedance and/or its derivatives between the gastric band electrode 905' and the transgastric probe return electrode 905 on the pouch can be used to measure the state of the gastric pouch including its relaxation or distension, the presence or absence of gastric motility, the presence or absence of acid, the activity state of muscle or nerve fibers. Signals from the sensors on the multifunctional transgastric probe 2000 will trigger therapy, with the therapy type dependent on the classification of the event derived from analysis of the signals.

In another embodiment, the lap band shown in FIG. 2F may be only partially inflated, to minimize the side effects such as nausea and vomiting; the partial inflation of the lap band will physically restrict the food intake to a certain extent, while the electrical stimulation to further curb the patient's appetite. A patient will be able to achieve substantial weight loss with minimal side effects.

Food and Drink Intake Detection

Figure 3A:
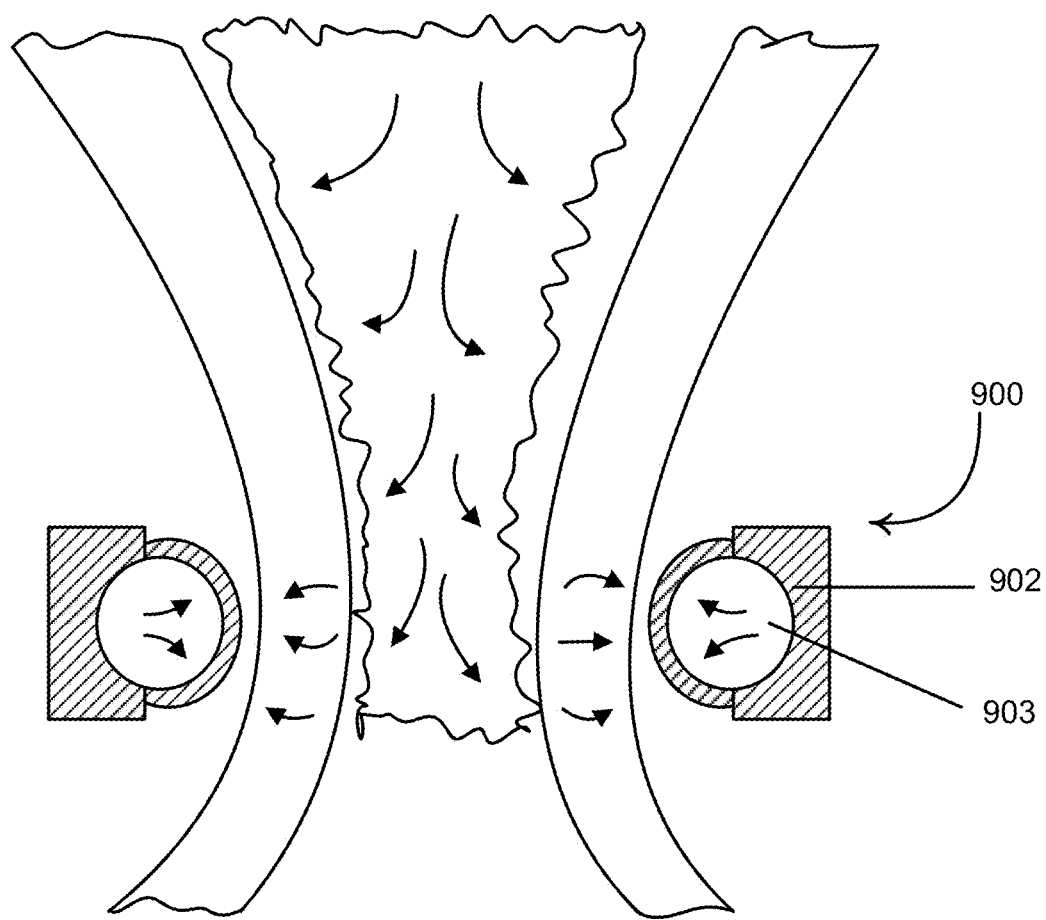
FIG. 3A shows a cross-sectional view of the superior portion of the stomach constricted by a lap band 902 with a fluid filled cuff 903.

FIG. 3 illustrates ingestion of food or drink into a stomach. As food intake occurs pressure increases within the lap band, in the upper portion of the stomach and in the lower esophagus. The lower esophagus and upper portion or the stomach will expand to accommodate the incoming food as shown by dashed lines in FIG. 3. FIG. 3A shows a cross-sectional view of the superior portion of the stomach constricted by a lap band 902 with a fluid filled cuff 903. The lap band restricts the perimeter of the stomach, thus slowing down the passage of the food through the stomach. Following ingestion, food moves down the esophagus to the superior portion of the stomach, accumulating above the lap band placing an increasing amount of pressure on the lap band, as well as the upper portion of the stomach (gastric pouch), and lower portion of the esophagus. This accumulation of food and the accompanying increase in pressure on the lap band will occur up to a certain point, then peristaltic action will push the food through the band, thereby causing a drop in pressure.

Figure 4A:
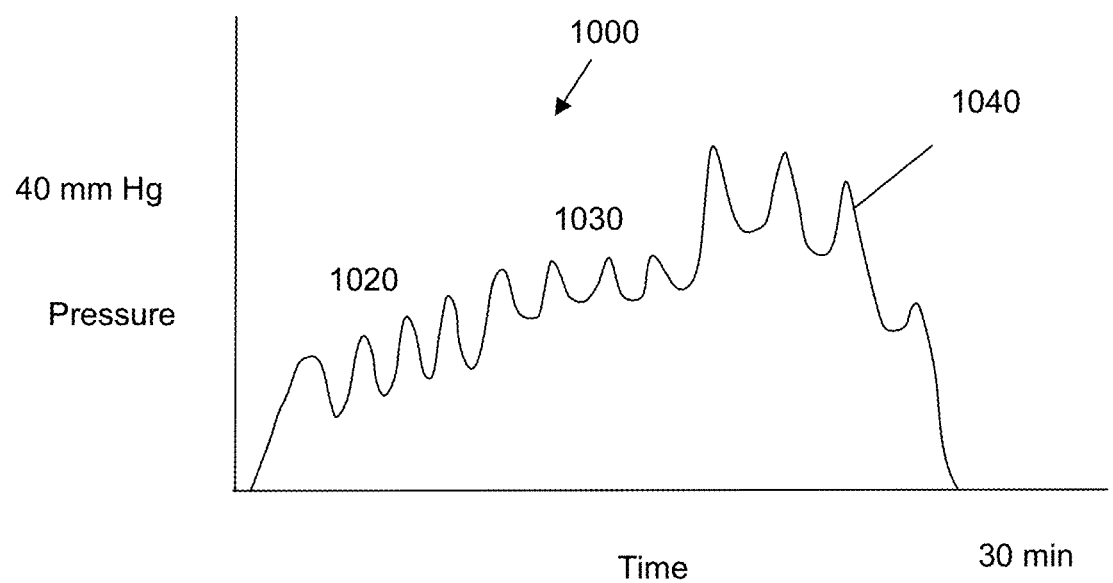
FIGS. 4A-4C show the pressure waveforms from pressure sensor signals one might expect with food or drink input. More specifically.
Figure 4B:
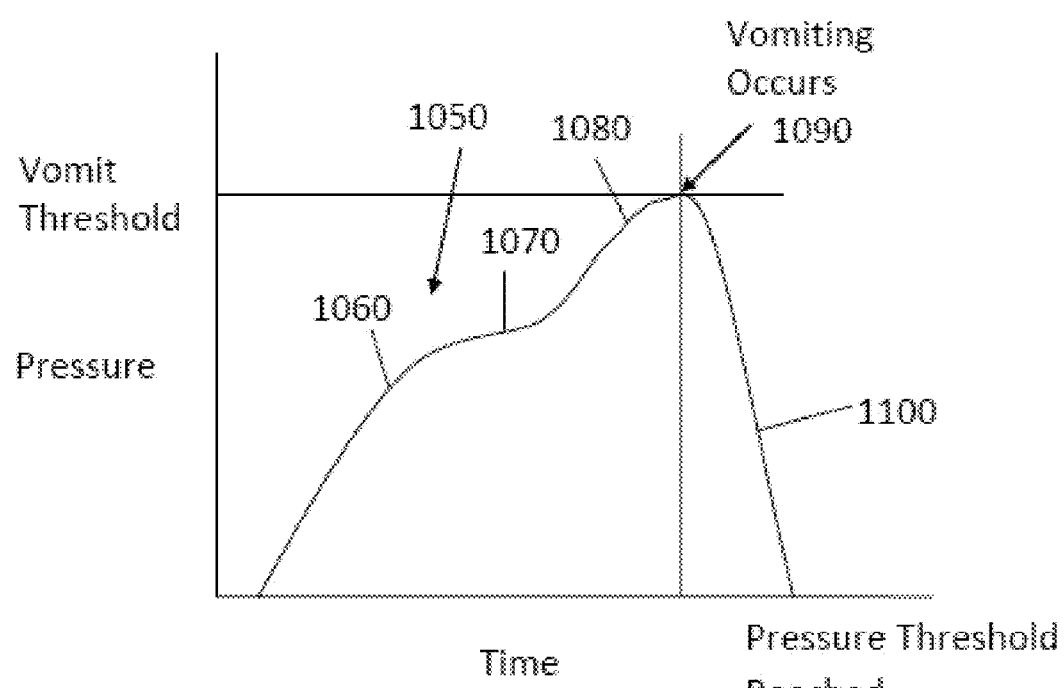
Figure 4C:
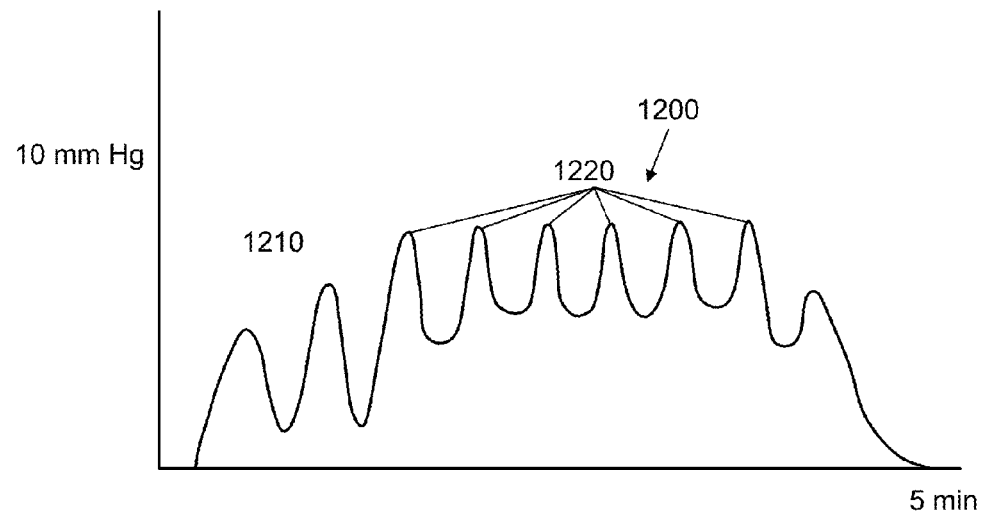

FIGS. 4A-4C show the pressure waveforms from pressure sensor signals one might expect with food or drink input. FIG. 4A shows the expected pressure waveforms from an ingestion of food 1000. With each swallow of solid food the pressure on the band increases (1020). As the food fills up the gastric pouch, the lower esophagus peristaltic waves are initiated in the esophagus and stomach to push food through the narrow opening created by the band. If the food is solid and dry, the digestion and peristaltic action on the food will not be enough to push the food out as fast it is entering the stomach. At this point the patient will feel severe discomfort and be forced to stop eating, or a vomiting reflex may occur, and maximum pressure is seen at the band (1000). After a delay, the peristaltic waves eventually empty the gastric pouch and baseline pressure will be again detected at the band (1040).

FIG. 4B illustrates an overeating event; as food is ingested the pressure increases moderately 1060 until a plateau is reached 1070. However, when overeating occurs, the increased food intake beyond the volume of a normal ingestion event increases the pressure at the band and proximal portion of the stomach to a much higher level 1080. This high pressure sets off the vomiting reflex 1090; after vomiting and the pressure rapidly decreases 1100 with the emptying of the proximal portion of the stomach.

FIG. 4C shows the expected pressure waveforms 1200 from a drinking event. Compared to the expected pressure wave forms from ingestion of a solid, upon ingestion of a drink 1210, there will be less buildup of pressure because liquid passes through the band with little resistance. However, there will be transient pressure increases 1220 with each swallow of liquid, as the increase in volume will temporarily expand the small upper portion of the stomach; the transient increase will depend on the rate of intake. Furthermore, since the liquid can exit the proximal portion of the stomach rapidly, it is unlikely that drink intake will be so fast as to cause the pressure to increase to such an extent that a vomiting reflex would occur.

The differences in pressure waveforms between a normal eating event and a drinking event can be distinguished by the processor. Drinking events will look like multiple positive pressure transients with a return to baseline pressure very quickly after each transient (nominally less than 30 sec). While an intake of any significant volume of solid food (>20 ml) will lead to an increase in pressure that lasts multiple minutes (5-30 min). In addition because of the pressure put on the gastric pouch and lower esophagus during the intake of solid foods, peristaltic waves will cause large pressure transients at the band, on the order of 10's of mm Hg. An increased pressure that lasts at least 5 minutes, but not more than 60 minutes will very likely be interpreted as an ingestion of a solid; whereas, an increased pressure that lasts at on the order of 10 sec to 2 minutes will very likely be interpreted as an ingestion of a liquid. The determination of food versus drink can be based on maximum pressure amplitude and duration. These results of the food intake diagnostics can be provided to the patient or physician in order to show compliance or lack of compliance with dietary instructions.

Figure 5:
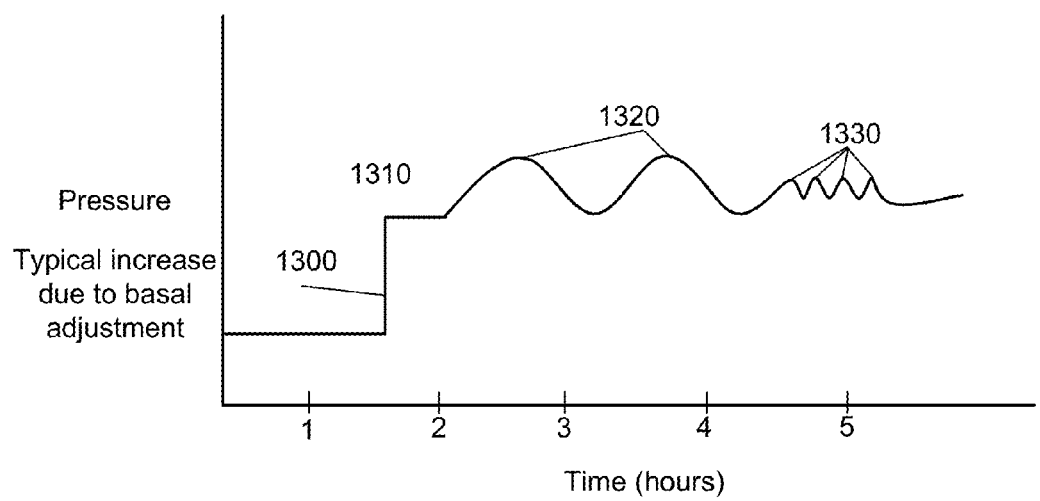
FIG. 5 shows the pressure waveforms 1300 that occur with injection of fluid, e.g. saline, into the port of the lap band.

FIG. 5 shows the pressure waveforms 1300 that occur with injection of fluid, e.g. saline, into the port of the lap band. The baseline pressure 1210 increases as fluid is injected into the port. The increase in fluid (saline) volume expands the elastic portion of the port so that it creates a smaller diameter for food to pass through, which leads to an increase in pressure 1320 upon ingestion of food. The pressure changes caused by eating events with eating events 1320 or drinking events 1330 will manifest themselves on top of the baseline pressure. However, this baseline pressure change may be transient as the volume of the lap band may adjust to accommodate the saline. The occurrence of pressure transients due to peristaltic waves following drink intake, may indicate that the band is too tight. These peristaltic waves may be detected at the band and lead to automated adjustment of the band to reduce pressure.

Figure 6:
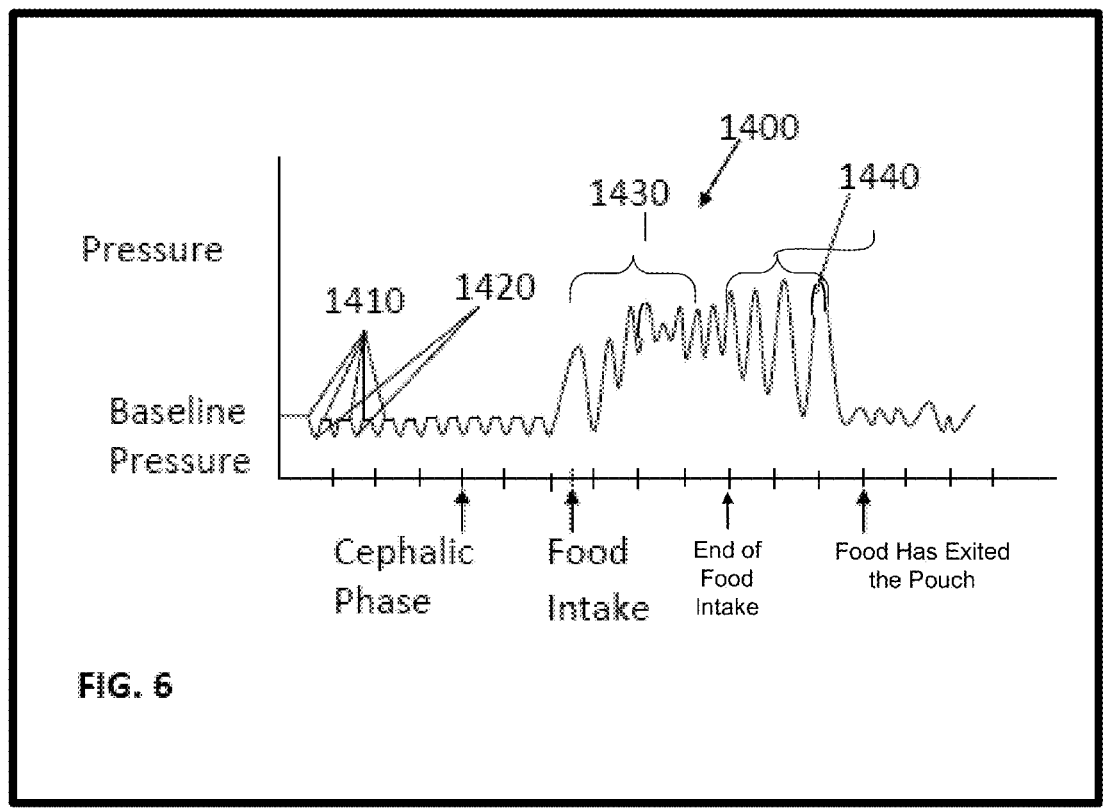
FIG. 6 shows pressure waveforms from peristaltic waves 1400.

FIG. 6 shows pressure waveforms from peristaltic waves 1400. Slow waves or peristaltic action in the stomach that is always present, is seen as low amplitude pressure waves at a frequency of about 3 per minute 1410. The peristaltic contraction is seen as a reduction in pressure at base 1420. After food intake occurs, the baseline pressure increases and pressure transients due to swallowing and peristaltic action are seen riding on the baseline change. As food intake continues, the pressure at the band and gastric pouch increases and the pressure transients due to peristalsis increase in amplitude and frequency. As the bolus moves forward, the pressure decreases behind it. FIG. 6 shows the initial small transient pressure increases due to peristaltic activity. The peristaltic waves that occur without the presence of food cause little or no pressure change. However, beginning at the cephalic phase, and when food or liquid enters the stomach the peristaltic waves would cause pressure waves of amplitude and duration that is proportional to the amplitude and duration of the peristaltic wave 1430. The peristaltic activity at the end of the meal is higher in order to push the food out of the stomach towards the small intestine, pressure undulations 1440 caused by these peristaltic waves will occur as the pressure recovers to the former baseline.

Pressure waves due to peristaltic activity need to be differentiated from pressure waves due to food intake. In the case of a pressure sensor on the lap band these pressure waves can be differentiated because of their higher frequency and the amplitude of the pressure transients is significantly higher than the overall increased pressure waves due to food intake.

Optionally, temperature, optical, impedance, pH, or acoustic sensors signals may also contribute data to be used in food and drink intake detection. In one embodiment, temperature sensors can detect rapid changes in homeostatic temperature within the stomach cavity. The rapid changes in homeostatic temperature can be used to detect ingestion events, and in particular, ingestions of liquids. In another embodiment, impedance spectrometers could determine water content, acidity or other through the measure of impedance of materials; optical spectrometers may determine the composition of ingested matter (i.e. sugar, carbohydrate, and fat content); pH sensors may determine the ingestion of water and other food through changes in acidity from baseline, and acoustic sensors may detect sound waves as each swallow occurs, and as a food bolus passes through the lap band, etc. As shown in FIG. 2F, in yet another embodiment gastric impedance and/or its derivatives between an electrode on the band 905' and the trans-gastric (probe) return electrode 905 on the pouch can be used to measure the state of the gastric pouch including its relaxation or distension, the presence or absence of gastric motility, the presence or absence of acid, the activity state of nerve fibers. This measurement can be used to determine intake of food or drink or both.

Remote Communication:

Remote communication with the system 900 will allow the use of an automated patient support system that would allow coaching type feedback with regards to their activity and food intake, U.S. Patent Application Ser. No. 61/166,636.

In some embodiments, an electrical conduit extends from a temperature sensor within the stomach, through a transgastric port, and to circuitry 922. This electrical conduit or lead could, but need not have any stimulating electrodes. Suitable trans-gastric temperature sensing probes and ingestion analysis may described in (or may be modified from those described in) U.S. Provisional Patent Application No. 61/122, 315, filed on Dec. 12, 2008, the full disclosure of which is incorporated herein by reference, and U.S. patent application Ser. No. 12/637,452 filed on Dec. 14, 2009.

Food or Drink Classification:

The pressure waveforms from food 1000 and drink ingestion 1200 can provide input to a food and drink selection algorithm. The food or drink classification may be based on slope, maximum deviation from baseline, or other signal characteristics of the pressure waveform. When food intake occurs, diagnostics are stored based on the timing and duration of the intake and magnitude of pressure change. The diagnostics may be used in monitoring patient's weight loss therapy.

As shown in FIGS. 2D and 2E, pressure sensors may collect pressure readings above and below the restriction created by the inflated lap band. The two pressure readings may be used to classify the ingestion event: for example if the pressure reading above the restriction is higher than the one below, the ingestion will be classified as a solid; if the pressure reading above the restriction is lower than the one below, the ingestion will be classified as a liquid or an attempt to cheat the lap band by blending solid food with a liquid to bypass the restriction of the lap band.

Figure 9:
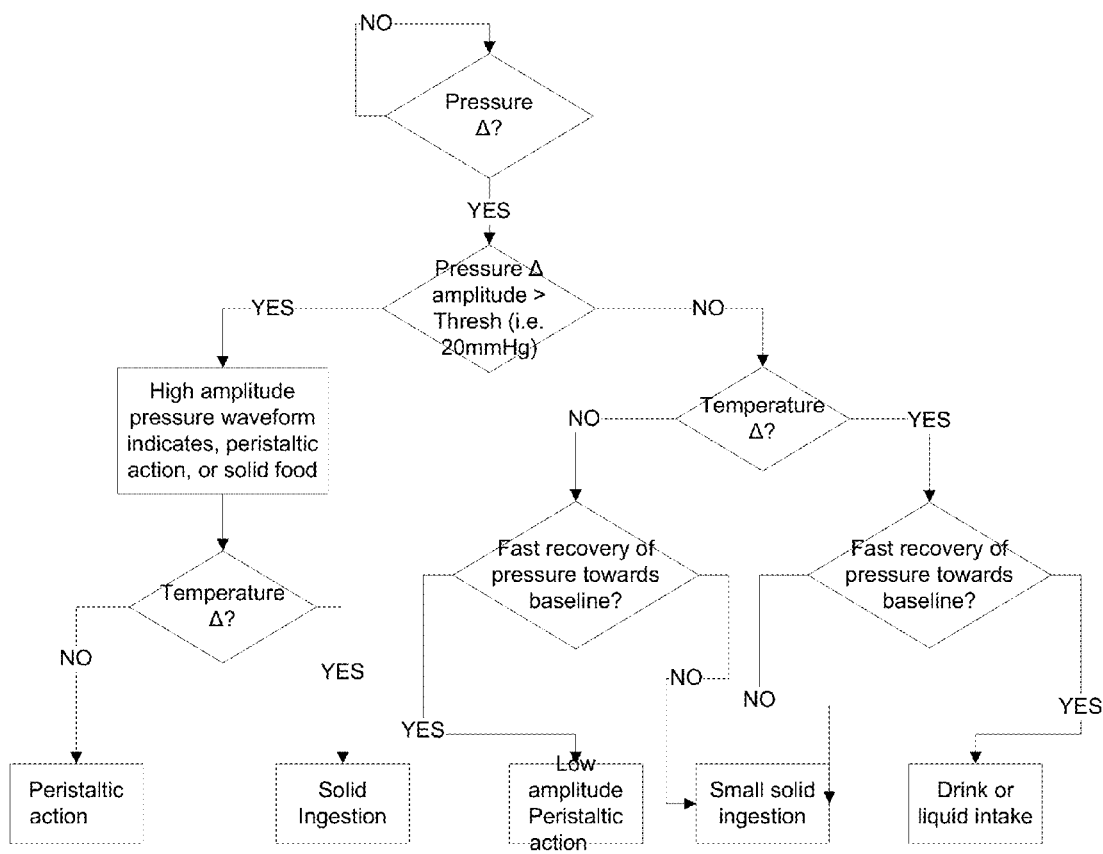
FIG. 9 schematically shows a system and method for classification of ingestion events based on signals from a pressure and a temperature sensor.

As shown in FIG. 9, signals from a combination of pressure sensor and a temperature sensor may be used to improve the accuracy of the food detection algorithm. A pressure wave sensed at the lap band may be classified with the help of a temperature sensor that can measure changes in the temperature of the contents of the gastric pouch at the above the lap band. The meal classification is based on known characteristics of the pressure waves due to food intake, liquid/drink intake and an esophageal peristaltic wave. The pressure increase due to food intake is higher than that for drink intake, because the food must break down in order to pass through the small opening created by the lap band, and very little passes through immediately. Conversely with liquid intake, a smaller pressure increase occurs due to the immediate passage of the drink through the lap band. Peristaltic action can cause very large pressure waves, particularly at the end of a meal as the esophagus and stomach work to pass the solid food through the stomach to the small intestines. The esophageal peristalsis working to push the food down through the stomach will be most noticeable at the lap band. High esophageal peristalsis occurs when the gastric pouch becomes full. One way to differentiate these pressure waveforms due to peristalsis from food or drink intake is the downward slope of the pressure waveform, the other is temperature, because most new intake will cause a temperature change in the gastric pouch.

For example, a change in pressure, based on a predetermined threshold above the "noise floor", is detected and the amplitude of the pressure change is compared to a threshold level. If the amplitude is greater than the threshold level, then the temperature sensor is used to determine if that pressure wave was due to peristaltic action, without temperature change, or a solid ingestion, with a temperature change. If the amplitude of the pressure waveform did not meet threshold, then a temperature change indicates a small solid food, or drink intake; a fast recovery of the pressure waveform will likely indicate a drink or other liquefied intake, while a slow recovery would likely indicate a small solid food ingestion. No temperature change indicates low amplitude peristaltic action or a small solid food ingestion, depending on the rate of recovery of the pressure waveform. A very slow recovery to the baseline will likely be due to some intake, even without an observable temperature change, because the temperature sensor is less sensitive once the gastric pouch is full, and some food intake can be very close to body temperature once it arrives in the gastric pouch.

Figure 9A:
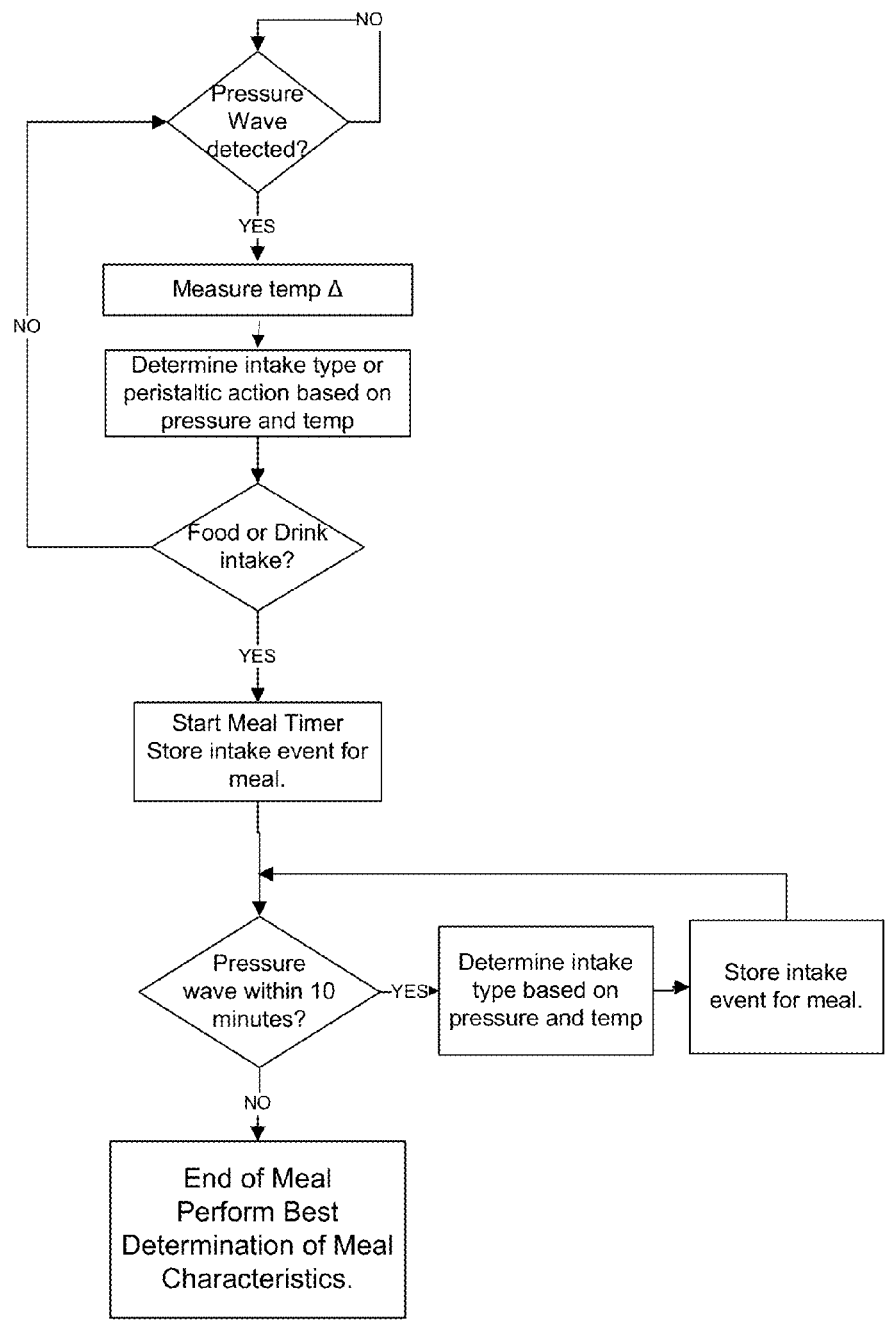
FIG. 9A shows an algorithm for determining the type of meal ingested and its duration based on signals from a pressure and a temperature sensor.

FIG. 9A shows an algorithm for determining the type of intake ingested during the meal and its duration based on the multiple pressure waveforms that occurred during that meal. The meal duration is calculated starting at the first detected intake. A pressure wave attributed to peristaltic action returns the algorithm to the start, and waits for another detected pressure wave. Once a detected pressure wave and accompanying temperature change indicate a food or drink intake, the meal timer is started and the algorithm waits for additional pressure waves to be detected within a certain frame of time (i.e. 10 minutes). Additional pressure waves occurring within that time frame are assumed to be part of the same meal. A meal may consist of multiple pressure waves indicating either food or drink, and also peristaltic action.

At the end of the meal, the algorithm then makes a best determination of the meal characteristics. The data obtained could indicate that it was a long meal, and the amount of peristaltic action following the meal could indicate the level of protein or fat in the meal. Strong peristaltic action at the end of the meal may indicate that the gastric pouch was over-full. The proportion of drink versus solid intake can also be determined to understand if the patient's intake behavior is appropriate. The duration of the meal, and proportion of solid versus liquid may lead to a rough calorie estimation.

Figure 10:
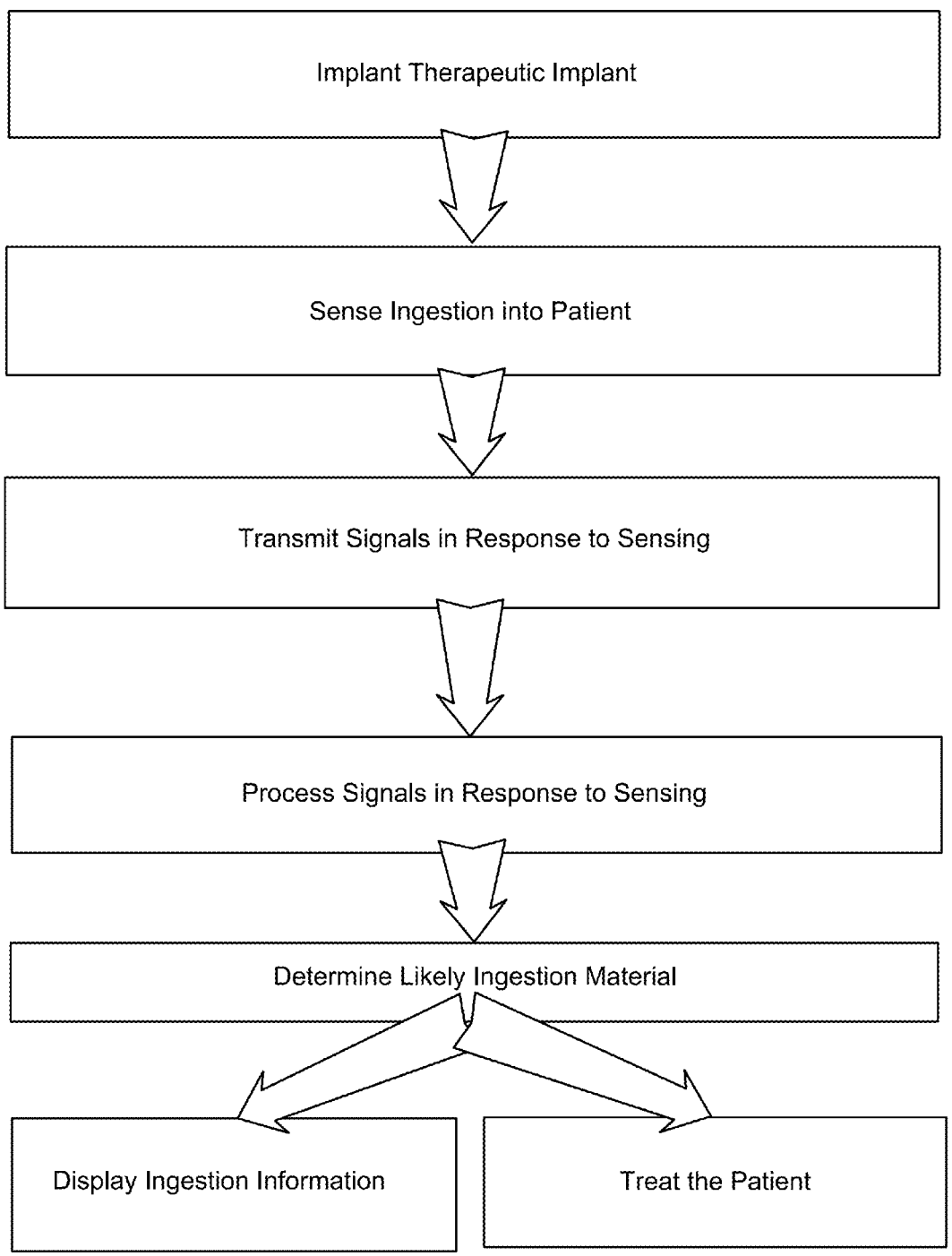
FIG. 10 shows an alternative treatment method comprising the therapeutic implant and the multifunctional transgastric probe.

Ingestion Material Classification:

As shown in FIG. 10, signals from one of, some of, or all of the impedance spectrometer, temperature sensor, distention sensor, and color detector may be used in an algorithm to classify the ingested material. Thus the pH data provided by the impedance sensor can be used to determine potential food materials. The data regarding temperature change over a certain amount of time can be used to classify the ingested material as a solid or liquid. The amount of distention created in the gastric pouch can further be used to classify the ingested material as a solid of liquid. The color detector data can be used to determine whether there has been an ingestion event, whether the ingested material is solid, and whether the ingested material is a translucent liquid. Used in combination, the four types of data can provide likely ingestion material candidates.

In one embodiment, the color detector data will be used to determine whether there has been an ingestion event, whether the ingested material is nontranslucent solid, and whether the ingested material is a translucent liquid. The data regarding temperature change over a certain amount of time and the amount of distention created in the gastric pouch will be used to classify the ingested material as a solid or liquid. Once the existence and the phase (solid, liquid, or a combination of solid and liquid) of an ingestion event have been established, the pH data provided by the impedance sensor or optical analysis of near intra-red bands can be used to determine potential food materials. The potential food materials will then be displayed as feedback to the patient and/or the patient's physician.

Caloric Determination:

The detection of these peristaltic waves by the pressure sensor in the lap band sensor system may aid in the determination of caloric or fat content of a meal. Fat and protein chemodetectors in the small intestine provide feedback information through a vagal pathway that controls the amplitude and duration of the peristaltic activity in the stomach and increases the duration of time the food spends in the stomach. The main contractions occur in the antral portion of the stomach, so they may be detected easier with an intragastric balloon, but as the stomach empties the strong peristaltic activity rises higher towards the body of the stomach and these changes could be sensed by a pressure sensor located in the lap band.

Lap Band Adjustment:

Individual ingestion events or ingestion patterns will trigger various therapeutic approaches. In alternative embodiments, the food and drink intake data may be used to trigger automatic tightening of the lap band upon detection of an ingestion event.

In other embodiments, the implanted device may be capable of electrical stimulation for therapy delivery to an appropriate portion of the stomach wall. For example, electrodes may be placed inside the lap band, to provide electrical stimulation to the portion of the stomach in contact with the lap band. In this case, the pressure waveforms will trigger therapy, with the therapy type dependent on the classification of event.

In another embodiment, the lap band may be only partially inflated, to minimize the side effects such as nausea and vomiting; the partial inflation of the lap band will physically restrict the food intake to a certain extent, while the electrical stimulation to further curb the patient's appetite. A patient will be able to achieve substantial weight loss with minimal side effects.

In one embodiment the lap band sensor system is capable of automatically adjusting the lap band. The pressure signal could be used to automatically determine when a band adjustment is needed. The adjustment may be based on the baseline pressure level, so that the band could be adjusted to stay at a target level. In a further embodiment, the lap band sensor system may comprise an algorithm to relieve pressure on the lap band for certain periods during the day, between meals and/or at night, to avoid erosion and pressure damage to the stomach tissue under the band. The pressure signal may be useful for detecting pre-vomiting and optimizing lap band adjustment.

Activity Sensors:

System 900 would optionally include a 3D accelerometer and/or a heart rate sensor. This sensor would provide feedback to the patients as to whether they are meeting their activity and exercise goals. Further, these sensors would provide estimates as to the number of calories burned in during exercise and/or total daily energy expenditure, as disclosed in U.S. Provisional Patent Application No. 61/241,154 which is hereby incorporated by reference. The activity sensor(s) may allow therapy adjustment, such as loosening of the gastric band and lessening the intensity or stopping electrical stimulation, during exercise sessions and for a period after exercising, to encourage good hydration after exercising and reward patients for healthy exercise. The amount of loosening of the gastric band may be proportional to the exercise intensity and duration.

The accelerometer data may also reduce the tightness of the lap band when sleep is detected. This may reduce the side effects that have been associated with lap banding, such as acid reflux.

Intragastric Balloon Sensor System:

An alternative embodiment includes a intragastric balloon system 1500 having sensors and telemetry circuitry suitable for implantation in the stomach cavity, endoscopically deployed stimulation systems having sensors and telemetry circuitry suitable for implantation in the stomach cavity, and the like. The intragastric balloon may comprise any such balloon currently marketed or available in clinical trials, as for example, the BioEnterics® Intragastric Balloon (BIB®) System of the dual intragastric balloon developed by ReShape Medical™ Inc.

Figure 7:
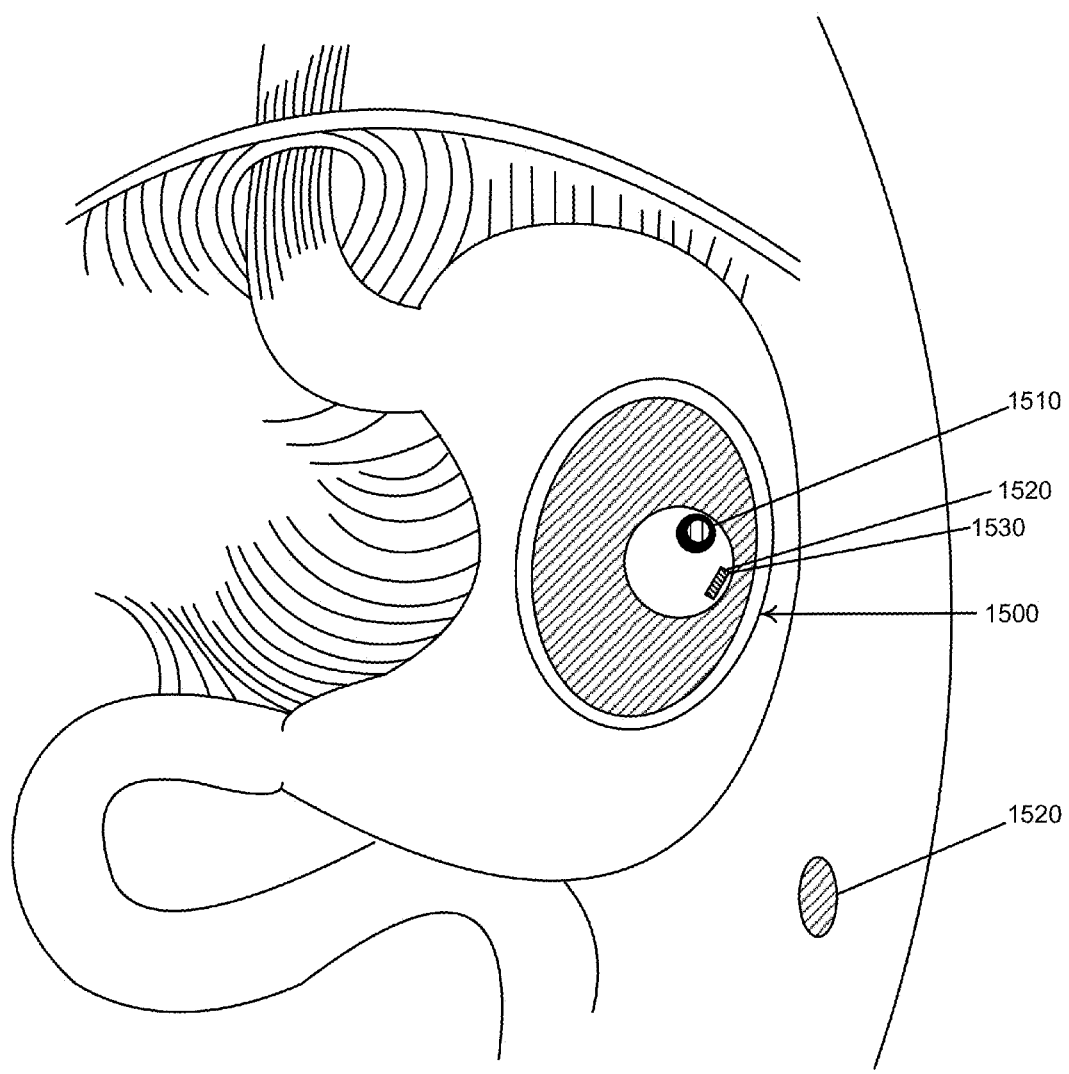
FIG. 7 shows an exemplary intragastric balloon-sensor-monitor system 1500.

FIG. 7 shows an exemplary intragastric balloon-sensor-monitor system 1500. The sensor-monitor device 1520 may be used in conjunction with an intragastric balloon 1510. In this case the sensor-monitor device 1520 could be inserted within the balloon so that when the balloon is filled with saline inside the stomach, the device would be enclosed within the balloon. The sensor-monitor device will comprise a sensor 1530; the sensor may comprise a pressure sensor that would pick up pressure changes within the balloon.

Pressure changes that occur outside the walls of the balloon will change the internal pressure of the balloon since the material of the balloon is compliant. In an alternative embodiment, the intragastric balloon-sensor-monitoring system 1500 comprises a monitoring device placed outside the balloon, where a pressure sensor 1520 is attached to the surface of the monitoring device.

Other sensors, such as pressure sensors (e.g. a MEMS-type, strain-gage, etc.), temperature, pH, acoustic, optical sensor to detect food or drink intake and/or activity sensor, such as an accelerometer, heart rate sensor, and/or a core body temperature sensor. The at least one sensor may be wired to the sensor-monitor device 1520, or communicate wirelessly with the processor in the housing.

Sensors Used with Other Type of Stomach Reduction/Bypass Surgeries:

In the case of gastric bypass and stomach reduction surgeries, the monitoring device could be implanted at the time of surgery, potentially at one of the incisions used as a port for the laparoscopic tools.

The sensors and monitoring device may also be used in conjunction with a cardiac device or insulin pump who have cardiac problems or diabetes as a co-morbidity with obesity.

Figure 8:
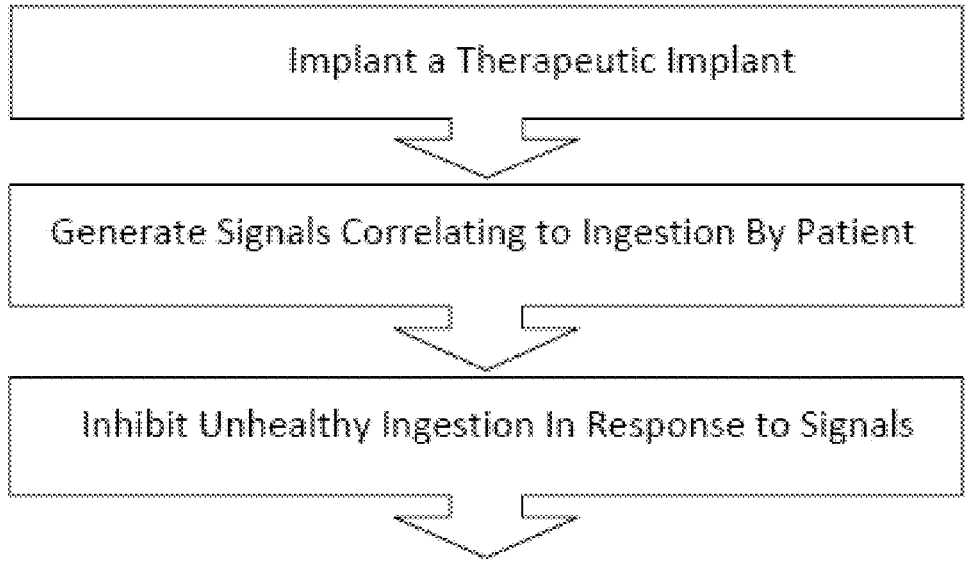
FIG. 8 shows a method of treating a patient with an unhealthy ingestion pattern 2000.

Method of Treatment:

FIG. 8 shows a method of treating a patient with an unhealthy ingestion pattern 2000. A therapeutic implant comprising a gastric band sensor system or an intragastric balloon sensor system 2010 is implanted into a patient. The sensor(s) in the system will sense ingestion by the patient and generate signals correlating to the ingestion 2020. Ingestion deemed unhealthy will be inhibited 2030. For example, patients are given behavioral guidelines to maximize solid food ingestion, and not to drink high calorie liquids or purees. If the device detects a high proportion of liquid intake, then actions will be taken to inhibit the next liquid intake. Another example of unhealthy ingestion would be when the patient has consumed too many calories over a certain period of time based on food content detection.

Figure 8A:
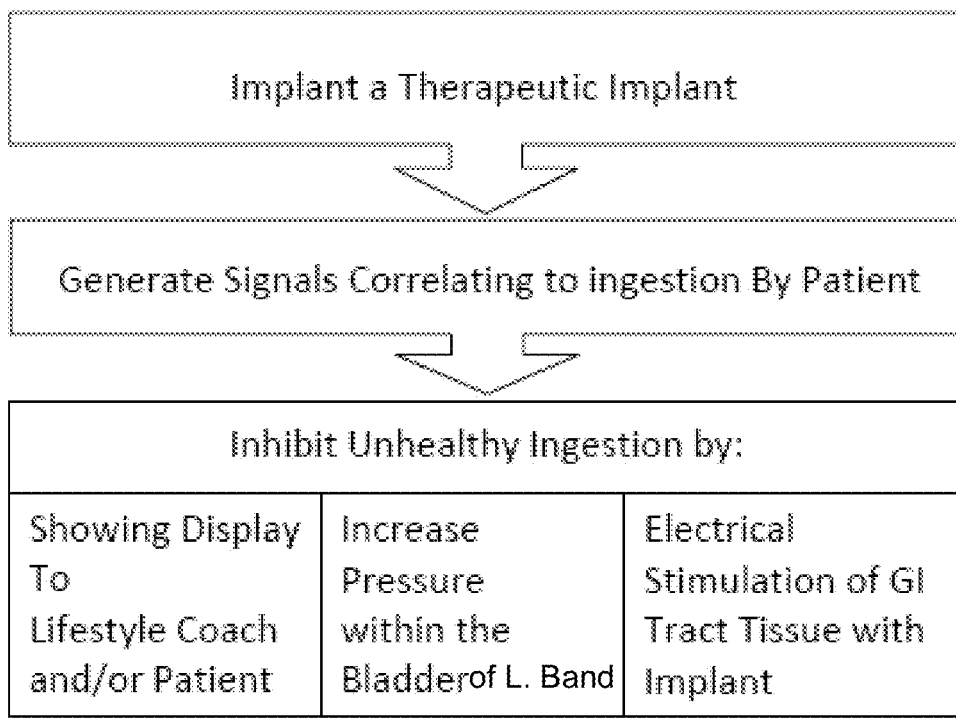
FIG. 8A-8E show alternative treatments method comprising the therapeutic implant.

In some cases, as shown in FIG. 8A, a therapeutic implant comprising a gastric band sensor system or an intragastric balloon sensor system 2010 is implanted into a patient. The sensor(s) in the system will sense ingestion by the patient and generate signals correlating to the ingestion 2020. Ingestion deemed unhealthy will be inhibited 2040 by either showing a display to a lifestyle coach and/or patient 2050, an increased pressure within the bladder of the lap band or within the intragastric balloon 2060, or electrical stimulation of the gastrointestinal tract tissue with the implant 2070.

Figure 8B:
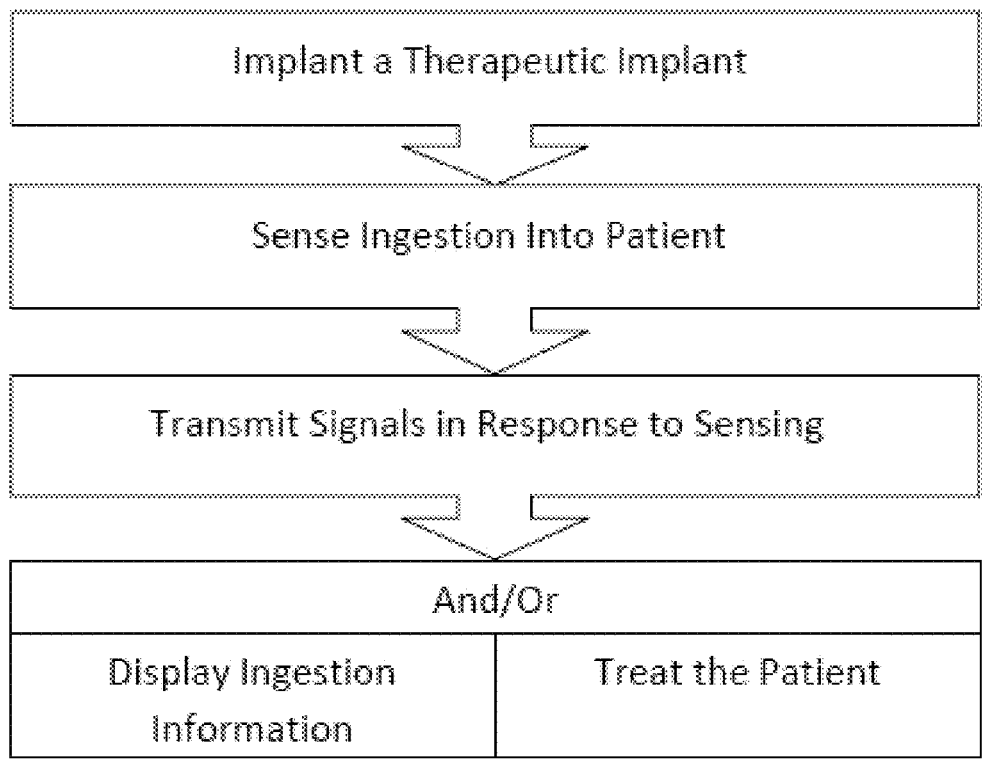

In some cases, as shown by FIG. 8B, a therapeutic implant comprising a gastric band sensor system or an intragastric balloon sensor system 2010 is implanted into a patient. The sensor(s) in the system will sense ingestion by the patient 2080 and signals will be transmitted in response to the sensing 2090, and ingestion information will be displayed to the patient 2100 and/or the patient will be treated 2110.

Figure 8C:
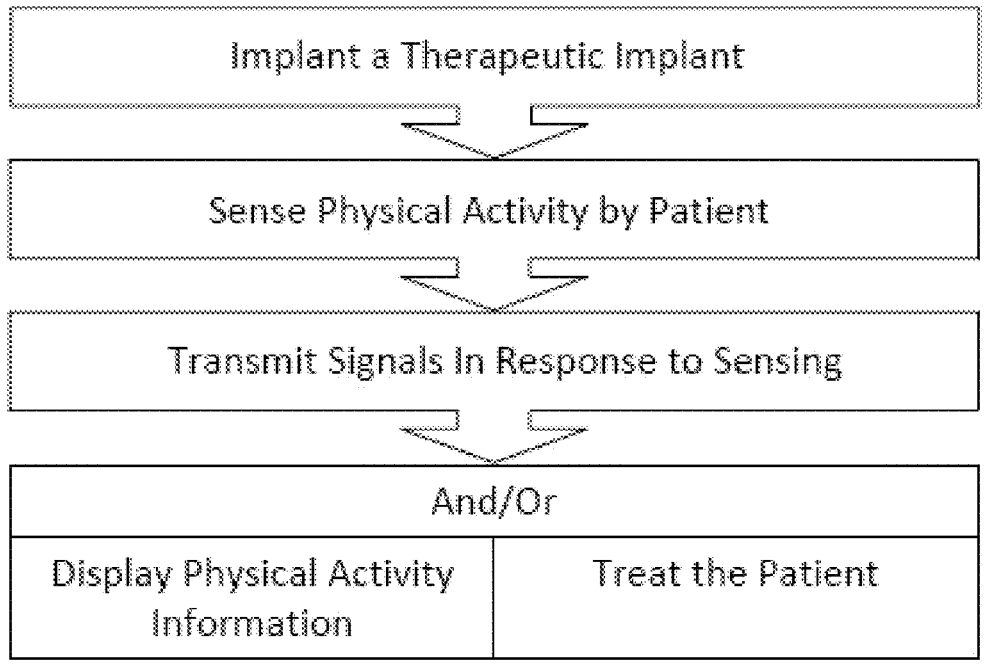

In some cases, as shown by FIG. 8C, a therapeutic implant comprising a gastric band sensor system or an intragastric balloon sensor system 2010 is implanted into a patient. The sensor(s) in the system will sense physical activity by the patient 2120 and signals will be transmitted in response to the sensing 2130, and physical activity information will be displayed to the patient 2140 and/or the patient will be treated 2150. In an alternative embodiment, the patient will receive both ingestion and activity information, in terms of energy balance; thus the patient will be able to easily visualize whether the calorie intake has been larger than the calorie output, or vice versa.

Figure 8D:
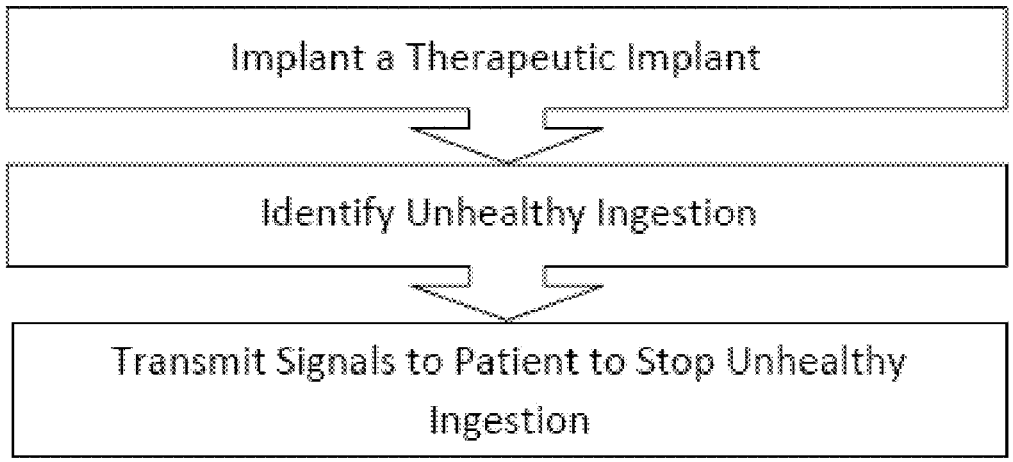

In some cases, as shown in FIG. 8D, a therapeutic implant comprising a gastric band sensor system or an intragastric balloon sensor system 2010 is implanted into a patient. Upon identification of unhealthy ingestion 2160, signals will be transmitted to the patient to stop the unhealthy ingestion 2170.

Figure 8E:
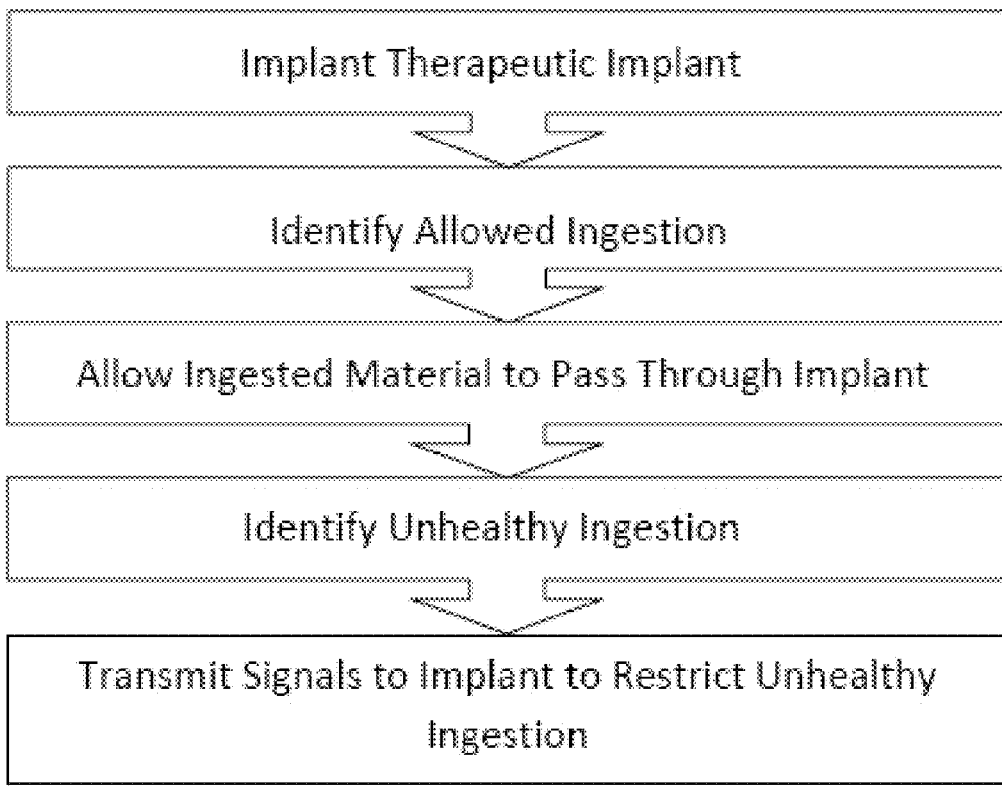

FIG. 8E shows another alternative treatment method where a therapeutic implant comprising a gastric band sensor system or an intragastric balloon sensor system 2010 is implanted into a patient. Allowed ingestions are identified 2180 and the ingested material is allowed to pass through the implant system 2190. Unhealthy ingestions are identified 2200 and signals are transmitted to the implant to restrict unhealthy ingestion 2210.

While exemplary embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A therapeutic implant system for treating an overweight patient, the patient having a gastrointestinal tract and an unhealthy ingestion pattern, the therapeutic implant system comprising:

an ingestion restricting implant body deployable along the gastrointestinal tract so as to separate the gastrointestinal tract into a restricted portion of the gastrointestinal tract and a gastric pouch portion of the gastrointestinal tract upstream of the restricted portion, the implant body comprising a gastric band defining a channel therethrough, the gastrointestinal tract extendable through the channel of the implant body, wherein the gastric band comprises a fluid-filled pressure bladder disposed between the channel and a support structure such that changes in a fluid pressure within the fluid pressure bladder correspond with changes in an engagement force between the gastrointestinal tract and the gastric band;

a sensor coupleable to the gastric pouch portion of the gastrointestinal pouch so that signals are generated in response to transient changes in the gastric pouch and the signals indicate an ingestion event;
a processor coupled to the signal generator and the implant body;
a display coupled to the processor, the display showing eating events identified in response to the signals during a plurality of days and configured for communicating feedback to the patient, a peer group member, a health care professional, or a lifestyle coach;
an actuator coupled to the processor so as to alter the fluid pressure within the bladder in response to the ingestion event; and
at least two electrodes coupled to the processor so as to stimulate tissue of the gastrointestinal tract such that, in response to the signals, the unhealthy ingestion pattern by the patient is inhibited in use sufficiently to modify the unhealthy ingestion pattern toward a healthier ingestion pattern.

2. The system of claim 1, wherein signals are transmitted to the bladder from the processor, and wherein the altering of the engagement force is induced by an actuator in response to the sensor signals so that the pressure within the bladder is decreased each day to allow healthy ingestion and increased each day to inhibit unhealthy ingestion.

3. A system for treating an obese patient, the patient having a gastrointestinal tract, the system comprising:
an ingestion restricting implant body deployable along the gastrointestinal tract;
at least two sensors so as to transmit signals in response to ingestion into the patient in use, wherein the at least two sensors include a transgastric probe having a probe body and a transgastric wall traversing portion, the at least two sensors separated along the probe body from the transgastric wall traversing portion so as to be disposed within an interior of the gastrointestinal tract; and
a processor coupled to the at least two sensors, the processor, in response to the signals, generating output comprising at least one member selected from the group consisting of:
ingestion display signals based on ingestion into the patient, and
patient treatment signals.

4. The system of claim 3, wherein the gastrointestinal tract includes a gastric pouch and the at least two sensors are disposed within an interior of the gastric pouch.

5. The system of claim 3, wherein the at least two sensors are selected from the group consisting of a temperature sensor, a visible color sensor, a pressure sensor, a temperature sensor, an optical sensor, an impedance sensor, a pH sensor, an acoustic sensor, an eccelerometer, a heart-rate sensor, and/or an infrared light detector.

6. The system of claim 3, further comprising at least one of:
a display coupled to the processor, the display showing ingestion events identified in response to the display signals during a plurality of days and configured for communicating feedback to the patient or other individuals;
an actuator coupled to the processor so as to alter the ingestion restricting implant body in response to the ingestion event; and
at least two electrodes coupled to the processor so as to stimulate tissue of the gastrointestinal tract in response to the ingestion event.

7. The system of claim 6, wherein altering the ingestion restricting implant body includes increasing the restriction when the ingestion event is sensed to be unhealthy and decreasing the restriction when the ingestion event is sensed to be health.

8. A therapeutic implant system for treating a patient, the patient having a gastrointestinal tract and an unhealthy ingestion pattern, the therapeutic implant system comprising:
an ingestion restricting implant body implantable along the gastrointestinal tract so as to separate the gastrointestinal tract into a restricted portion of the gastrointestinal tract and a gastric pouch portion of the gastrointestinal tract upstream of the restricted portion;
at least two sensors configured to engage the gastric pouch portion, wherein the sensor is included in a transgastric probe having a probe body and a transgastric wall traversing portion, the sensor separated along the probe body from the wall traversing portion so as to be disposed within an interior of the gastric pouch; and
a processor coupleable to the sensor so as to transmit signals therebetween, wherein the signals are transmitted in correlation with transient changes in the gastric pouch potion of the gastrointestinal tract in use.

9. The system of claim 8, wherein two or more electrodes are coupled to the processor, the electrodes configured to deliver electrical stimulation to the gastrointestinal tract.

10. The system of claim 9, wherein the two or more electrodes are mounted along the body of the transgastric probe.

11. The system of claim 8, wherein the at least two sensors may be coupled to the processor and configured to generate signals and the processor may be configured to process the signals so as to identify transient changes in the gastric pouch of the gastrointestinal tract.

12. The therapeutic implant of claim 8, wherein the implant body has a first configuration and a second configuration, the size, compliance, or shape of the implant body in the second configuration being different than the size, compliance, or shape of the implant body in the first configuration such that the implant body has an enhanced inhibition of ingestion in the second configuration.

13. A method for treating an obese patient, the patient having a gastrointestinal tract, the method comprising:
deploying at least a portion of an implant along the gastrointestinal tract, the implant having a body, at least three sensors and a processor;
identifying, during a day and in response to signals sent from the sensors to the processor, a candidate characterization of an ingested material; wherein the at least three sensors of the deployed implant include a transgastric probe having a probe body and a transgastric wall traversing portion, the sensor separated along the probe body from the wall traversing portion so as to be disposed within an interior of the gastrointestinal tract;
determining whether the ingested material constitutes an allowed ingestion in response to the candidate characterization, and if so, allowing the ingested material to traverse the body of the implant along the gastrointestinal tract;
determining whether the ingested material constitutes an unhealthy ingestion in response to the candidate characterization, and if so, transmitting signals from the processor to the body so as to alter a shape, compliance, and/or size of the body such that the body restricts the unhealthy ingestion.

14. The method of claim 13, wherein the transgastric probe may include two or more members selected from the group consisting of a temperature sensor, an electrode, and a visible color sensor and/or an infrared light detector.

15. The method of claim 13 further comprising:
communicating feedback to the patient, a peer group member, a health care professional, and/or a lifestyle coach, wherein the feedback is based on the determination of whether the ingested material constitutes an unhealthy ingestion or an allowed ingestion.

16. The method of claim 15, wherein communicating feedback provides a behavioral modification component for treating the obese patient.

17. The method of claim 13, wherein the feedback is communicated securely via website, email, telephone, or text message.

18. A therapeutic implant system for treating an overweight patient, the patient having a gastrointestinal tract and an unhealthy ingestion pattern, the therapeutic implant system comprising:
an ingestion restricting implant body deployable along the gastrointestinal tract so as to separate the gastrointestinal tract into different portions; wherein the implant comprises a first gastric band and a second gastric band; the first gastric band located superior relative to the second gastric band, each gastric band defining a channel through the gastrointestinal tract; wherein the first gastric band comprises a fluid-filled pressure bladder disposed between the channel and a support structure such that changes in a fluid pressure within the bladder correspond with changes in an engagement force between the gastrointestinal tract and the first gastric band;
at least two sensors coupleable to the first and/or second gastric bands, the sensors capable of generating signals in response to transient changes in the gastrointestinal tract indicative of an ingestion event;
a processor coupled to a signal generator and the implant body;
a display coupled to the processor, the display showing ingestion events identified in response to the signals during a plurality of days and configured for communicating feedback to the patient, a peer group member, a health care professional, or a lifestyle coach;
an actuator coupled to the processor so as to alter the fluid pressure within the bladder in response to the ingestion event; and
at least two electrodes coupled to the processor so as to stimulate tissue of the gastrointestinal tract such that, in response to the signals, the unhealthy ingestion pattern of the patient is inhibited in use sufficiently to modify the unhealthy ingestion pattern toward a healthier ingestion pattern.

19. The system of claim 18, wherein the first gastric band increases fluid pressure in response to a sensed unhealthy ingestion pattern so as to discourage the ingestion event and restrict food intake.

20. The system of claim 18, wherein stimulating the tissue of the gastrointestinal tract curbs the patient's appetite.

21. The system of claim 18, wherein each gastric band has different elasticities and each elasticity may be dynamically adjusted.

22. The system of claim 18, wherein the first and/or second gastric bands are secured in place with seromuscular sutures.

* * * * *